United States Patent
Graham et al.

(10) Patent No.: US 11,103,552 B2
(45) Date of Patent: Aug. 31, 2021

(54) HIGH CONCENTRATION VEGF RECEPTOR FUSION PROTEIN CONTAINING FORMULATIONS

(71) Applicant: Regeneron Pharmaceuticals, Inc., Tarrytown, NY (US)

(72) Inventors: Kenneth S. Graham, Pleasant Valley, NY (US); Saurabh Wadhwa, Nanuet, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 5 days.

(21) Appl. No.: 16/409,631

(22) Filed: May 10, 2019

(65) Prior Publication Data
US 2019/0343918 A1   Nov. 14, 2019

Related U.S. Application Data

(60) Provisional application No. 62/669,506, filed on May 10, 2018, provisional application No. 62/752,127, filed on Oct. 29, 2018, provisional application No. 62/769,876, filed on Nov. 20, 2018, provisional application No. 62/813,882, filed on Mar. 5, 2019.

(51) Int. Cl.
| | |
|---|---|
| *A61K 38/17* | (2006.01) |
| *A61K 38/18* | (2006.01) |
| *C07K 14/71* | (2006.01) |
| *C07K 19/00* | (2006.01) |
| *A61P 27/02* | (2006.01) |
| *A61K 9/00* | (2006.01) |
| *A61K 47/12* | (2006.01) |
| *A61K 47/18* | (2017.01) |
| *A61K 47/22* | (2006.01) |
| *A61K 47/26* | (2006.01) |

(52) U.S. Cl.
CPC .......... *A61K 38/179* (2013.01); *A61K 9/0048* (2013.01); *A61K 47/12* (2013.01); *A61K 47/183* (2013.01); *A61K 47/22* (2013.01); *A61K 47/26* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 5,580,856 | A | 12/1996 | Prestrelski et al. |
| 6,136,346 | A | 10/2000 | Eljamal et al. |
| 6,171,586 | B1 | 1/2001 | Lam et al. |
| 6,267,958 | B1 | 7/2001 | Andya et al. |
| 6,358,530 | B1 | 3/2002 | Eljamal et al. |
| 6,582,729 | B1 | 6/2003 | Eljamal et al. |
| 6,586,574 | B1 | 7/2003 | Hansen |
| 6,652,875 | B1 | 11/2003 | Bannister |
| 6,685,940 | B2 | 2/2004 | Andya et al. |
| 6,833,349 | B2 | 12/2004 | Xia et al. |
| 6,875,432 | B2 | 4/2005 | Liu et al. |
| 7,060,268 | B2 | 6/2006 | Andya et al. |
| 7,070,959 | B1 | 7/2006 | Papadopoulos et al. |
| 7,087,411 | B2 | 8/2006 | Daly et al. |
| 7,279,159 | B2 | 10/2007 | Daly et al. |
| 7,303,746 | B2 | 12/2007 | Wiegand et al. |
| 7,303,747 | B2 | 12/2007 | Wiegand et al. |
| 7,306,799 | B2 | 12/2007 | Wiegand et al. |
| 7,374,757 | B2 | 5/2008 | Papadopoulos et al. |
| 7,374,758 | B2 | 5/2008 | Papadopoulos et al. |
| 7,396,664 | B2 | 7/2008 | Daly et al. |
| 7,399,612 | B2 | 7/2008 | Daly et al. |
| 7,521,049 | B2 | 4/2009 | Wiegand et al. |
| 7,524,499 | B2 | 4/2009 | Papadopoulos et al. |
| 7,608,261 | B2 | 10/2009 | Furfine et al. |
| 7,635,474 | B2 | 12/2009 | Daly et al. |
| 7,648,702 | B2 | 1/2010 | Gombotz et al. |
| 7,682,609 | B2 | 3/2010 | Andya et al. |
| 7,704,500 | B2 | 4/2010 | Papadopoulos et al. |
| 7,807,164 | B2 | 10/2010 | Furfine et al. |
| 7,851,443 | B2 | 12/2010 | Bissery et al. |
| 7,956,160 | B2 | 6/2011 | Krishnan et al. |
| 7,964,377 | B2 | 6/2011 | Papadopoulos et al. |
| 7,972,598 | B2 | 7/2011 | Daly et al. |
| 8,029,791 | B2 | 10/2011 | Papadopoulos et al. |
| 8,084,234 | B2 | 12/2011 | Papadopoulos et al. |
| 8,092,803 | B2 | 1/2012 | Furfine et al. |
| 8,110,546 | B2 | 2/2012 | Dix et al. |
| 8,216,575 | B2 | 7/2012 | Yu |

(Continued)

FOREIGN PATENT DOCUMENTS

| | | |
|---|---|---|
| AL | 2013/063510 A1 | 5/2013 |
| CA | 2990582 C | 6/2020 |

(Continued)

OTHER PUBLICATIONS

Anonymous et al., "Highlights of Prescribing Information," XP055565606 [retreived from the Internet:URL:https://web.archive.ordweb/20161206164049if_/https://www.regeneron.com/sites/default/files/EYLEA_FPI.pdf retreived on Mar. 7, 2019] (2016).

(Continued)

*Primary Examiner* — Christine J Saoud
*Assistant Examiner* — Jon M Lockard
(74) *Attorney, Agent, or Firm* — Schwabe, Williamson & Wyatt PC; Thomas Triolo

(57) ABSTRACT

The present invention provides ophthalmic formulations having high concentrations of vascular endothelial growth factor (VEGF) receptor fusion protein and high stability during storage. Methods for treating angiogenic eye disorders using the high concentration formulations are also provided.

36 Claims, 37 Drawing Sheets
Specification includes a Sequence Listing.

(56) References Cited

U.S. PATENT DOCUMENTS

| | | |
|---|---|---|
| 8,343,737 B2 | 1/2013 | Papadopoulos et al. |
| 8,372,396 B2 | 2/2013 | Andya et al. |
| 8,404,638 B2 | 3/2013 | Dix et al. |
| 8,481,046 B2 | 7/2013 | Furfine et al. |
| 8,568,720 B2 | 10/2013 | Morichika et al. |
| 8,623,395 B2 | 1/2014 | de Juan, Jr. et al. |
| 8,647,842 B2 | 2/2014 | Papadopoulos et al. |
| 8,710,004 B2 | 4/2014 | Dix et al. |
| 8,802,107 B2 | 8/2014 | Furfine et al. |
| 8,921,316 B2 | 12/2014 | Dix et al. |
| 8,961,964 B2 | 2/2015 | Liu et al. |
| 9,139,644 B2 | 9/2015 | Papadopoulos et al. |
| 9,254,338 B2 | 2/2016 | Yancopoulos |
| 9,283,273 B2 | 3/2016 | Andya et al. |
| 9,340,594 B2 | 5/2016 | Furfine et al. |
| 9,402,898 B2 | 8/2016 | Walsh et al. |
| 9,416,167 B2 | 8/2016 | Dix et al. |
| 9,474,803 B2 | 10/2016 | Park et al. |
| 9,511,140 B2 | 12/2016 | Dix et al. |
| 9,580,489 B2 | 2/2017 | Furfine et al. |
| 9,636,400 B2 | 5/2017 | Dix et al. |
| 9,669,069 B2 | 6/2017 | Yancopoulos |
| 9,708,386 B2 | 7/2017 | Papadopoulos et al. |
| 9,884,019 B2 | 2/2018 | Tchessalov et al. |
| 9,914,763 B2 | 3/2018 | Furfine et al. |
| 9,982,032 B2 | 5/2018 | Park et al. |
| 10,130,681 B2 | 11/2018 | Yancopoulos |
| 10,166,293 B2 | 1/2019 | Liu et al. |
| 10,400,025 B2 | 9/2019 | Furfine et al. |
| 10,406,226 B2 | 9/2019 | Dix et al. |
| 10,413,513 B2 | 9/2019 | Fabio et al. |
| 10,464,992 B2 | 11/2019 | Furfine et al. |
| 10,501,523 B2 | 12/2019 | Chiron-Blondel et al. |
| 10,576,128 B2 | 3/2020 | Sigl |
| 10,610,600 B2 | 4/2020 | Soane et al. |
| 10,689,438 B2 | 6/2020 | Zhang et al. |
| 10,799,642 B2 | 10/2020 | Wong et al. |
| 10,828,345 B2 | 11/2020 | Yancopoulos |
| 10,857,205 B2 | 12/2020 | Yancopoulos |
| 10,857,231 B2 | 12/2020 | Dix et al. |
| 10,869,924 B2 | 12/2020 | Andrews et al. |
| 10,888,601 B2 | 1/2021 | Yancopoulos |
| 10,898,572 B2 | 1/2021 | Kameoka et al. |
| 10,925,927 B2 | 2/2021 | Brockmeyer et al. |
| 10,973,879 B2 | 4/2021 | Vitti et al. |
| 2003/0113316 A1 | 6/2003 | Kaisheva et al. |
| 2003/0138417 A1 | 7/2003 | Kaisheva et al. |
| 2003/0180287 A1 | 9/2003 | Gombotz et al. |
| 2003/0206939 A1 | 11/2003 | Bannister |
| 2004/0197324 A1 | 10/2004 | Liu et al. |
| 2004/0266686 A1 | 12/2004 | Xia et al. |
| 2005/0013867 A1 | 1/2005 | Lehrman et al. |
| 2005/0112061 A1 | 5/2005 | Holash et al. |
| 2005/0123509 A1 | 6/2005 | Lehrman et al. |
| 2005/0196340 A1 | 9/2005 | Holash et al. |
| 2006/0217311 A1 | 9/2006 | Dix et al. |
| 2007/0053900 A1 | 3/2007 | Liu et al. |
| 2007/0172479 A1 | 7/2007 | Warne et al. |
| 2007/0190058 A1 | 8/2007 | Shams |
| 2007/0237758 A1 | 10/2007 | Barry et al. |
| 2008/0064856 A1 | 3/2008 | Warne et al. |
| 2008/0071063 A1 | 3/2008 | Allan et al. |
| 2009/0280129 A1 | 11/2009 | Liu et al. |
| 2010/0158899 A1 | 6/2010 | Andya et al. |
| 2010/0254985 A1 | 10/2010 | Allan et al. |
| 2011/0028698 A1 | 2/2011 | Papadopoulos et al. |
| 2011/0236383 A1 | 9/2011 | Andya et al. |
| 2012/0114646 A1 | 5/2012 | Tchessalov et al. |
| 2012/0121580 A1 | 5/2012 | Bhambhani et al. |
| 2012/0183531 A1 | 7/2012 | Lucas et al. |
| 2013/0029909 A1 | 1/2013 | Ryan et al. |
| 2013/0058958 A1 | 3/2013 | Bowen et al. |
| 2013/0084635 A1 | 4/2013 | Papadopoulos et al. |
| 2013/0236448 A1 | 9/2013 | Kamerzell et al. |
| 2013/0323242 A1 | 12/2013 | Everett et al. |
| 2014/0051642 A1 | 2/2014 | Castan |
| 2014/0294816 A1 | 10/2014 | Shima et al. |
| 2014/0348852 A1 | 11/2014 | Vos et al. |
| 2015/0150982 A1 | 6/2015 | Michael et al. |
| 2015/0157709 A1 | 6/2015 | Everett et al. |
| 2015/0182623 A1 | 7/2015 | Everett et al. |
| 2015/0202288 A1 | 7/2015 | Shima et al. |
| 2015/0209431 A1 | 7/2015 | Ma et al. |
| 2016/0144025 A1 | 5/2016 | Vitti et al. |
| 2016/0244504 A1 | 8/2016 | Dix et al. |
| 2016/0340420 A1 | 11/2016 | Zhang et al. |
| 2016/0375133 A1 | 12/2016 | Bhambhani et al. |
| 2016/0376342 A1 | 12/2016 | Park et al. |
| 2017/0051039 A1 | 2/2017 | Gombotz et al. |
| 2017/0073407 A1 | 3/2017 | Dix et al. |
| 2017/0209582 A1 | 7/2017 | Park et al. |
| 2018/0055940 A1 | 3/2018 | Ma et al. |
| 2018/0099049 A1 | 4/2018 | Tang et al. |
| 2018/0221280 A1 | 8/2018 | Fabio et al. |
| 2018/0289623 A1 | 10/2018 | Chen et al. |
| 2018/0326126 A1 | 11/2018 | Fiedler |
| 2018/0333493 A1 | 11/2018 | Shenoy |
| 2019/0000919 A1 | 1/2019 | Brockmeyer et al. |
| 2019/0060241 A1 | 2/2019 | Patel et al. |
| 2019/0144523 A1 | 5/2019 | Gombotz et al. |
| 2019/0160145 A1 | 5/2019 | Im et al. |
| 2019/0275021 A1 | 9/2019 | Jiang et al. |
| 2019/0290725 A1 | 9/2019 | Vitti et al. |
| 2019/0298801 A1 | 10/2019 | Kerwin et al. |
| 2019/0343918 A1 | 11/2019 | Graham et al. |
| 2019/0358323 A1 | 11/2019 | Liu et al. |
| 2020/0017572 A1 | 1/2020 | Furfine et al. |
| 2020/0046834 A1 | 2/2020 | Tang et al. |
| 2020/0108064 A1 | 4/2020 | Horn et al. |
| 2020/0114002 A1 | 4/2020 | Soane et al. |
| 2020/0131246 A1 | 4/2020 | Furfine et al. |
| 2020/0155678 A1 | 5/2020 | Chen et al. |
| 2020/0206028 A1 | 7/2020 | Boschetti et al. |
| 2020/0214888 A1 | 7/2020 | Bryant et al. |
| 2020/0230237 A1 | 7/2020 | Kauvar et al. |
| 2020/0237862 A1 | 7/2020 | Sigl |
| 2020/0237997 A1 | 7/2020 | Brockmeyer et al. |
| 2020/0246423 A1 | 8/2020 | Liu et al. |
| 2020/0253875 A1 | 8/2020 | Coffman et al. |
| 2020/0255496 A1 | 8/2020 | Wexler-Cohen et al. |
| 2020/0281923 A1 | 9/2020 | Wang |
| 2020/0283492 A1 | 9/2020 | Lee et al. |
| 2020/0338164 A1 | 10/2020 | Wexler-Cohen et al. |
| 2020/0353041 A1 | 11/2020 | Ferrara et al. |
| 2020/0390693 A1 | 12/2020 | Kim et al. |
| 2020/0390724 A1 | 12/2020 | Arkin et al. |
| 2020/0390725 A1 | 12/2020 | Arkin et al. |
| 2020/0397729 A1 | 12/2020 | Tempesta et al. |
| 2021/0000758 A1 | 1/2021 | Arkin et al. |
| 2021/0008158 A1 | 1/2021 | Hohman et al. |
| 2021/0008199 A1 | 1/2021 | Zhang et al. |
| 2021/0023173 A1 | 1/2021 | Yancopoulos |
| 2021/0077624 A1 | 3/2021 | Dix et al. |
| 2021/0085753 A1 | 3/2021 | Yancopoulos |
| 2021/0100856 A1 | 4/2021 | Gasmi et al. |
| 2021/0115124 A1 | 4/2021 | Koenig et al. |
| 2021/0121524 A1 | 4/2021 | Yancopoulos |

FOREIGN PATENT DOCUMENTS

| | | |
|---|---|---|
| EP | 1767546 B1 | 3/2012 |
| EP | 3452075 A1 | 3/2019 |
| EP | 3710055 A1 | 9/2020 |
| EP | 3713591 A1 | 9/2020 |
| EP | 3736574 A1 | 11/2020 |
| EP | 3774894 A1 | 2/2021 |
| EP | 3785701 A1 | 3/2021 |
| WO | 97/004801 A1 | 2/1997 |
| WO | 98/045331 A3 | 10/1998 |
| WO | 2000/075319 A1 | 12/2000 |
| WO | 2002/030463 A2 | 4/2002 |
| WO | 2002/060489 A1 | 8/2002 |
| WO | 2003/072060 A2 | 9/2003 |
| WO | 2004/091658 A1 | 10/2004 |

(56) References Cited

FOREIGN PATENT DOCUMENTS

| | | |
|---|---|---|
| WO | 2005/000895 A2 | 1/2005 |
| WO | 2006/104852 A2 | 10/2006 |
| WO | 2006/138181 A2 | 12/2006 |
| WO | 2007/014170 A2 | 2/2007 |
| WO | 07/112675 A1 | 10/2007 |
| WO | 2007/149334 A2 | 12/2007 |
| WO | 2009/015345 A1 | 1/2009 |
| WO | 2010/148321 A1 | 12/2010 |
| WO | 2011/104381 A2 | 9/2011 |
| WO | 2011/109365 A2 | 9/2011 |
| WO | 2011/139718 A1 | 11/2011 |
| WO | 2012/003437 A1 | 1/2012 |
| WO | 2012/019047 A2 | 2/2012 |
| WO | 2012/097019 A1 | 7/2012 |
| WO | 2013/112438 A1 | 8/2013 |
| WO | 2014/084508 A1 | 6/2014 |
| WO | 2014/193821 A1 | 12/2014 |
| WO | 2015/173260 A1 | 11/2015 |
| WO | 2016/045626 A1 | 3/2016 |
| WO | 2016/045627 A1 | 3/2016 |
| WO | 16/094673 A1 | 6/2016 |
| WO | 2016/085750 A1 | 6/2016 |
| WO | 2016/208989 A1 | 12/2016 |
| WO | 2017/051273 A1 | 3/2017 |
| WO | 2017/085253 A1 | 5/2017 |
| WO | 2017/087798 A1 | 5/2017 |
| WO | 2017/095848 A1 | 6/2017 |
| WO | 2017/120601 A1 | 7/2017 |
| WO | 2017/129685 A1 | 8/2017 |
| WO | 2018/033482 A1 | 2/2018 |
| WO | 2018/035470 A9 | 2/2018 |
| WO | 2018/063963 A1 | 4/2018 |
| WO | 2018/094316 A1 | 5/2018 |
| WO | 2018/107005 A1 | 6/2018 |
| WO | 2018/116198 A1 | 6/2018 |
| WO | 2018/199408 A1 | 11/2018 |
| WO | 2018/217995 A1 | 11/2018 |
| WO | 18/229034 A1 | 12/2018 |
| WO | 19/020777 A1 | 1/2019 |
| WO | 2019/036619 A1 | 2/2019 |
| WO | 19/055902 A1 | 3/2019 |
| WO | 2019/099921 A2 | 5/2019 |
| WO | 2019/099965 A1 | 5/2019 |
| WO | 19/124946 A1 | 6/2019 |
| WO | 2019/173767 A1 | 9/2019 |
| WO | 2019/214551 A1 | 11/2019 |
| WO | 2020/008361 A1 | 1/2020 |
| WO | 2020/055123 A1 | 3/2020 |
| WO | 2020/087003 A1 | 4/2020 |
| WO | 2020/103958 A1 | 5/2020 |
| WO | 2020/127641 A1 | 6/2020 |
| WO | 20/160133 A1 | 8/2020 |
| WO | 2020/165132 A1 | 8/2020 |
| WO | 2020/167848 A1 | 8/2020 |
| WO | 2020/197230 A1 | 10/2020 |
| WO | 2020/205716 A1 | 10/2020 |
| WO | 2020/206320 A1 | 10/2020 |
| WO | 2020/219550 A1 | 10/2020 |
| WO | 2020/225213 A1 | 11/2020 |
| WO | 2020/239051 A1 | 12/2020 |
| WO | 2021/048779 A2 | 3/2021 |
| WO | 2021/050009 A2 | 3/2021 |
| WO | 2021/053001 A1 | 3/2021 |

OTHER PUBLICATIONS

Shire et al., "Formulation of proteins and monoclonal antibodies mAbs," Monoclonal Antibodies: Meeting the Challenges in Manufacturing, Formulation, Delivery and Stability of Final Drug Product, p. 93-120, XP009192951 (2015).
Stewart, "Aflibercept (VEGF-TRAP): The Next Anti-VEGF Drug," Department of Ophthalmology, Mayo Clinic Florida, vol. (10):497-508, (2011). XP009172512.
WIPO Application No. PCT/US2019/031879, PCT International Search Report and Written Opinion of the International Searching Authority dated Sep. 25, 2019.
Baynes et al., "Role of arginine in the stabilization of proteins against aggregation," Biochemistry; vol. 44(12):4919-25. (2005).
Daugherty et al., "Formulation and delivery issues for monoclonal antibody therapeutics," Science Direct, Advanced Drug Delivery Reviews; vol. 58(5-6):686-706. (2006).
Eylea, Initial U.S. Approval: Jan. 10, 2011 (2011).
Freeman et al., "High-dose Aflibercept for Eyes with Wet Age-Related Macular Degeneration Resistant to Standard Therapy," Investigative Ophthalmology & Visual Science; vol. 56 (2015).
Giannos et al., "Formulation Stabilization and Disaggregation of Bevacizumab Ranibizumab and Aflibercept in Dilute Solutions," Pharm Res; vol. 35(4):78, 1-15 doi: 10.1007/s11095-018-2368-7 (2018).
Hofmann et al., "Prediction of Protein Aggregation in High Concentration Protein Solutions Utilizing Protein-Protein Interactions Determined by Low Volume Static Light Scattering," Journal of Pharmaceutical Sciences, vol. 105(6): 1-10. doi: 10.1016/j.xphs.2016.03.022. (2016).
Kim et al., "Arginine as a protein stabilizer and destabilizer in liquid formulations," International Journal of Pharmaceutics; vol. 513(1-2):26-37. doi: 10.1016/j.ijpharm.2016.09.003. (2016).
Kim et al., "Preferential exclusion mechanism by carbohydrates on protein stabilization using thermodynamic evaluation," International Journal of Biological Macromolecules; vol. 109:311-322. doi: 10.1016/j.ijbiomac.2017.12.089. (2018).
Moreno et al., "Study of stability and biophysical characterization of ranibizumab and aflibercept," European Journal of Pharmaceutics and Biopharmaceutics, vol. 108;156-167; doi: 0.1016/j.ejpb.2016.09.003 (2016).
SA Transcripts, "Regeneron Pharmaceuticals (REGN) Q3 2018 Results—Earnings Call Transcript," Seeking Alpha: 1-27, (Nov. 6, 2018). [https://seekingalpha.com/article/4219037-regeneron-pharmaceuticals-regn-q3-2018-results-earnings-call-transcript?part=single].
Schleifer et al., "Regeneron Science to Medince," JP Morgan Jan. 29, 2019; Jan. 7, 2019.
Whitaker et al., "A Formulation Development Approach to Identify and Select Stable Ultra-High-Concentration Monoclonal Antibody Formulations With Reduced Viscosities," Journal of Pharmaceutical Sciences; Nov;106(11):3230-3241. doi: 10.1016/j.xphs.2017.06.017. (2017).
Zaltrap, "Injection for Intravenous Infusion Prescribing Information," Prescribing Information; 1-20, (2012). [http://products.sanofi.us/Zaltrap/Zaltrap.html].
"Phosphate buffer." Cold Spring Harbor Protocols, 2006.
"Guidance for industry Q1A(R2) stability testing of new drug substances and products." U.S. Department of Health and Human Services Food and Drug Administration, Rockville, MD, Nov. 2003.
Andersen & Krummen, Recombinant protein expression for therapeutic applications, Current Opinion in Biotechnology, 2002, 13: 117-123.
AVASTIN label.
Bontempo, Preformulation Development of Parenteral Biopharmaceuticals, Drugs and the Pharmaceutical Sciences, 1997, 85:91-108.
Brown et al., Primary Endpoint Results of a Phase II Study of Vascular Endothelial Growth Factor Trap-Eye in Wet Age-related Macular Degeneration, Ophthalmology vol. 118, No. 6, 1098-1097, Jun. 2011.
Brown et al., Ranibizumab versus verteporfin for neovascular age-related macular degeneration, N Engl J Med. Oct. 5, 2006;355(14):1432-44.
Brown et al., Ranibizumab versus verteporfin photodynamic therapy for neovascular age-related macular degeneration: Two-year results of the ANCHOR study, Ophthalmology. Jan. 2009;116(1):57-65.
Brown et al., Super-dose anti-VEGF (SAVE) trial: 2.0 mg intravitreal ranibizumab for recalcitrant neovascular macular degeneration-primary end point, Ophthalmology Feb. 2013;120(2):349-54-Epub Nov. 3, 2012.

(56) References Cited

OTHER PUBLICATIONS

Cai et al., The efficacy and safety of aflibercept and conbercept in diabetic macular edema, Drug Design, Development and Therapy 2018:12 3471-3483.

Cao et al., Aflibercept Action in a Rabbit Model of Chronic Retinal Neovascularization: Reversible Inhibition of Pathologic Leakage With Dose-Dependent Duration, Invest Ophthalmol Vis Sci. Feb. 1, 2018;59(2):1033-1044.

CATT Research Group, Ranibizumab and bevacizumab for neovascular age-related macular degeneration, N Engl J Med. May 19, 2011;364(20):1897-908-Epub Apr. 28, 2011.

Chaudhuri et al., High-Throughput Biophysical Analysis of Protein Therapeutics to Examine Interrelationships Between Aggregate Formation and Conformational Stability, The AAPS Journal 16(1): 48-64 (2013).

Chi et al., Physical Stability of Proteins in Aqueous Solution: Mechanism and Driving Forces in Nonnative Protein Aggregation, Pharmaceutical Research, Sep. 2003, vol. 20, No. 9, 1325-1336.

Conbercept product brochure, Angiogenesis, Exudation, and Degeneration 2019 meeting, Miami, Florida (Feb. 9, 2019).

Do et al., Pharmacokinetic Study of Intravitreal Aflibercept in Humans with Neovascular Age-Related Macular Degeneration Retina Apr. 2020;40(4):643-647.

Drug Vehicle (Code C927), National Cancer Institute (NCI). Retrieved Mar. 29, 2021, from URL: https://ncithesaurus.nci.nih.gov/ncitbrowser/ConceptReport.jsp?dictionary=NCI_Thesaurus&ns=ncit& code=C927.

Engelbert et al., The "Treat and Extend" Dosing Regimen of Intravitreal Anti-Vascular Endothelial Growth Factor Therapy for Neovascular Age-Related Macular Degeneration, Opthamology Management, Issue 42, Jun. 2010.

Event Brief of Q1 2019 Regeneron Pharmaceuticals Inc Earnings Call—Final FD (Fair Disclosure) Wire, May 7, 2019.

Event Brief of Q2 2018 Regeneron Pharmaceuticals Inc Earnings Call—Final, FD (Fair Disclosure) Wire, Aug. 2, 2018.

Event Brief of Q3 2018 Regeneron Pharmaceuticals Inc Earnings Call—Final FD (Fair Disclosure) Wire, Nov. 6, 2018.

Event Brief of Q4 2018 Regeneron Pharmaceuticals Inc Earnings Call—Final FD (Fair Disclosure) Wire Feb. 6, 2019.

Fraser HM, Wilson H, Rudge JS, Wiegand SJ., Single injections of vascular endothelial growth factor trap block ovulation in the macaque and produce a prolonged, dose-related suppression of ovarian function.J Clin Endocrinol Metab. Feb. 2005;90(2):1114-22.

Heier et al., The 1-year results of CLEAR-IT 2, a phase 2 study of vascular endothelial growth factor trap-eye dosed as-needed after 12-week fixed dosing, Ophthalmology. Jun. 2011;118(6):1098-106.

HERCEPTIN label.

Holash et al., VEGF-Trap: A VEGF blocker with potent antitumor effects, PNAS, Aug. 20, 2002, vol. 99, No. 17, 11393-11398.

Holz et al., Single-Chain Antibody Fragment Vegf Inhibitor RTH258 for Neovascular Age-Related Macular Degeneration, Ophthalmology. May 2016;123(5):1080-1089-Epub Feb. 20, 2016.

Janeway et al., The structure of a typical antibody molecule, Immunobiology: The Immune System in Health and Disease. 5th edition. New York: Garland Science; 2001.

Kitchens et al., Comprehensive Review of Ocular and Systemic Safety Events with Intravitreal Aflibercept Injection in Randomized Controlled Trials, Ophthalmology, Jul. 2016;123(7):1511-20-Epub Apr. 12, 2016.

Lu & Sun, Profile of conbercept in the treatment of neovascular age-related macular degeneration, Drug Design, Development and Therapy 9: 2311-2320 (2015).

LUCENTIS label.

Lumitin product page (Chinese language including machine translation to English language), available at https://en.cnkh.com/products_information/01-Ophthalmology/Lumitin®(Conbercept_Ophthalmic_Solution).pdf, ;last accessed Mar. 29, 2021.

Major et al., Comparison of spectral-domain and time-domain optical coherence tomography in the detection of neovascular age-related macular degeneration activity, Retina. Jan. 2014;34(1):48-54.

Mark W. Johnson, MD, Antiangiogenic therapy an advanced treatment for AMD, Ocular Surgery News, Feb. 1, 2006.

Michael et al., Local acting Sticky-trap inhibits vascular endothelial growth factor dependent pathological angiogenesis in the eye, EMBO Molecular Medicine 6(5): 604-623 (2014).

Nguyen et al., A Phase I Study of Intravitreal Vascular Endothelial Growth Factor Trap-Eye in Patients with Neovascular Age-Related Macular Degeneration, Ophthalmology 2009;116:2141-2148.

Nguyen et al., Evaluation of very high- and very low-dose intravitreal aflibercept in patients with neovascular age-related macular degeneration, J Ocul Pharmacol Ther. Dec. 2012;28(6):581-8. Epub Jul. 9, 2012.

Parkins & Lashmar, The formulation of biopharmaceutical products, Pharmaceutical Science & Technology Today, Apr. 4, 2000, vol. 3, No. 4: 129-137.

Pieramici & Rabena, Anti-VEGF therapy: comparison of current and future agents, Eye (2008) 22, 1330-1336.

Press release, Novartis, Two-year data for Novartis brolucizumab reaffirm superiority versus aflibercept in reducing retinal fluid in patients with nAMD (Oct. 27, 2018).

Press Release, Regeneron: Regeneron Provides Update on Commercial and Pipeline Progress at J.P. Morgan Healthcare Conference, Jan. 7, 2019.

Press Release, Regeneron: Regeneron Reports First Quarter 2018 Financial and Operating Results, May 3, 2018.

Press Release, Regeneron: Regeneron Reports Fourth Quarter and Full Year 2018 Financial and Operating Results, Feb. 6, 2019.

Q1 2019 Regeneron Pharmaceuticals Inc Earnings Call—Final FD (Fair Disclosure) Wire, May 7, 2019.

Q2 2018 Regeneron Pharmaceuticals Inc Earnings Call—Final, FD (Fair Disclosure) Wire, Aug. 2, 2018.

Q3 2018 Regeneron Pharmaceuticals Inc Earnings Call—Final FD (Fair Disclosure) Wire, Nov. 6, 2018.

Q4 2018 Regeneron Pharmaceuticals Inc Earnings Call—Final FD (Fair Disclosure) Wire, Feb. 6, 2019.

Randolph & Jones, Surfactant-Protein Interactions, Rational Design of Stable Protein Formulations, 2002, pp. 159-175, Springer, Boston, MA.

RAPTIVA label.

Regeneron Annual Report 2018.

Regeneron Corporate Presentation, Mar. 2019.

Regeneron Gets a Win With Eylea Approval in Diabetic Retinopathy Scrip Intelligence, May 13, 2019.

Regeneron Pharmaceuticals Inc at J.P. Morgan 2019 Spring Biotech Conference Call—Final FD (Fair Disclosure) Wire, Mar. 15, 2019.

Regeneron Pharmaceuticals Inc at Morgan Stanley Healthcare Conference—Final FD (Fair Disclosure) Wire, Sep. 12, 2018.

Regeneron Pharmaceuticals Outlines Pipeline Progress, Shares 2019 Financial Guidance MT Newswires Live Briefs, Jan. 7, 2019.

Regeneron Provides Update on Commercial and Pipeline Progress at J.P. Morgan Healthcare Conference PR Newswire, Jan. 7, 2019.

Regeneron Provides Update on Commercial and Pipeline Progress at J.P. Morgan Healthcare Conference Plus Company Updates (PCU), Jan. 8, 2019.

Regeneron Reports Fourth Quarter and Full Year 2018 Financial and Operating Results PR Newswire, Feb. 6, 2019.

Regeneron Reports Fourth Quarter and Full Year 2018 Financial and Operating Results Plus Company Updates (PCU), Feb. 7, 2019.

Regeneron's Eylea hits double-digit growth for 2018, and it's 'far from done,' CEO says Indian Pharma Industry: Policies, Dec. 27, 2018.

Regeneron's Eylea hits double-digit growth for 2018, and it's 'far from done,' CEO says FiercePharma Marketing, Jan. 9, 2019.

REMICADE label.

Rosenfeld et al., Ranibizumab for neovascular age-related macular degeneration,N Engl J Med. Oct. 5, 2006;355(14):1419-31.

Rudge et al., VEGF Trap as a Novel Antiangiogenic Treatment Currently in Clinical Trials for Cancer and Eye Diseases, and

(56) References Cited

OTHER PUBLICATIONS

VelociGene®—based Discovery of the Next Generation of Angiogenesis Targets, Cold Spring Harbor Symposia on Quantitative Biology, 2005, 70: 411-418.
Sawada et al., Aqueous vascular endothelial growth factor and aflibercept concentrations after bimonthly intravitreal injections of aflibercept for age-related macular degeneration, Clinical and Experimental Ophthalmology (2017) 46:46-53.
Schelifer & Yancoupolos, JP Morgan Presentation Jan. 7, 2019.
SEC Form 10-K, Regeneron, Dec. 31, 2018.
SEC Form 10-Q, Regeneron, Mar. 31, 2019.
SEC Form 8-K, Regeneron, Jan. 7, 2019.
SIMULECT label.
Stacker et al., A Simple Bioassay for the Evaluation of Vascular Endothelial Growth Factors, Journal of Visualized Experiments, J. Vis. Exp. (109), e53867 (2016).
Stewart & Rosenfeld, Predicted biological activity of intravitreal VEGF Trap, Br J Ophthalmol May 2008;92(5):667-668—Epub Mar. 20, 2008.
Stewart, Extended Duration Vascular Endothelial Growth Factor Inhibition in the Eye: Failures, Successes, and Future Possibilities, Pharmaceutics 2018, 10, 21.
United States: Regeneron Provides Update on Commercial and Pipeline Progress at J.P. Morgan Healthcare Conference Tenders Info, Jan. 12, 2019.
Wang, Advanced protein formulations, Protein Science 24:1031-1039 (2015).
Wang-Gillam et al., A phase I study of subcutaneously administered aflibercept (VEGF trap) in a new formulation in patients with advanced solid tumors, Invest New Drugs (2012) 30:1958-1961.
Wulff et al., Prevention of Thecal Angiogenesis, Antral Follicular Growth, and Ovulation in the Primate by Treatment with Vascular Endothelial Growth Factor Trap R1R2, Endocrinology, Jul. 2002, 143(7): 2797-2807.
Wykoff et al., SAVE (Super-dose anti-VEGF) trial: 2.0 mg ranibizumab for recalcitrant neovascular age-related macular degeneration: 1-year results, Ophthalmic Surg Lasers Imaging Retina. Mar.-Apr. 2013;44(2):121-6.
Wykoff et al., Two Year SAVE Outcomes: 2.0 mg ranibizumab for recalcitrant neovascular AMD, Ophthalmology Sep. 2013;120(9):1945-6.
XOLAIR label.
You et al., High-Dose High-Frequency Aflibercept for Recalcitrant Neovascular Age-Related Macular Degeneration, Retina: Jun. 2018—38(6): 1156-1165.
Ziemssen et al., Safety of monoclonal antibodies and related therapeutic proteins for the treatment of neovascular macular degeneration: addressing outstanding issues, Expert Opin Drug Saf . Jan. 2016;15(1):75-87—Epub Dec. 11, 2015.
Brown 2008—abstract presented at Retina Society 2008.
Brown 2020—oral presentation at Angiogenesis 2020.
Chong 2009—abstract presented at EU Retina 2009.
Do 2007—abstract presented at The International Symposium of Ocular Pharmacology and Therapeutics 2007.
Heier 2009—oral presentation at The International Symposium of Ocular Pharmacology and Therapeutics 2009.
Kitchens 2015—poster presented at The 6th Controversies in Ophthalmology Congress 2015.
Nguyen 2007—oral presentation at The Association of Research in Vision and Ophthalmology 2007.
Nielsen 2020—oral presentation at American Society of Retina Specialists 2020.
Ohr et al., "Intravitreal aflibercept injection for neovascular (wet) age-related macular degeneration," informa healthcare, ISSN 1465-6566 pp. 1-7, (2012). [Expert Opin. Pharmacother. Downloaded from informahealthcare.com by IBI Circulation—Ashley Publications Ltd on Feb. 13, 2012].
Declaration of Dr. Reiner Gentz in Support of Petition for Inter Partes Review of U.S. Pat. No. 10,464,992, "VEGF Antagonist Formulations Suitable for Intravitreal Administration," Petition for Inter Partes Review; Chengdu Kanghong Biotechnology Co., Ltd. Exhibit 1003, 76 pages (2021).
RegenBase Knowledge Base, "Controls in SCI experiments," Chengdu Kanghong Biotechnology Co., Ltd. Exhibit 1034, 2 pages (Retrieved Jan. 6, 2021 from http://regenbase.org/control-groups.html).
FDA-1985-D-0033-0003, "Guideline for Submitting Documentation for the Manufacture of and Controls for Drug Products," 20 pages (Feb. 1987).
Magari, "Assessing Shelf Life Using Real-Time and Accelerated Stability Tests," BioPharm Internatonal, vol. (16), Issue (11):1-12, (Nov. 1, 2003).

| Formulations | Diffusion coefficient (cm2/sec) | Radius (nm) | % Pd |
|---|---|---|---|
| F1 (50mM Sodium Sulfate) | 3.32E-07 | 7.4 | 15.3 |
| F2 (50mM Sodium thiocyanate) | 2.98E-07 | 8.2 | 14.7 |
| F3 (50mM Sodium citrate) | 3.20E-07 | 7.7 | 16.3 |
| F4 (50mM Glycine) | 3.89E-07 | 6.3 | 18.9 |
| F5 (50mM Sodium Chloride) | 3.24E-07 | 7.6 | 13.8 |
| F6 (50mM Lysine) | 3.17E-07 | 7.7 | 13.5 |
| F7 (50mM Sodium Aspartate) | 3.32E-07 | 7.4 | 18.2 |
| F8 (50mM Sodium Glutamate) | 3.32E-07 | 7.4 | 15.0 |
| F9 (50mM Sodium citrate+50mM Arginine HCl) | 3.31E-07 | 7.4 | 14.4 |
| F10 (50mM Glycine+ 50mM Arginine HCl) | 3.31E-07 | 7.4 | 14.3 |
| F11 (50mM Sodium Aspartate+ 50mM Arginine HCl) | 3.24E-07 | 7.6 | 14.8 |
| F12 (50mM Sodium Glutamate + 50mM Arginine HCl) | 3.22E-07 | 7.6 | 13.3 |

OCT

FA

OCT

HIGH CONCENTRATION VEGF RECEPTOR FUSION PROTEIN CONTAINING FORMULATIONS

This application claims the benefit of U.S. Provisional Patent Application No. 62/813,882, filed Mar. 5, 2019; U.S. Provisional Patent Application No. 62/769,876, filed Nov. 20, 2018; U.S. Provisional Patent Application No. 62/752,127, filed Oct. 29, 2018; and U.S. Provisional Patent Application No. 62/669,506, filed May 10, 2018; each of which is herein incorporated by reference in its entirety.

TECHNICAL FIELD

Embodiments herein relate generally to high concentration VEGF receptor fusion protein containing formulations suitable for ocular administration. More particularly, embodiments herein provide liquid pharmaceutical formulations for intravitreal administration, where the formulations include more than 40 mg/ml VEGF receptor fusion protein, and show pharmaceutically acceptable potency, stability, viscosity and pH.

SEQUENCE LISTING

An official copy of the sequence listing is submitted concurrently with the specification electronically via EFS-Web as an ASCII formatted sequence listing with a file name of "10430P1-US_SEQ_LIST_ST25.txt", a creation date of May 9, 2018, and a size of about 7 KB. The sequence listing contained in this ASCII formatted document is part of the specification and is herein incorporated by reference in its entirety.

BACKGROUND OF THE INVENTION

The development of a therapeutically useful liquid formulation requires a combination of ingredients, at differing amounts, to provide a functional and stable delivery vehicle for a drug of interest. This is particularly true where the drug is a protein, and furthermore, an antibody. Antibody formulations have long presented challenges to drug developers and manufacturers, as antibody activity and administration typically require a pharmaceutically acceptable potency, osmolality, protein stability, viscosity, and proper pH. These challenges are exacerbated when the antibody is at higher concentrations in the formulation, for example, beyond 20 to 40 mg/ml, the concentration of most pharmaceutically sold antibodies.

Higher concentration antibody formulations allow for shorter injection times, smaller injection volumes, lower frequency of antibody administration, and more efficient manufacturing and storage utility. However, as noted above, the higher the antibody or protein concentration, the more difficult it is to maintain the proper activity and delivery parameters for the formulation. In particular, high concentration antibody and protein formulations often contend with increased protein aggregation and viscosity, which results in lower overall antibody or protein potency, and lower manufacturing and poorer storage stability. Because of the issues related to high concentration protein or antibody formulations, few such pharmaceutically acceptable formulations have been developed. There is a need in the art for preparing high concentration, high stability, antibody and protein formulations that include the proper potency, stability, viscosity, osmolality and pH.

One such protein in need of high concentration formulations is the vascular endothelial growth factor (VEGF) receptor fusion protein. VEGF receptor fusion proteins are used to block VEGF function in a number of ophthalmic formulations, for example, EYLEA® (Regeneron Pharmaceuticals, Inc.). High concentration VEGF receptor fusion protein containing formulations could allow for shorter ocular injection times, smaller injection volumes, fewer possible injections per administration cycle, and more efficient manufacturing and storage.

The present invention is directed toward overcoming one or more of the problems discussed above.

SUMMARY OF THE INVENTION

Various embodiments described herein encompass high concentration protein containing formulations (e.g., which are suitable for intravitreal administration), and in particular, high concentration vascular endothelial growth factor (VEGF) receptor fusion protein containing formulations. High concentration VEGF receptor fusion protein containing formulations provide a number of therapeutic and economic benefits, including, pharmaceutically acceptable potency, long term manufacturing and storage stability, and a viscosity and pH compatible with ocular injection. High concentration VEGF receptor fusion protein containing formulations also allow for reduced ocular administration volumes, a benefit for avoiding undesired effects on the limited volume of the eye.

Embodiments herein provide formulations having a VEGF receptor fusion protein, a buffer, a thermal stabilizer, a viscosity reducing agent, and a surfactant. In other embodiments, the formulations do not include a viscosity reducing agent. Formulations of the present invention have a pH and viscosity suitable for injection, and in particular, for therapeutic ocular injection.

In an embodiment of the invention, a pharmaceutical formulation of the present invention is provided having a VEGF receptor fusion protein at a concentration of at least 41 mg/ml or a concentration that contains a single dose of VEGF receptor fusion protein (which is discussed herein) in less than about 100 µl, less than about 50 µl, about 50 µl, about 57 µl, about 60 µl, about 70 µl, or about 75 µl, a buffer, optionally a thermal stabilizer and/or a viscosity reducing agent, and a surfactant, where the formulation has a pH of from about 5.0 to about 6.8 (e.g., 5.8).

In an embodiment of the invention, the VEGF receptor fusion protein concentration is about 30 mg/ml, 60 mg/ml, 114 mg/ml, 120 mg/ml or 140 mg/ml.

In an embodiment of the invention, the surfactant can be a non-ionic surfactant (e.g., about 0.02% to about 0.1%; or about 0.03% (w/v)). In an embodiment of the invention, the surfactant is a non-ionic surfactant having a polyoxyethylene moiety, for example, polysorbate 20 (PS20), polysorbate 80 (PS80), poloxamer 188, polyethylene glycol 3350 or mixtures thereof.

In an embodiment of the invention, the buffer is a histidine-based buffer (e.g., 10 mM or 20 mM), such as histidine, histidine HCl or histidine acetate; a phosphate-based buffer, such as sodium phosphate (e.g., 10 mM); an acetate-based buffer, such as sodium acetate and acetic acid, or a citrate-based buffer, such as sodium citrate or citric acid. In an embodiment of the invention, if the buffer is phosphate buffer, the pH is from about 5.7 to about 8.0, about 5.8 to about 8.0, about 5.7 to about 7.0, about 5.8 to about 7.0, about 5.9 to about 7.0 or about 6.0 to about 7.0; if the buffer is histidine buffer, the pH is from about 5.5 to about 6.5; if the buffer is citrate buffer, the pH is from about 3.0 to about 6.2 or about 5.0 to about 6.0; and if the buffer is acetate buffer, the pH is from about 3.7 to about 5.6 or about 5.0 to about 6.0.

In an embodiment of the invention, the thermal stabilizer is a sugar, such as sucrose (e.g., about 2.5%, 5% or 8%, 10% or 20% (w/v), e.g., about 2-20%), mannitol, sorbitol, or trehalose; L-proline (e.g., about 2%, 3% or 4% (w/v)); glycine (e.g., about 50 mM), glycerol, taurine (e.g., about 50 mM) or propane sulfonic acid (e.g., about 50 mM) or any combination of the above.

In some embodiments of the invention, the pharmaceutical formulations of the present invention include a viscosity reducing agent, for example, arginine hydrochloride (e.g., L-arginine monohydrochloride) (e.g., 50 mM), lysine, sodium chloride (e.g., 40 mM or 50 mM), or magnesium chloride. Alternatively, in other embodiments, the formulations of the present invention specifically exclude substantially all, if not all, viscosity reducing agents.

In an embodiment of the invention, the pharmaceutical formulations of the present invention comprise, consists of or consists essentially of the constituents in any one of formulations A-KKKK as set forth herein.

In aspects herein, the pharmaceutical formulations of the present invention may include a VEGF receptor fusion protein (e.g., aflibercept or conbercept) at a concentration of from about 41 mg/ml to about 275 mg/ml, from about 80 mg/ml to about 275 mg/ml, about 140 mg/ml to about 150 mg/ml, about 140 mg/ml to about 159 or 160 mg/ml; including about 60 mg/ml, about 80 mg/ml, about 100 mg/ml, about 113.3 mg/ml, about 114.3 mg/ml, about 120 mg/ml, about 133.3 mg/ml, about 140 mg/ml, about 150 mg/ml, about 200 mg/ml or about 250 mg/ml. In an embodiment of the invention, the formulation comprises about 40 mg/ml of the VEGF receptor fusion protein.

Some aspects of the pharmaceutical formulations of the present invention include a thermal stabilizer at a concentration of from about 2% (w/v) to about 9% (w/v) or from about 4% (w/v) to about 9% (w/v), with the proviso, that when the thermal stabilizer is taurine or propane sulfonic acid, the stabilizer is at a concentration of from about 25 mM to about 100 mM, surfactant is at a concentration of from about 0.02% (w/v) to about 0.1% (w/v) (e.g., about 0.03%), and buffer is of from about 5 mM to about 15 mM.

The VEGF receptor fusion protein can, for example:
be encoded by the nucleic acid sequence of SEQ ID NO:1 or nucleotides 79-1374 or 79-1371 of SEQ ID NO: 1;
comprise amino acids of SEQ ID NO: 2 or amino acids 27-457 or 27-458 of SEQ ID NO: 2;
comprise:
(1) a VEGFR1 component comprising amino acids 27 to 129 of SEQ ID NO:2;
(2) a VEGFR2 component comprising amino acids 130 to 231 of SEQ ID NO:2;
(3) a multimerization component ("FcΔC1(a)") comprising amino acids 232 to 457 or 458 of SEQ ID NO:2 (the C-terminal amino acids of SEQ ID NO:2, i.e., K458, may or may not be included in the VEGF receptor fusion proteins). Note that amino acids 1 to 26 of SEQ ID NO:2 are the signal sequence;
comprise an immunoglobin-like (Ig) domain 2 of a first VEGF receptor (e.g., VEGFR1) and Ig domain 3 of a second VEGF receptor (e.g., VEGFR2), optionally further including an Ig domain 4 of the second VEGF receptor (e.g., VEGFR2) and a multimerizing component (e.g., Fc domain of IgG);
be conbercept; or
be aflibercept.

```
VEGF Trap
                                                       (SEQ ID NO: 1)
atggtcagctactgggacaccggggtcctgctgtgcgcgctgctcagctgtctgcttctc acaggatctagttccggaagtgataccggtagacctttcgtagagatgtacagtgaaatc cccgaaattatacacatgactgaaggaagggagctcgtcattccctgccgggttacgtca cctaacatcactgttactttaaaaaagtttccacttgacactttgatccctgatggaaaa cgcataatctgggacagtagaaagggcttcatcatatcaaatgcaacgtacaaagaaata gggcttctgacctgtgaagcaacagtcaatgggcatttgtataagacaaactatctcaca catcgacaaaccaatacaatcatagatgtggttctgagtccgtctcatggaattgaacta tctgttggagaaaagcttgtcttaaattgtacagcaagaactgaactaaatgtggggatt gacttcaactgggaatacccttcttcgaagcatcagcataagaaacttgtaaaccgagac ctaaaaacccagtctgggagtgagatgaagaaattttttgagcaccttaactatagatggt gtaacccggagtgaccaaggattgtacacctgtgcagcatccagtgggctgatgaccaag aagaacagcacatttgtcagggtccatgaaaaggacaaaactcacacatgcccaccgtgc ccagcacctgaactcctgggggggaccgtcagtcttcctcttccccccaaaacccaaggac accctcatgatctccccggacccctgaggtcacatgcgtggtggtggacgtgagccacgaa gaccctgaggtcaagttcaactggtacgtggacggcgtggaggtgcataatgccaagaca aagccgcgggaggagcagtacaacagcacgtaccgtgtggtcagcgtcctcaccgtcctg caccaggactggctgaatggcaaggagtacaagtgcaaggtctccaacaaagccctccca gcccccatcgagaaaaccatctccaaagccaaagggcagccccgagaaccacaggtgtac
```

```
                                                     -continued
accctgccccatcccgggatgagctgaccaagaaccaggtcagcctgacctgcctggtc aaaggcttctatcccagcgacatcgccgtggagtgggagagcaatgggcagccggagaac aactacaagaccacgcctcccgtgctggactccgacggctccttcttcctctacagcaag ctcaccgtggacaagagcaggtggcagcagggggaacgtcttctcatgctccgtgatgcat gaggctctgcacaaccactacacgcagaagagcctctccctgtctccgggtaaatga
```

(SEQ ID NO: 2)
```
MVSYWDTGVLLCALLSCLLLTGSSSGSDTGRPFVEMYSEIPEIIHMTEGRELVIPCRVTS

PNITVTLKKFPLDTLIPDGKRIIWDSRKGFIISNATYKEIGLLTCEATVNGHLYKTNYLT

HRQTNTIIDVVLSPSHGIELSVGEKLVLNCTARTELNVGIDFNWEYPSSKHQHKKLVNRD

LKTQSGSEMKKFLSTLTIDGVTRSDQGLYTCAASSGLMTKKNSTFVRVHEKDKTHTCPPC

PAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDSDGSFFLYSK

LTVDKSRWQQGNVFSCSVMHEALHNHYTQKSLSLSPGK
```

AAs 1-26 = Signal Sequence

AAs 27-129 = Flt1-D2 (VEGFR1-D2)

AAs 130-231 = Flk1-D3 (VEGFR2-D3)

AAs 232-458 = FcΔC1

In another embodiment of the present invention, a container containing an aqueous solution of from about 5 mM to about 25 mM pharmaceutically acceptable buffer, from about 4% (w/v) to about 9% (w/v) of a pharmaceutically acceptable thermal stabilizer, from about 0.02% (w/v) to about 0.1% (w/v) of a pharmaceutically acceptable surfactant, and from about 41 mg/ml to about 275 mg/ml VEGF receptor fusion protein, is provided. When the thermal stabilizer includes either taurine or propane sulfonic acid, the taurine or propane sulfonic acid is at a concentration of from about 25 mM to about 100 mM. The aqueous solution has a pH of from about 5.0 to about 6.8, and can be from about 5.5 to about 6.2 (e.g., 5.8). In some aspects, the container is a vial or syringe. In other aspects, the aqueous solution does not include an inorganic salt. When the thermal stabilizer is a sugar it can be sucrose, mannitol, sorbitol or trehalose, and can be present at between about 4% (w/v) and 9% (w/v); the surfactant can be a non-ionic surfactant, and can include a polyoxyethylene moiety, such as polysorbate 20, polysorbate 80, poloxamer 188, or polyethylene glycol 3350, at a concentration of from about 0.02% to about 0.1% weight per volume (w/v), and more typically, 0.02% to about 0.04% (w/v). In an embodiment of the invention, the VEGF receptor fusion protein is encoded by the nucleic acid sequence of SEQ ID NO:1 or nucleotides 79-1374 or 79-1371 of SEQ ID NO: 1; comprises amino acids of SEQ ID NO: 2 or amino acids 27-457 or 27-458 of SEQ ID NO: 2; comprises (1) a VEGFR1 component comprising amino acids 27 to 129 of SEQ ID NO:2; (2) a VEGFR2 component comprising amino acids 130 to 231 of SEQ ID NO:2; and (3) a multimerization component ("FcΔC1(a)") comprising amino acids 232 to 457 of SEQ ID NO:2 (the C-terminal amino acids of SEQ ID NO:2, i.e., K458, may or may not be included in the VEGF receptor fusion proteins); comprises an immunoglobin-like (Ig) domain 2 of a first VEGF receptor (e.g., VEGFR1) and Ig domain 3 of a second VEGF receptor (e.g., VEGFR2), optionally further including an Ig domain 4 of the second VEGF receptor (e.g., VEGFR2) and a multimerizing component (e.g., Fc domain of IgG); is conbercept or is aflibercept.

In still other embodiments, pharmaceutical formulations of the present invention are provided having a VEGF receptor fusion protein in an aqueous vehicle, where the aqueous vehicle has a viscosity of from about 10 cP to about 15 cP at 20° C., more typically about 10 cP to about 13 cP at 20° C., and most typically from about 11 cP to about 12 cP at 20° C. (e.g., about 6.0, 7.3, 11.5 or 12.0 cP at 20° C.). In an embodiment of the invention, the viscosity is about 12 cP to about 15 cP at 20° C. The pH of the formulation can be from about 5.8 to about 6.5 (e.g., about 5.8). In some cases, the formulations do not include a viscosity reducing agent, for example, do not include arginine hydrochloride, lysine, sodium chloride, or magnesium chloride. In other cases, the formulations include 10 mM histidine hydrochloride or 10 mM histidine-acetate. The sugar can be sucrose, mannitol, sorbitol or trehalose, and can be present at between about 4% (w/v) and 9% (w/v) (e.g., about 5%); the surfactant can be a non-ionic surfactant, and can include a polyoxyethylene moiety, such as polysorbate 20, polysorbate 80, poloxamer 188, or polyethylene glycol 3350, at a concentration of from about 0.02% to about 0.1% weight per volume (w/v), and more typically, 0.02% to about 0.04% (w/v) (e.g., 0.03%). In addition, the formulation can additionally include a thermal stabilizer selected from either taurine or propane sulfonic acid at a concentration of between about 25 mM to about 100 mM, and more typically about, 50 mM to about 70 mM. In an embodiment of the invention, a formulation comprises VEGF receptor fusion protein, such as aflibercept, (e.g., at a concentration of about 41-275 mg/ml, about 50 mg/ml, about 100 mg/ml, about 115 mg/ml, about 125 mg/ml, about 150 mg/ml, about 200 mg/ml or any of the "high" concentrations discussed herein), about 10 mM histidine-based buffer, about 5% (w/v) sucrose, about 0.03% (w/v) non-ionic surfactant such as polysorbate e.g., polysorbate 20, and about 50 mM arginine, L-arginine or L-arginine monohydrochloride, with a pH of about 5.8. In an embodiment of the invention, the VEGF receptor fusion protein is encoded by the nucleic acid sequence of SEQ ID NO:1 or nucleotides 79-1374 or 79-1371 of SEQ ID NO: 1; comprises amino acids of SEQ ID NO: 2 or amino acids 27-457 or 27-458 of SEQ ID NO: 2; comprises (1) a VEGFR1 component comprising amino acids 27 to 129 of SEQ ID NO:2; (2) a VEGFR2 component comprising amino acids 130 to 231 of SEQ ID NO:2; and (3) a multimerization component ("FcΔC1(a)") comprising amino acids 232 to 457 of SEQ ID NO:2 (the C-terminal amino acids of SEQ ID NO:2, i.e., K458, may or may not be included in the VEGF receptor fusion proteins); comprises an immunoglobin-like (Ig) domain 2 of a first VEGF receptor (e.g., VEGFR1) and Ig domain 3 of a second VEGF receptor (e.g., VEGFR2), optionally further including an Ig domain 4 of the second VEGF receptor (e.g., VEGFR2) and a multimerizing component (e.g., Fc domain of IgG); is conbercept or is aflibercept.

In yet another embodiment, a pharmaceutical formulation of the present invention is provided that includes a VEGF receptor fusion protein at a concentration of from about 80 mg/ml to about 275 mg/ml in a pharmaceutically acceptable buffer. In some cases, the stable pharmaceutical formulations can also include taurine or propane sulfonic acid. The formulations can be stable at a temperature of about 2° C. to about 8° C. for about 24-36 months. In some cases, the VEGF receptor fusion protein shows less than about a 5% increase in high molecular weight species, and more typically, less than about 4.5% increase in high molecular weight species, less than about 4.0% increase in high molecular weight species, less than about 3.5% increase in high molecular weight species, less than about 3.0% increase in high molecular weight species, less than about 2.5% increase in high molecular weight species, less than about 2.0 increase in high molecular weight species and/or less than about 1.5% increase in high molecular weight species, when stored at these temperatures and for this amount of time. In other cases, the VEGF receptor fusion protein shows less than a 2.0% to 3.0% increase in high molecular weight species when the formulations are stored at these temperatures and for this amount of time.

Embodiments herein can also include pharmaceutical formulations of the present invention that include aflibercept, a pH buffered solution, a sugar and a surfactant, where the aflibercept is at a concentration of 41 mg/ml to about 275 mg/ml. Alternatively, embodiments can be stable liquid pharmaceutical formulations that include conbercept, a pH buffered solution, a sugar and a surfactant, where the conbercept is at a concentration of 41 mg/ml to about 275 mg/ml. Stable liquid pharmaceutical formulations can also include taurine or propane sulfonic acid. In some aspects, the aflibercept or conbercept is at a concentration of either 80 mg/ml or 150 mg/ml. In other aspects, the formulations do not include an inorganic salt, sodium chloride for example.

Some embodiments are directed to sterile syringes such that the syringes are pre-filled with an aqueous solution having 80 mg/ml aflibercept, conbercept, 10 mM histidine hydrochloride, histidine acetate or sodium phosphate, 5% (w/v) sucrose, mannitol, sorbitol or trehalose, 0.03% (w/v) polysorbate 20, polysorbate 80, poloxamer 188, or polyethylene glycol 3350, and 40 mM sodium chloride. Aspects herein include the further addition of about 25 mM to about 100 mM, and more typically about 50 mM to about 70 mM, of either taurine or propane sulfonic acid. In some aspects, the syringes are pre-filled with an aqueous solution having 80 mg/ml aflibercept, conbercept, 10 mM histidine HCl, histidine acetate or sodium phosphate, 8% (w/v) sucrose, mannitol, sorbitol or trehalose, and 0.03% (w/v) polysorbate 20, polysorbate 80, poloxamer 188, or polyethylene glycol 3350. Aspects herein include the further addition of about 25 mM to about 100 mM, and more typically about 50 mM to about 70 mM, of either taurine or propane sulfonic acid. In still other aspects, the syringes are pre-filled with an aqueous solution having 150 mg/ml aflibercept, conbercept, 10 mM histidine hydrochloride, histidine acetate, or sodium phosphate, 5% (w/v) sucrose, mannitol, sorbitol or trehalose, 0.03% (w/v) polysorbate 20, polysorbate 80, poloxamer 188, or polyethylene glycol 3350 and 40 mM sodium chloride, with a pH of about 6.2. Aspects herein can include the further addition of either taurine or propane sulfonic acid. In yet still other aspects, the syringes are pre-filled with an aqueous solution having 150 mg/ml aflibercept, conbercept, 10 mM histidine hydrochloride, histidine acetate, or sodium phosphate, 8% (w/v) sucrose, mannitol, sorbitol or trehalose, and 0.03% (w/v) polysorbate 20, polysorbate 80, poloxamer 188, or polyethylene glycol 3350, with a pH of about 6.2 and the aqueous solution does not include an inorganic salt. Aspects can further include about 25 mM to about 100 mM, and more typically, about 50 mM to about 70 mM, of either taurine or propane sulfonic acid. In yet still other aspects, the syringes are pre-filled with an aqueous solution having 150 mg/ml aflibercept or conbercept, 10 mM sodium acetate or acetic acid, 5% (w/v) glycerol and 0.03% (w/v) polysorbate 20, polysorbate 80, poloxamer 188, or polyethylene glycol 3350 and 40 mM sodium chloride, with a pH of about 6.2. In yet still other aspects, the syringes are pre-filled with an aqueous solution having 150 mg/ml aflibercept or conbercept, 10 mM sodium acetate or acetic acid, 8% (w/v) glycerol, and 0.03% (w/v) polysorbate 20, polysorbate 80, poloxamer 188, or polyethylene glycol 3350 and 40 mM sodium chloride, with a pH of about 6.2.

The present invention also provides a method for making any formulation set forth herein comprising the step of combining each component of the formulation into a single composition. Such a method may include the step of adding the resulting formulation into a vial or injection device. Any composition that is the product of such a method also forms part of the present invention. For example, embodiments herein also include methods for preparing a formulation by combining a histidine-based, citrate-based, acetate-based or phosphate-based buffer, with sucrose, polysorbate 20 and a VEGF receptor fusion protein; and, optionally, one or more additional components, e.g., as discussed herein. In some cases, the formulation is prepared to also include taurine or propane sulfonic acid, but where it does not include taurine or propane sulfonic acid, it may also not include an inorganic salt. In aspects herein, the sucrose is at a weight per volume of from about 4% to about 10%, the polysorbate 20 has a weight per volume of about 0.02% to about 0.1%, and the receptor fusion protein is at a concentration of from about 41 mg/ml to about 275 mg/ml. Where the formulation includes taurine or propane sulfonic acid, it is present at, for example, about 25 mM to about 100 mM, but may also be included at 50 mM to 70 mM. The method can include loading a predetermined volume of prepared formulation into a sterile syringe, such that the volume has a 0.1 mg to 10 mg dose of the VEGF receptor fusion protein.

The present invention also provides a method for administering a formulation of the present invention to a subject (e.g., a human) comprising intraocularly injecting (e.g., intravitreal injection) the formulation into the eye of the subject. The present invention also provides a method for administering a formulation of the present invention to a subject (e.g., a human) comprising implanting an intravitreal implant that contains a formulation of the present invention into the vitreous of the subject.

Embodiments herein also include methods for treating an angiogenic eye disorder, e.g., age-related macular degeneration (wet), macular edema following retinal vein occlusion, retinal vein occlusion (RVO), central retinal vein occlusion (CRVO) branch retinal vein occlusion (BRVO), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy or diabetic retinopathy (e.g., non-proliferative diabetic retinopathy and/or proliferative diabetic retinopathy) in a subject in need thereof by intraocularly injecting at least about 2 mg (e.g., 4 mg, 6 mg or 8 mg) of VEGF receptor fusion protein (e.g., aflibercept or conbercept) into the eye of a subject in need thereof, for example, any formulation set forth herein. In an embodiment of the invention, the injection volume is 100 microliters or less (e.g., 100 microliters, 50 microliters or 57 microliters). The method comprises an intravitreal injection of a pre-mixed aqueous solution having a VEGF receptor fusion protein at a concentration of from 41 mg/ml to about 275 mg/ml, a pharmaceutically acceptable sugar, a pharmaceutically acceptable buffer, and a pharmaceutically acceptable surfactant. Treatment methods using the pre-mixed aqueous solution do not require dilution. In aspects herein, the pre-mixed aqueous solution has a pH from about 6.0 and about 6.5, and has a viscosity of between about 10 cP and 13 cP.

In aspects of the treatment method, the VEGF receptor fusion protein comprises VEGFR1R2-FcΔC1(a) encoded by the nucleic acid sequence of SEQ ID NO:1, amino acids 27 to 129 of SEQ ID NO:2, a VEGFR2 component comprising amino acids 130 to 231 of SEQ ID NO:2, or a multimerization component comprising amino acids 232 to 457 of SEQ ID NO:2, or any combination thereof. In an embodiment of the invention, the VEGF receptor fusion protein is aflibercept or conbercept.

Other embodiments in accordance with the disclosure herein will become apparent from a review of the ensuing detailed description.

BRIEF DESCRIPTION OF THE DRAWINGS

The above and other aspects, features and advantages of embodiments disclosed herein will become more apparent to those of ordinary skill in the art with reference to the accompanying drawings.

(326-OS and 329-OD) before administration of aflibercept (OD=oculus dexter (right eye); OS=oculus sinister (left eye)).

TABLE A

Formulations F1-F12.

| Formulation # | VEGF Trap (mg/mL) | Buffer | Other Excipients | Screening Excipients (mM) |
|---|---|---|---|---|
| F1 (GGG) | 140 | 20 mM Histidine, pH 5.8 | 5% Sucrose, 0.03% Polysorbate 20 | 50 mM Sodium sulfate |
| F2 (HHH) | 140 | 20 mM Histidine, pH 5.8 | 5% Sucrose, 0.03% Polysorbate 20 | 50 mM Sodium thiocyanate |
| F3 (III) | 140 | 20 mM Histidine, pH 5.8 | 5% Sucrose, 0.03% Polysorbate 20 | 40 mM Sodium citrate |
| F4 (JJJ) | 140 | 20 mM Histidine, pH 5.8 | 5% Sucrose, 0.03% Polysorbate 20 | 50 mM Glycine |
| F5 (KKK) | 140 | 20 mM Histidine, pH 5.8 | 5% Sucrose, 0.03% Polysorbate 20 | 50 mM Sodium chloride |
| F6 (LLL) | 140 | 20 mM Histidine, pH 5.8 | 5% Sucrose, 0.03% Polysorbate 20 | 50 mM Lysine |
| F7 (MMM) | 140 | 20 mM Histidine, pH 5.8 | 5% Sucrose, 0.03% Polysorbate 20 | 50 mM Sodium aspartate |
| F8 (NNN) | 140 | 20 mM Histidine, pH 5.8 | 5% Sucrose, 0.03% Polysorbate 20 | 50 mM Sodium glutamate |
| F9 (OOO) | 140 | 20 mM Histidine, pH 5.8 | 5% Sucrose, 0.03% Polysorbate 20 | 50 mM Sodium Citrate + 50 mM Arginine hydrochloride |
| F10 (PPP) | 140 | 20 mM Histidine, pH 5.8 | 5% Sucrose, 0.03% Polysorbate 20 | 50 mM Glycine + 50 mM Arginine hydrochloride |
| F11 (QQQ) | 140 | 20 mM Histidine, pH 5.8 | 5% Sucrose, 0.03% Polysorbate 20 | 50 mM Sodium aspartate + 50 mM Arginine hydrochloride |
| F12 (RRR) | 140 | 20 mM Histidine, pH 5.8 | 5% Sucrose, 0.03% Polysorbate 20 | 50 mM Sodium glutamate + 50 mM Arginine hydrochloride |

Figure 10:
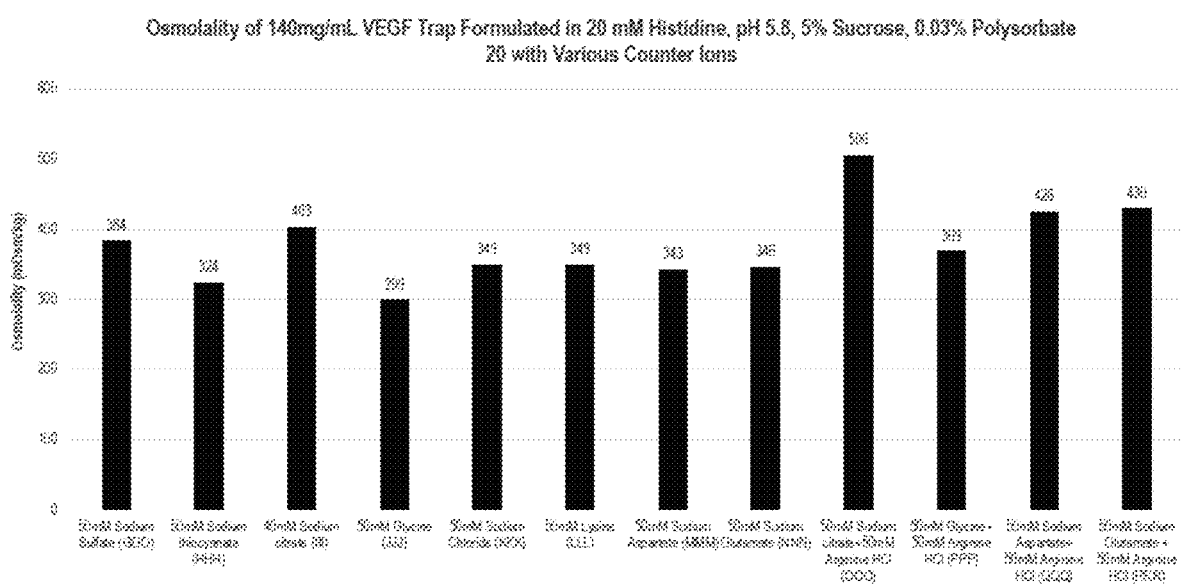

FIG. 10 shows the osmolality (mmol/Kg) of Formulations F1-F12 (set forth in Table A herein).

Figure 11A:
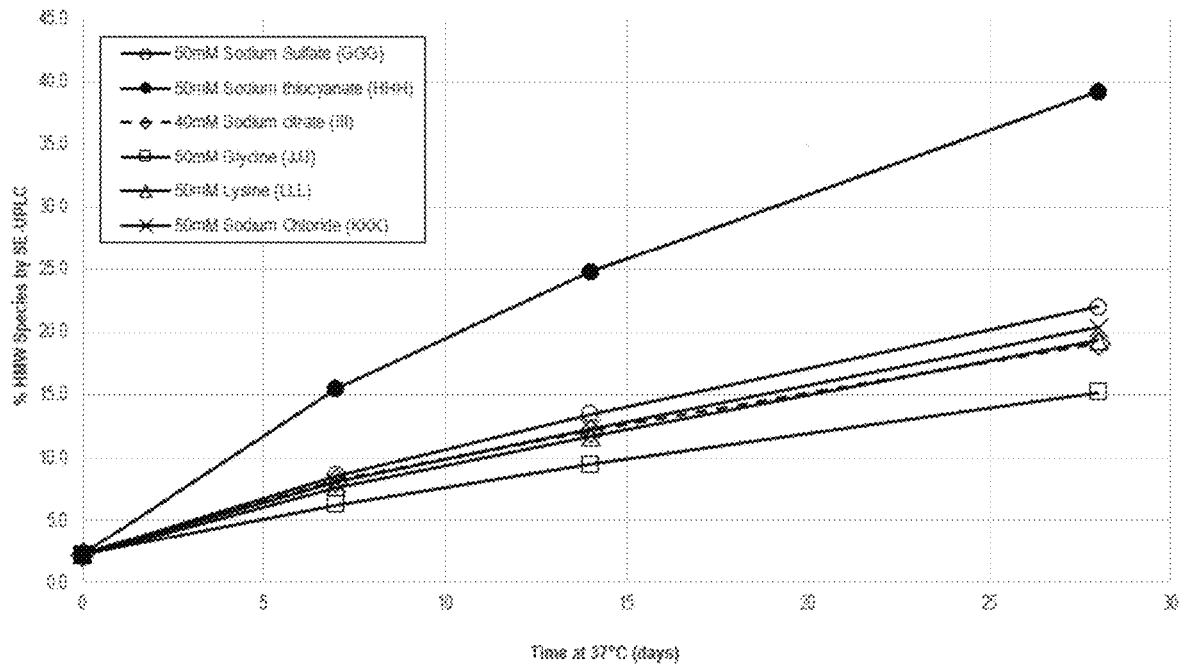
Figure 11B:
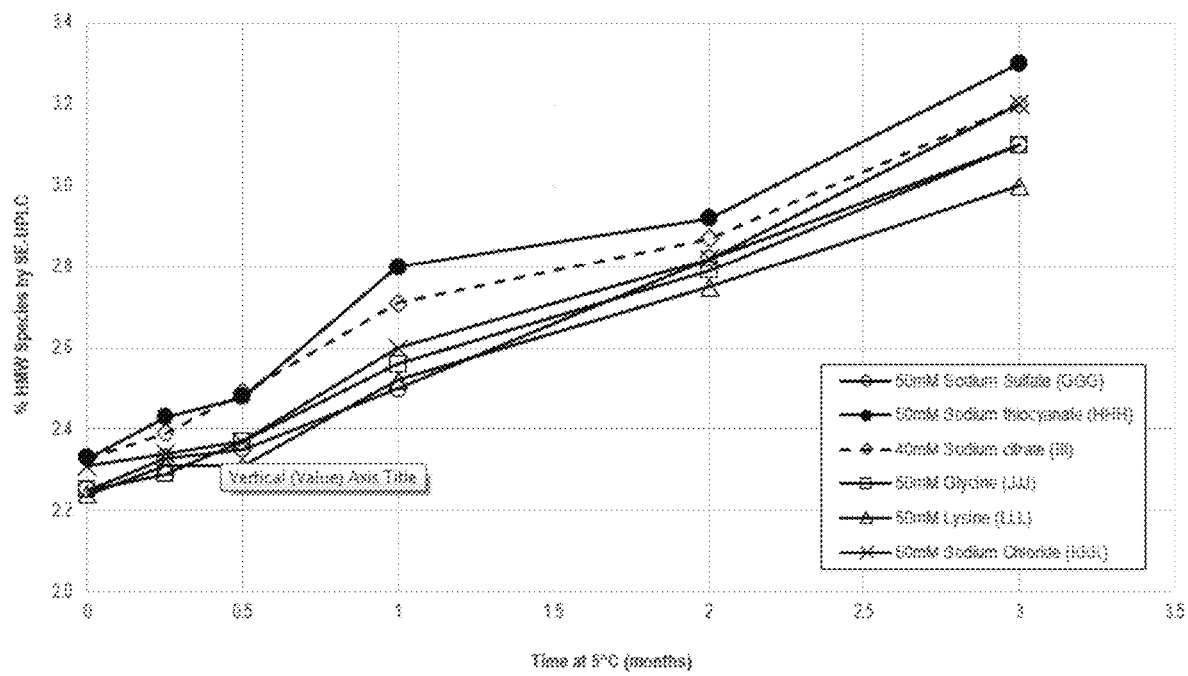
Figure 13A:
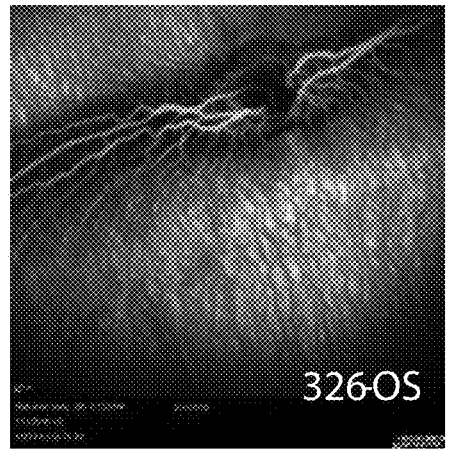
(FIG. 13A) FA image for rabbit 326, left eye.
Figure 13B:
(FIG. 13B) OCT image for rabbit 326, left eye.
Figure 13C:
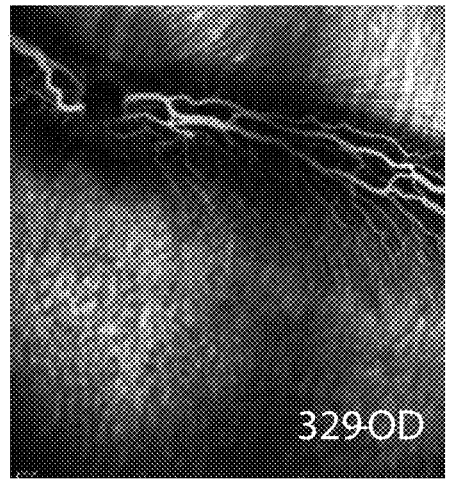
(FIG. 13C) FA image for rabbit 329, right eye.
Figure 13D:
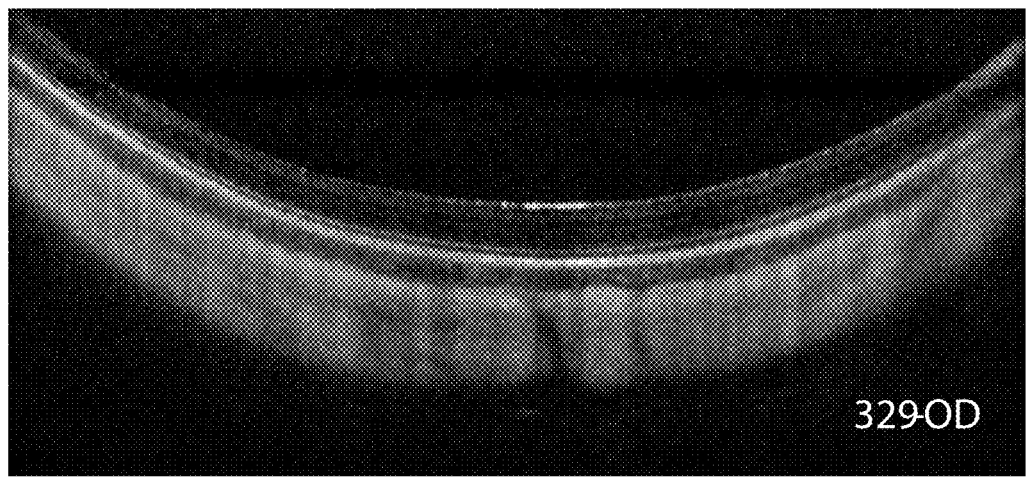
(FIG. 13D) OCT image for rabbit 329, right eye.
Figure 14A:
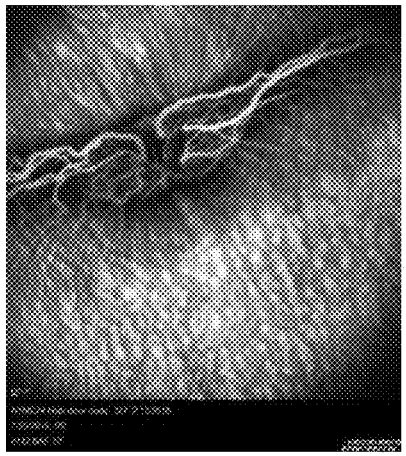
FIGS. 14A, 14B, 14C, 14D, 14E and 14F show a time course of rabbit FA images at days 1 (FIG. 14A), 7 (FIG. 14B) and 14 (FIG. 14C) and the OCT at days 1 (FIG. 14D), 7 (FIG. 14E) and 14 (FIG. 14F) for one rabbit (326-OS) administered the histidine buffer formulation (30 degree lens) (7 mg/eye).
Figure 14B:
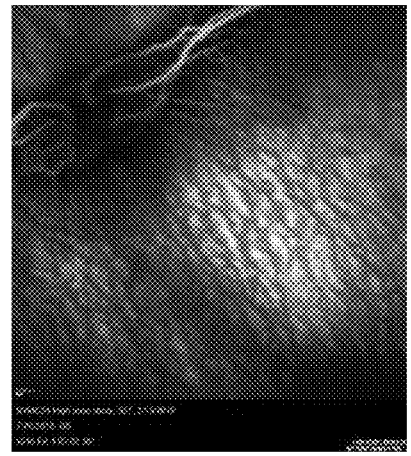
Figure 14C:
Figure 14D:
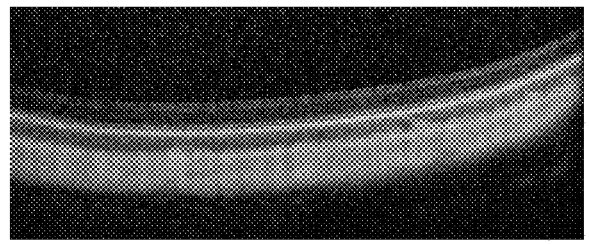
Figure 14E:
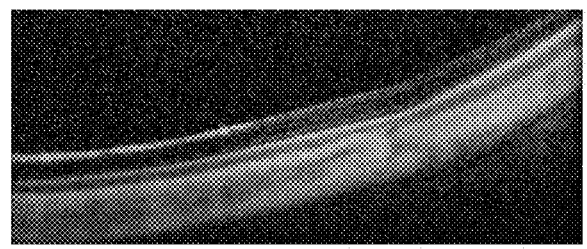
Figure 14F:
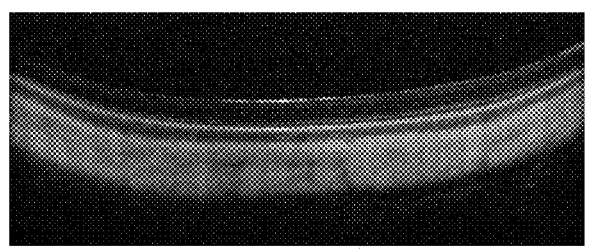
Figure 15A:
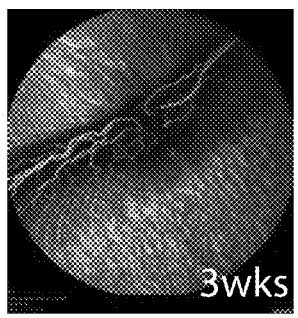
FIGS. 15A, 15B, 15C, 15D, 15E, 15F, 15G and 15H show a time course of rabbit FA images at 3 weeks (FIG. 15A), 4 weeks (FIG. 15B), 7 weeks (FIG. 15C) and 8 weeks (FIG. 15D); and the OCT at 3 weeks (FIG. 15E), 4 weeks (FIG. 15F), 7 weeks (FIG. 15G) and 8 weeks (FIG. 15H) for one
Figure 15B:
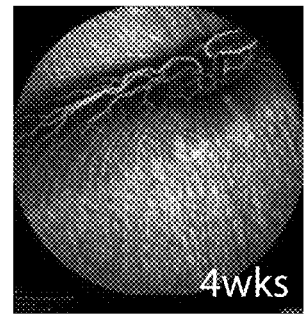
Figure 15C:
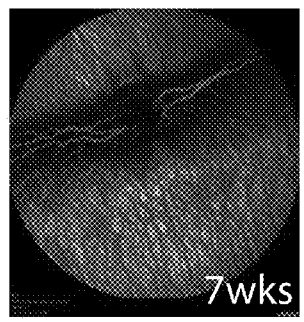
Figure 15D:
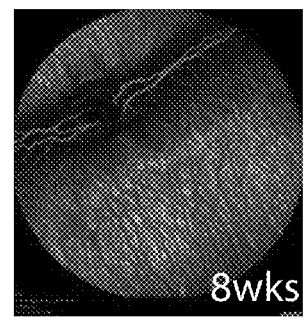
Figure 15E:
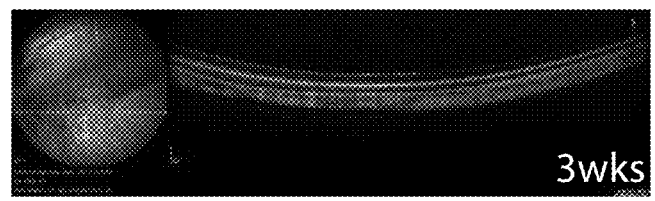
Figure 15F:
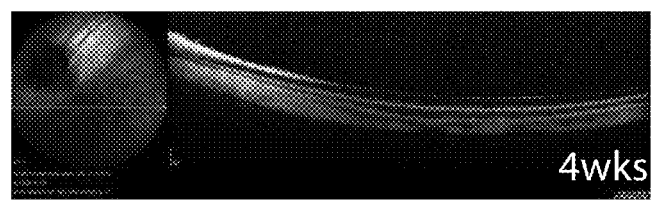
Figure 15G:
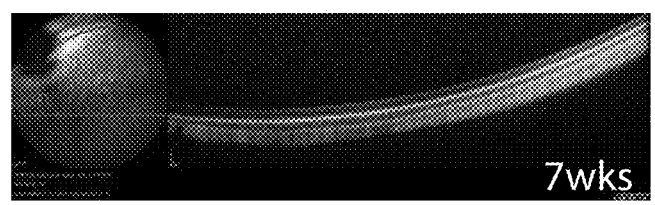
Figure 15H:
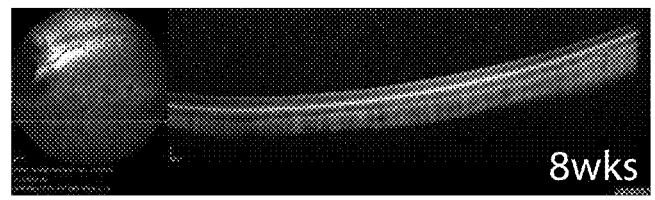
Figure 16A:
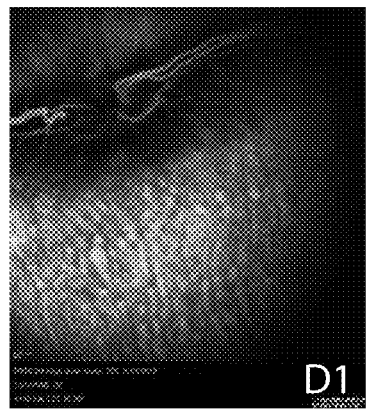
Figure 16B:
Figure 16C:
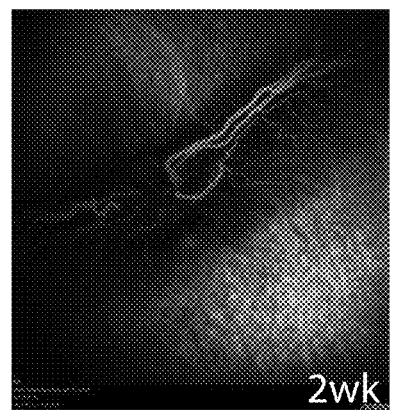
Figure 16D:
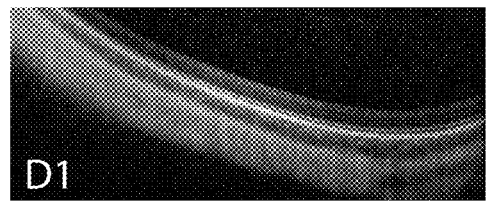
Figure 16E:
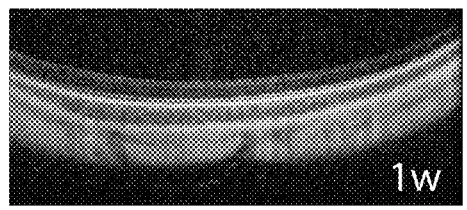
Figure 16F:
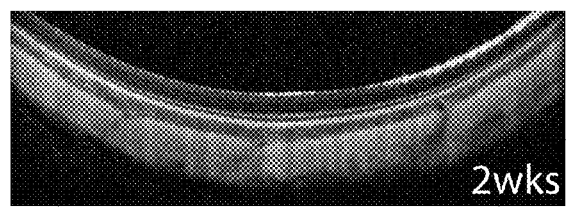
Figure 17A:
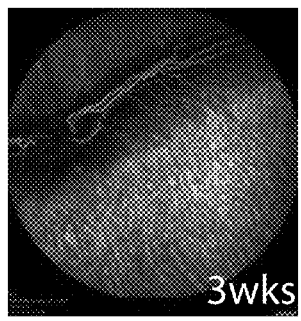
Figure 17B:
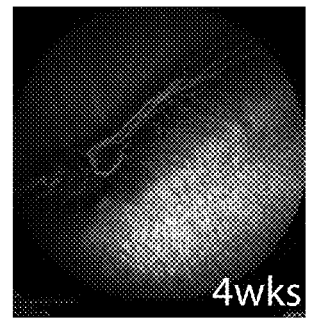
Figure 17C:
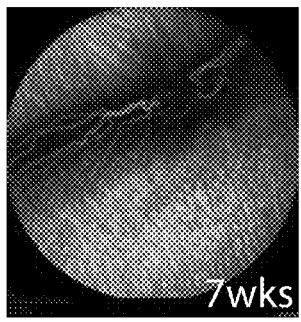
Figure 17D:
Figure 17E:
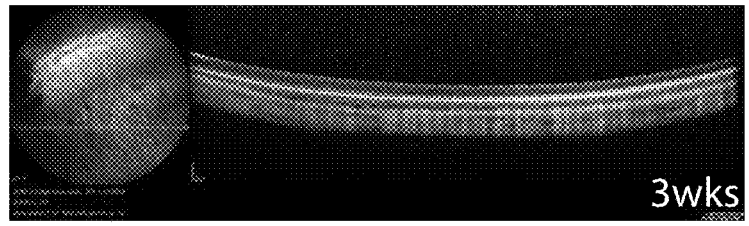
Figure 17F:
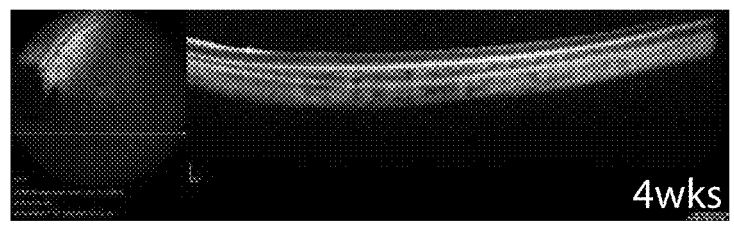
Figure 17G:
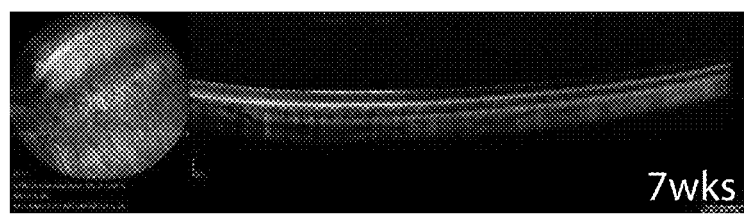
Figure 17H:
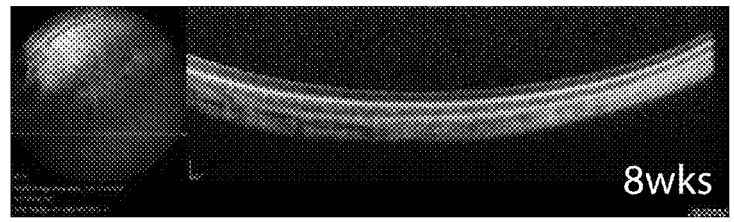

FIGS. 11A and 11B measure the percentage of high molecular weight species in formulations F1-F6 (Formulations GGG, HHH, III, JJJ, LLL and KKK) over time, by SE-UPLC, after storage at 37° C. for up to 28 days (FIG. 11A) or 5° C. for up to 3 months (FIG. 11B) over time.

FIG. 12 shows the dynamic light scattering (diffusion coefficient (cm$^2$/second), radius (nm) and % Pd) at the initial time point of the formulations shown in Table 9-3 (GGG-RRR).

FIGS. 13A, 13B, 13C and 13D show the baseline FA images and OCT (30 degree lens) for two different rabbits rabbit (326-OS) administered the histidine buffer formulation (55 degree lens) (7 mg/eye).

FIGS. 16A, 16B, 16C, 16D, 16E and 16F show a time course of rabbit FA images at day 1 (FIG. 16A), week 1 (FIG. 16B) and week 2 (FIG. 16C) and the OCT at day 1 (FIG. 16D), week 1 (FIG. 16E) and week 2 (FIG. 16F) for one rabbit (329-OS) administered the phosphate buffer formulation (30 degree lens) (7 mg/eye).

FIGS. 17A, 17B, 17C, 17D, 17E, 17F, 17G and 17H show a time course of rabbit FA images at week 3 (FIG. 17A), week 4 (FIG. 17B), week 7 (FIG. 17C) and week 8 (FIG. 17D) and the OCT at week 3 (FIG. 17E), week 4 (FIG. 17F), week 7 (FIG. 17G) and week 8 (FIG. 17H) for one rabbit (329-OS) administered the phosphate buffer formulation (55 degree lens) (7 mg/eye).

Figure 18A:
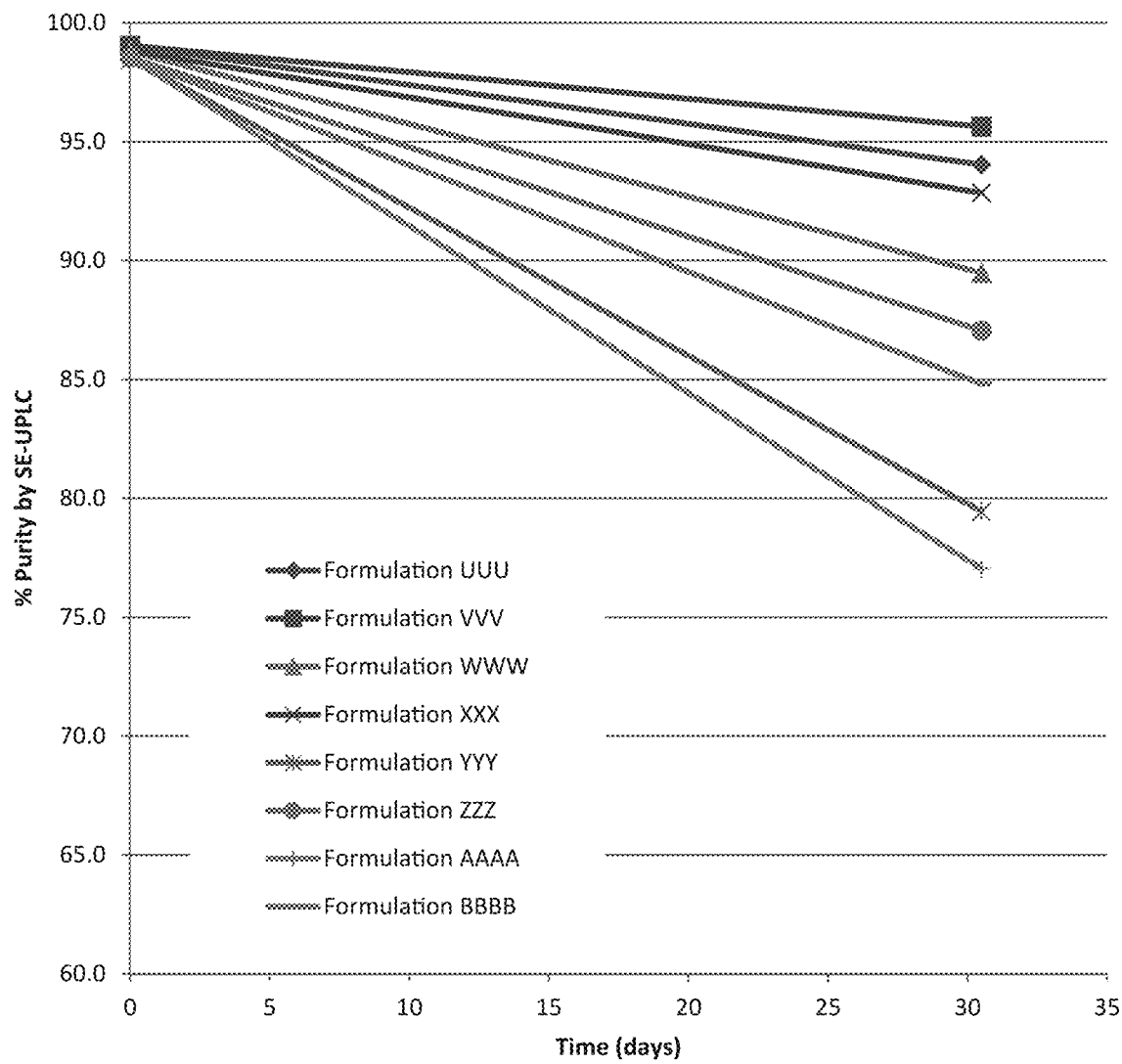
Figure 18B:
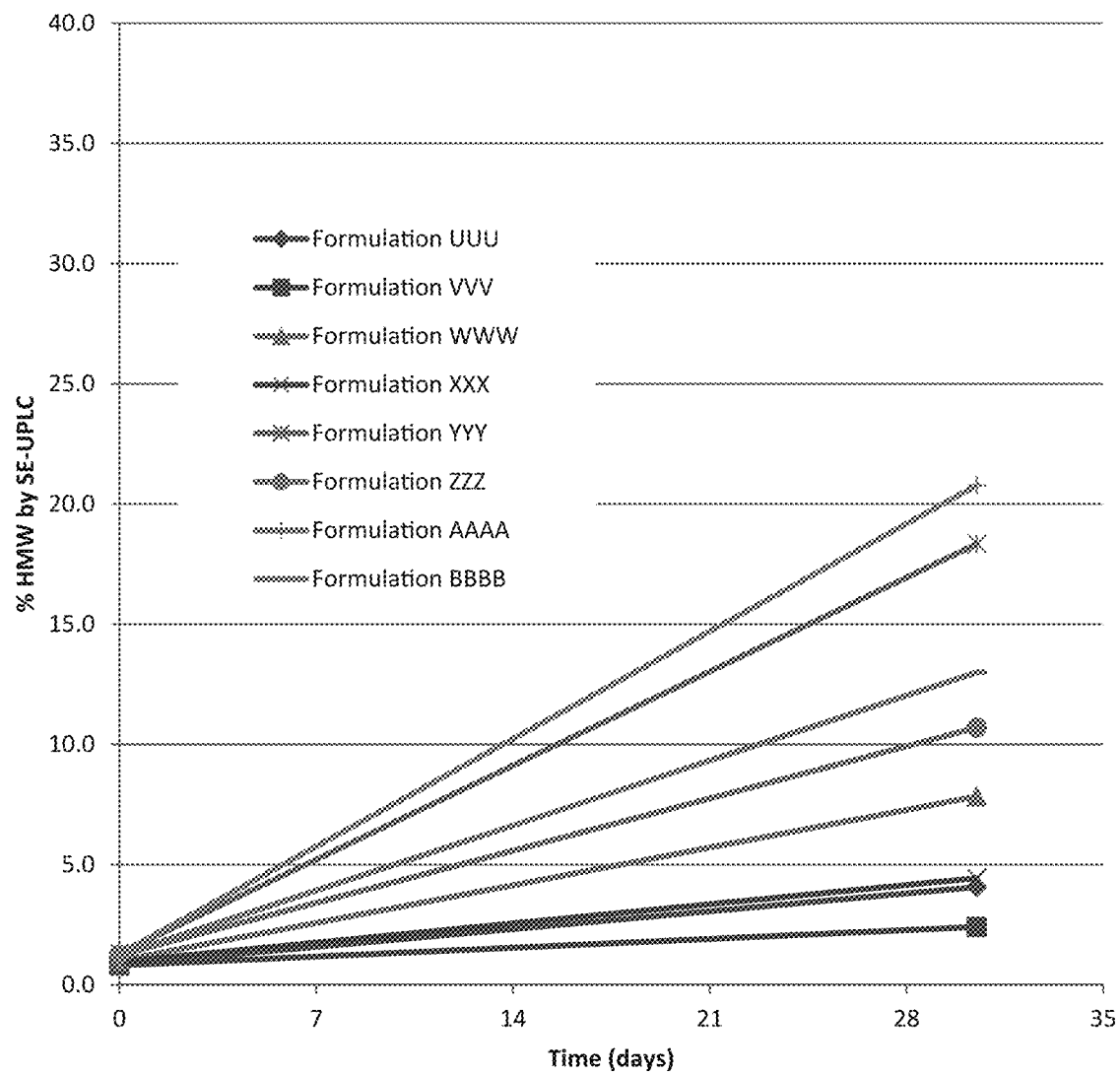

FIGS. 18A and 18B show the purity (percentage of native species) (FIG. 18A) and percentage of high molecular weight (HMW) species (FIG. 18B) in formulations UUU-BBBB over time at 37° C. (up to one month) (see Table 11-1) as analyzed by SE-UPLC.

Figure 19A:
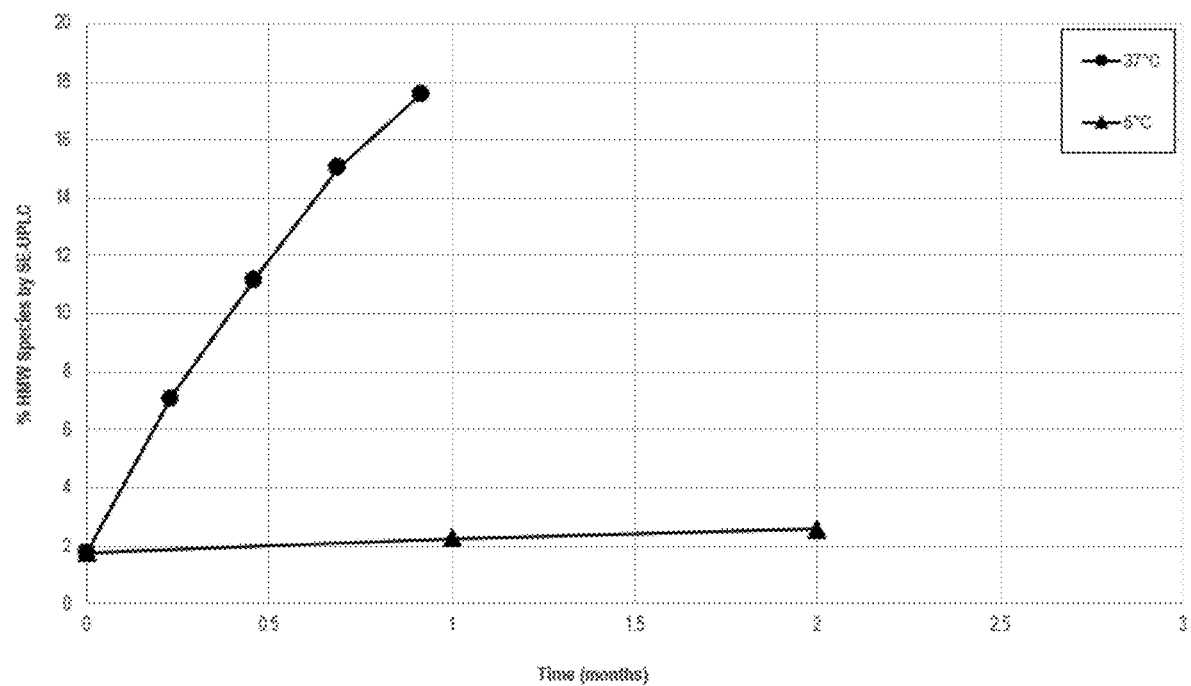
Figure 19B:
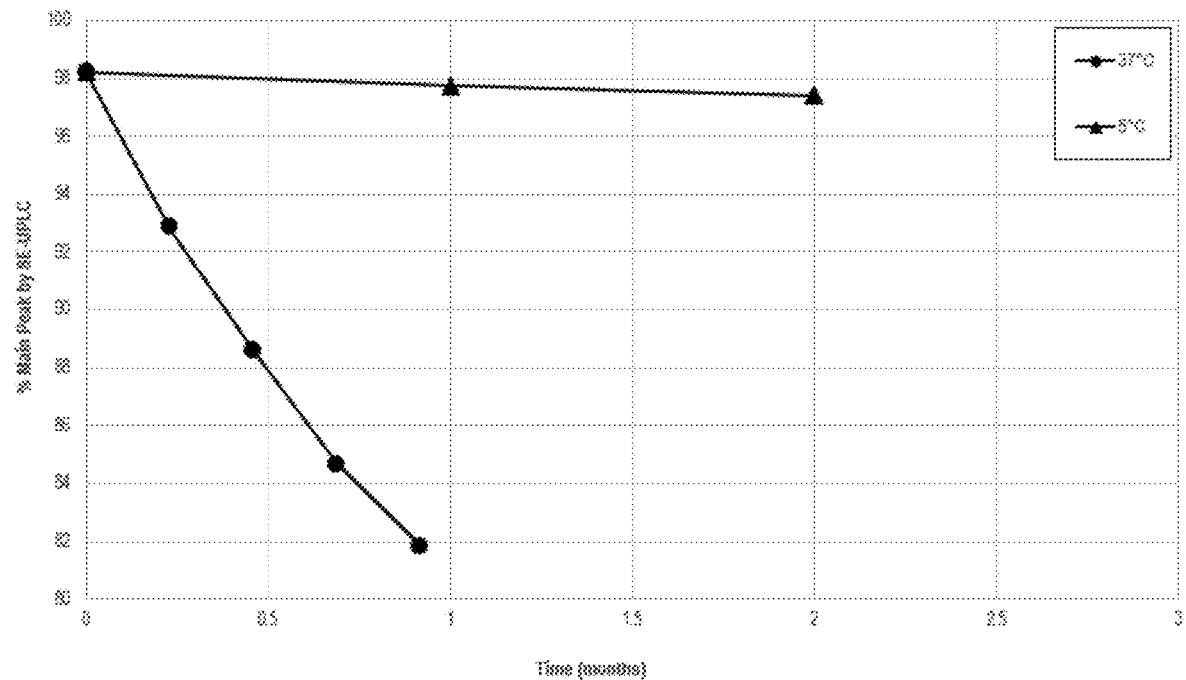
Figure 19C:
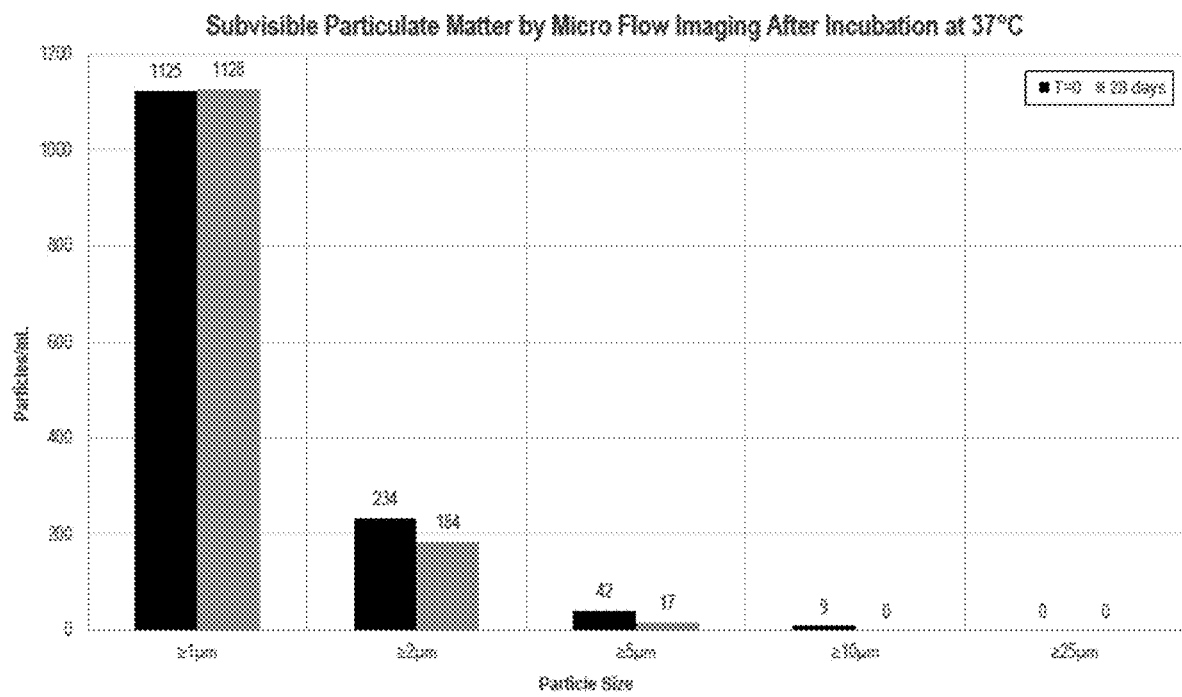
Figure 19D:
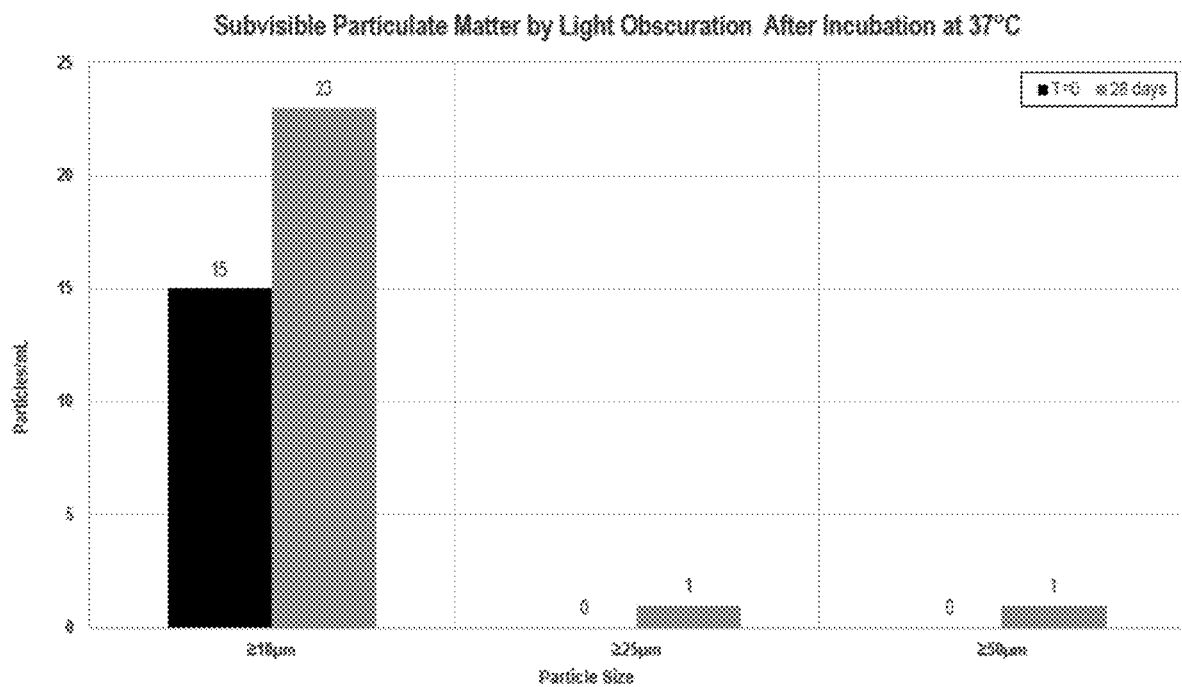
Figure 19E:
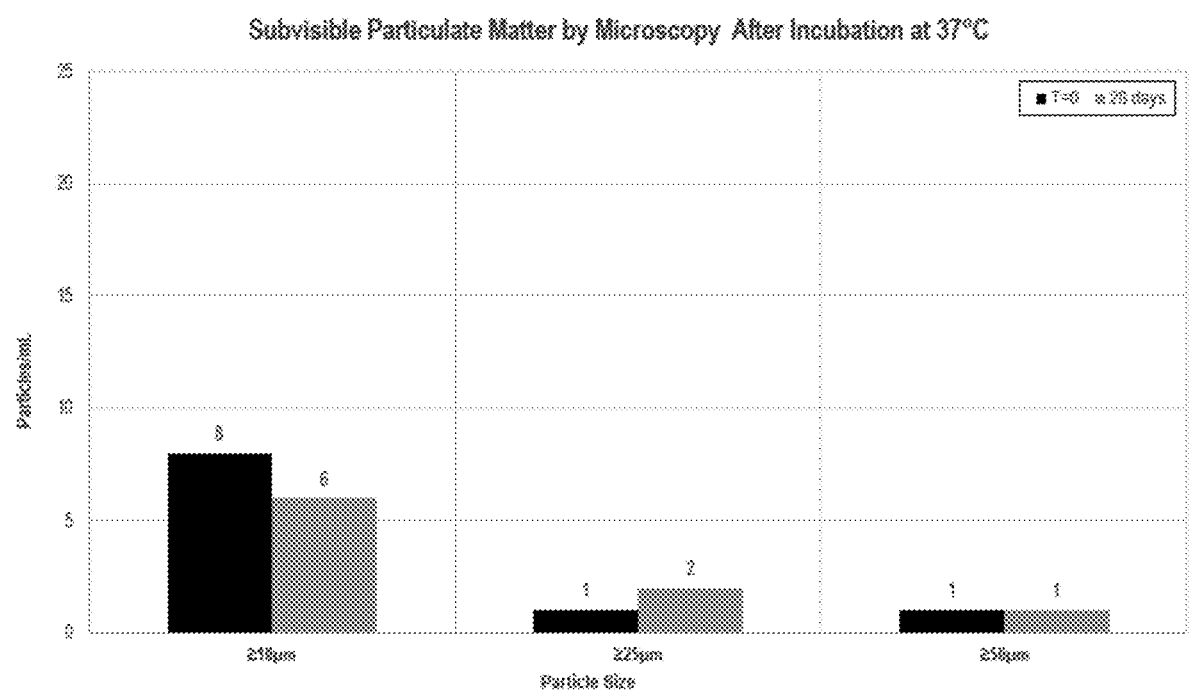

FIGS. 19A, 19B, 19C, 19D and 19E show stability and purity analysis of a formulation having 114.3 mg/mL VEGF Trap (aflibercept) formulated in 10 mM Histidine, pH 5.8, 5% Sucrose, 0.03% Polysorbate 20, 50 mM Arginine Monohydrochloride by size exclusion chromatographic determination of the percentage of (i) high molecular weight species (HMW) after incubation at 5° C. or 37° C. for up to 2 months (FIG. 19A) and (ii) main species (Main peak) after incubation at 5° C. or 37° C. for up to 2 months (FIG. 19B); as well as by microflow imaging to determine the presence of subvisible particulate matter after incubation at 37° C. for up to 28 days (FIG. 19C), by particle light obscuration analysis to determine the presence of subvisible particulate matter after incubation at 37° C. for up to 28 days (FIG. 19D), and by microscopic determination of subvisible particulate matter after incubation at 37° C. for up to 28 days (FIG. 19E).

Figure 20A:
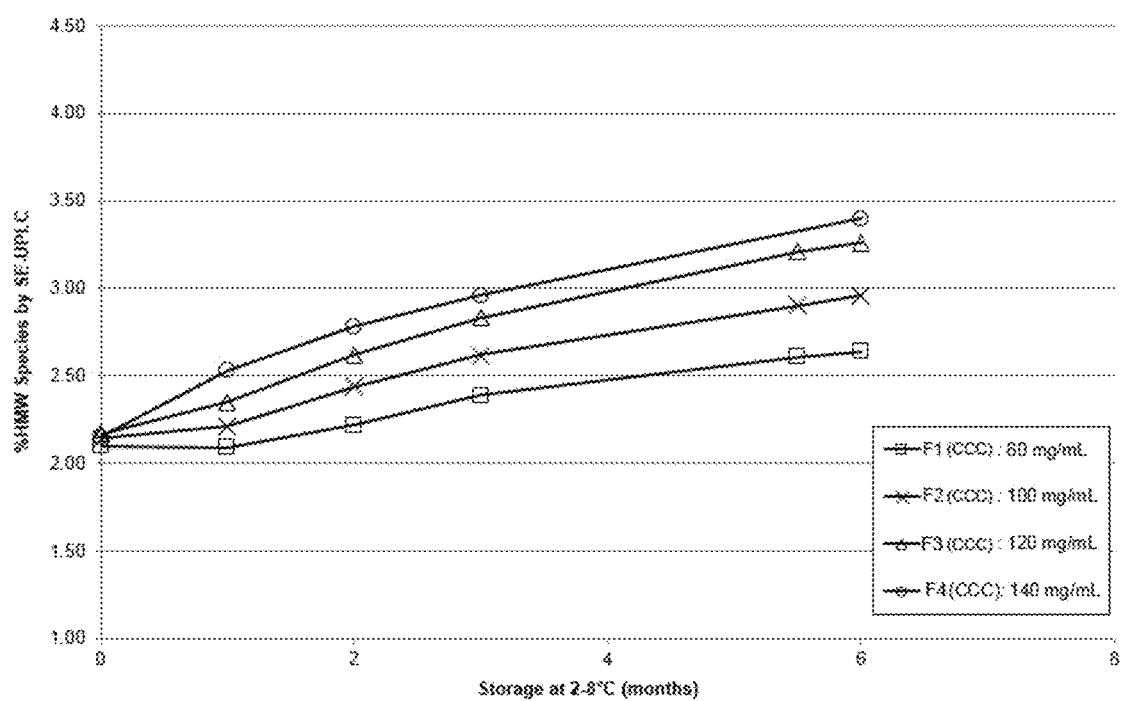
Figure 20B:
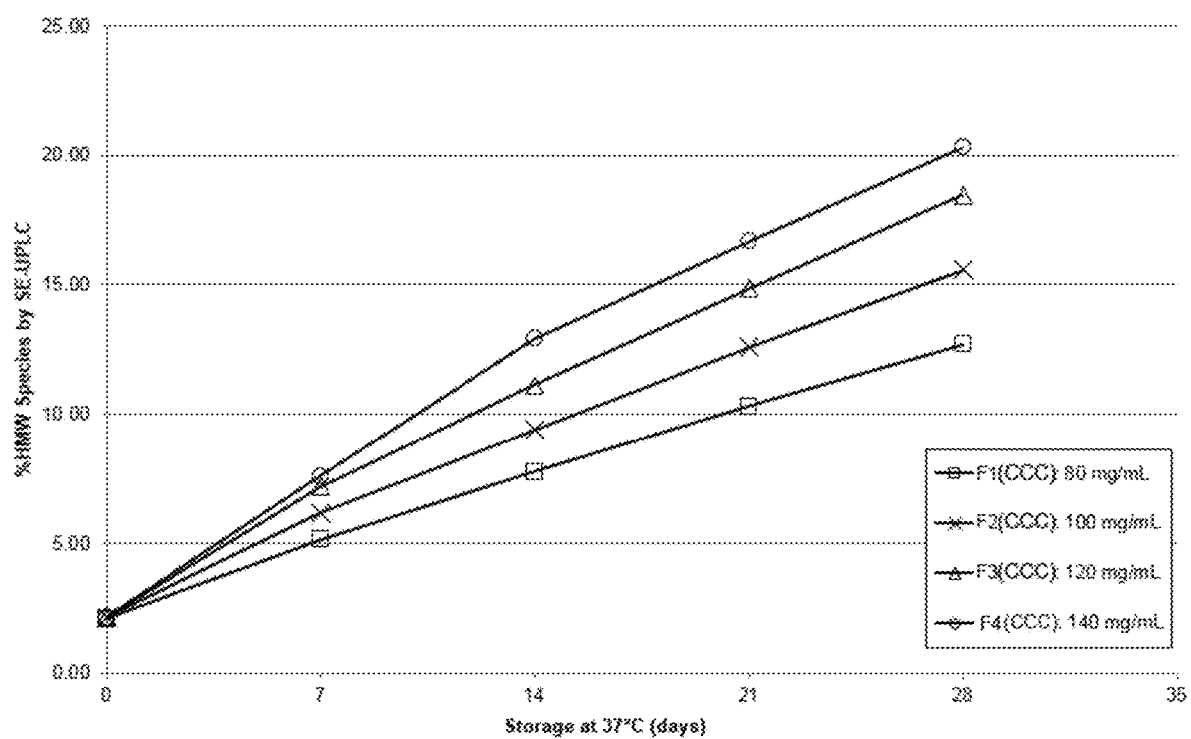

FIGS. 20A and 20B show stability and purity analysis of formulation CCC, having 80, 100, 120 or 140 mg/ml aflibercept, by SE-UPLC determination of the percentage of high molecular weight species (HMW) after incubation at 2-8° C. for up to 6 months (FIG. 20A) or 37° C. for up to 28 days (FIG. 20B).

Figure 21:
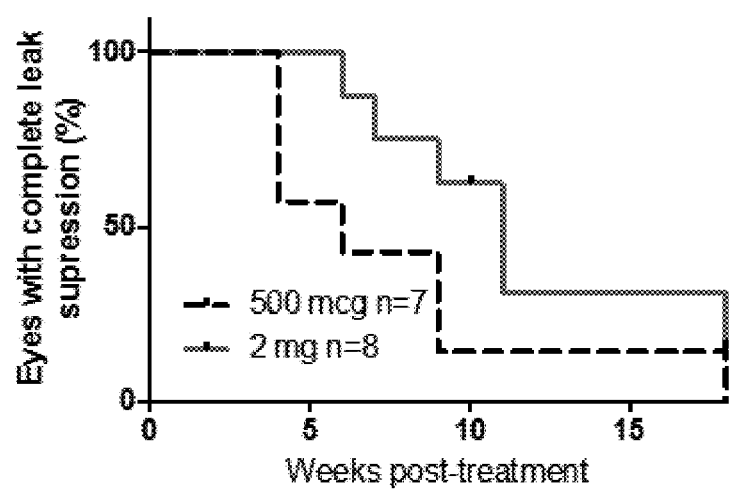

FIG. 21 shows the percentage of eyes in rabbits tested with complete leak suppression over time, when administered 500 micrograms or 2 mg aflibercept, over time (Gehan-Breslow-Wilcoxon test (P 0.0453)).

DETAILED DESCRIPTION

Figure 8A:
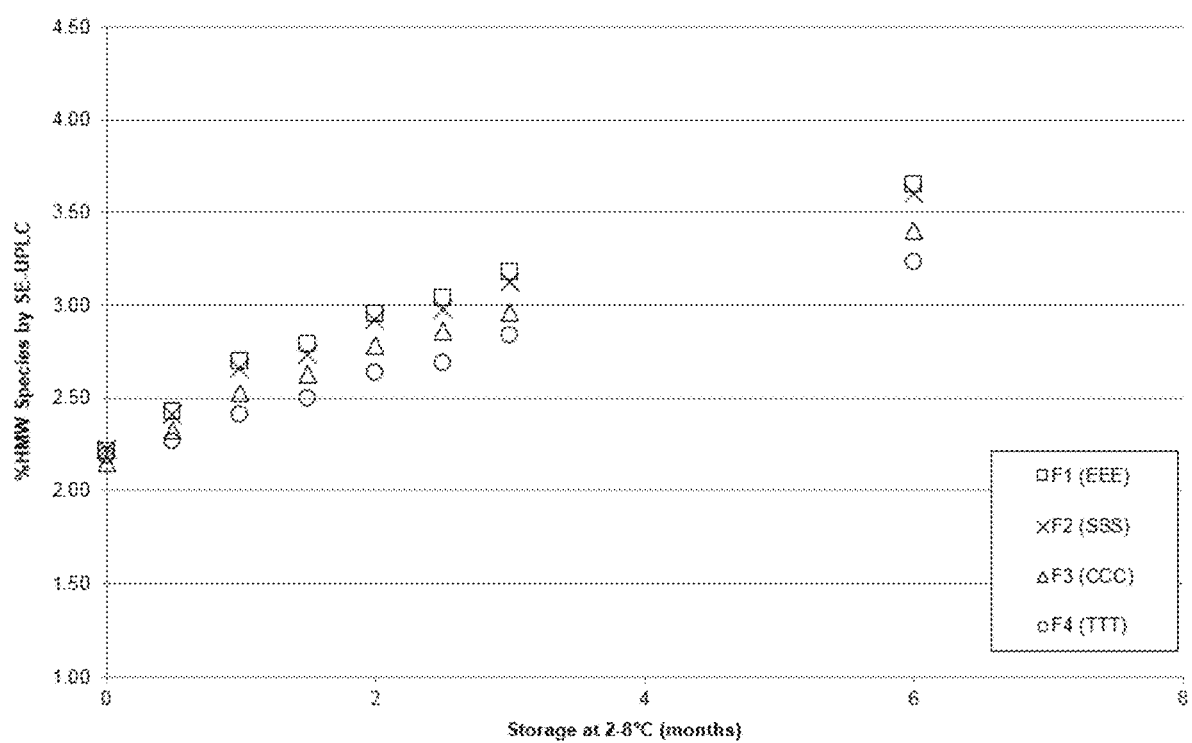
FIGS. 8A and 8B measure the percentage of high molecular weight species, by SE-UPLC, after storage at 5° C. for 3 months (FIG. 8A) or incubation at 37° C. for 28 days (FIG. 8B). Formulations F1-F4 (EEE, SSS, CCC (140 mg/ml) and TTT) are set forth in Table 8-1 below.
Figure 8B:
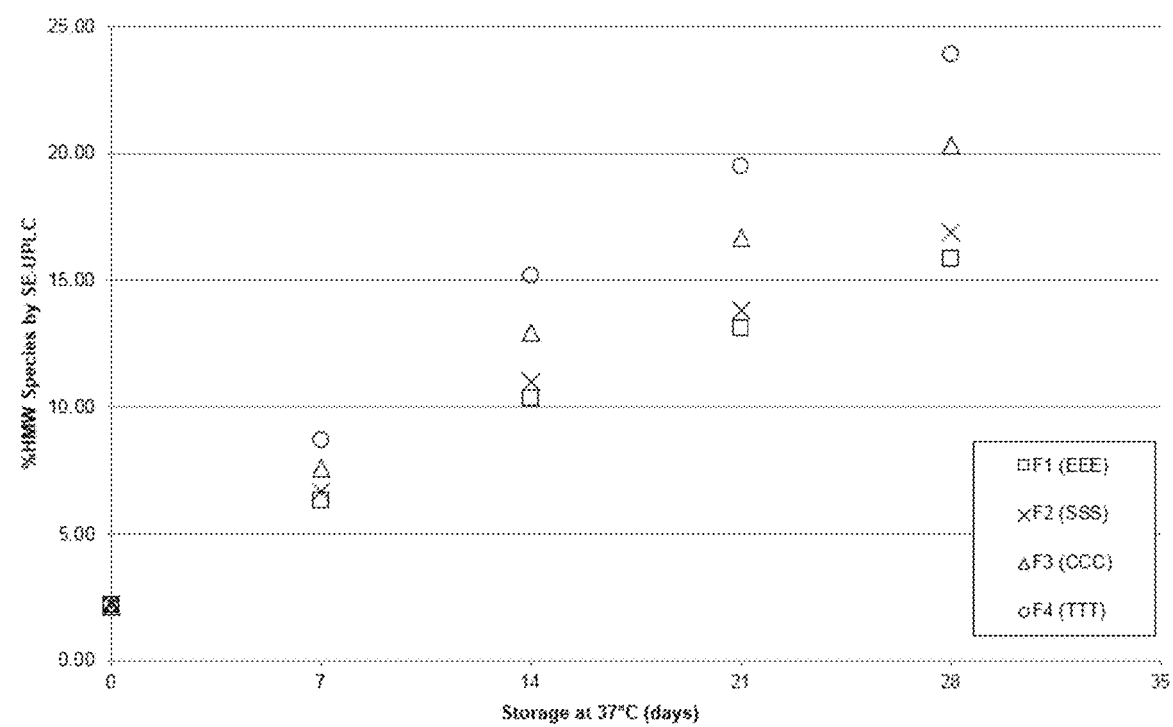

The present invention provides formulations having high concentrations of VEGF receptor fusion proteins (e.g., aflibercept), showing excellent functional and storage properties which were developed in spite of significant technical hurdles. For example, a common method for identifying suitable excipients for a formulation that includes a polypeptide drug (such as a VEGF receptor fusion protein) is by assessment of polypeptide stability under accelerated stress conditions, such as high temperature (e.g., 37° C.). Excipients, which are not suitable under non-stress conditions (e.g., a low temperature such as 5° C.), will typically cause an undesired effect, within a short period of time, while under stress, e.g., protein aggregation. This approach is common in the biotechnology and pharmaceutical industry insofar as it expedites the elimination of excipients unlikely to stabilize the drug product. See e.g., Magari, *Assessing Shelf Life Using Real-Time and Accelerated Stability Tests*, Biopharm Intl. 16(11): 36-48 (2003). In some cases, a product may be released based on accelerated stability data, but this must be done in parallel with real-time shelf-life analysis (non-accelerated). Magari (2003) and FDA, *Guidelines for Submitting Documentation for the Stability of Human Drugs and Biologics*, Rockville, Md. (1987). Here, however, at 5° C., the presence of arginine in histidine formulations was stabilizing, though arginine, it appeared, tended to decrease stability when under temperature stress (37° C.). See FIG. 8 (A-B). This property of the formulations set forth herein would have presented a technical difficulty guiding a practitioner away from choosing arginine; thus, making it unlikely that a practitioner would have chosen arginine as an excipient. Nevertheless, the formulations set forth herein resulted from the overcoming of technical hurdles such as this to achieve a formulation with high stability. Formulation of VEGF trap in histidine buffer also led to a beneficial decrease in viscosity relative to that observed with a phosphate buffer formulation. Since small needle bores are preferred for performing intravitreal injections (due to decreased patient discomfort and eye trauma), a relative low viscosity is desirable. A lower viscosity formulation requires less force to push the formulation through the needle, thus making injection of the formulation through the needle easier for the treating physician. In addition, histidine and arginine containing formulation were well tolerated in rabbit eyes.

Reference will now be made in detail to representative embodiments. It should be understood that the following descriptions are not intended to limit the embodiments to one preferred embodiment. To the contrary, they are intended to cover alternatives, modifications, and equivalents as can be included within the spirit and scope of the described embodiments as defined in the appended claims.

Unless defined otherwise, all technical and scientific terms used herein have the same meaning as commonly understood by one of ordinary skill in the art to which the disclosure pertains. As used herein, the term "about," when used in reference to a particular recited numerical value, means that the value may vary from the recited value by no more than 1%. So for example, as used herein, the expression "about 100" includes 99 and 101 and all values in between (e.g., 99.1%, 99.2%, 99.3%, 99.4%, etc.).

In an embodiment of the invention, a pharmaceutical formulation of the present invention is compliant with USP<789> for small volume injection (SVP) of ophthalmic solutions, e.g., contains less than about 50 particles ≥10 µm in diameter per ml; contains less than about 5 particles ≥25 µm in diameter per ml; or contains less than about 2 particles ≥50 in diameter per ml.

Note that for purposes herein, "intravitreal injection" refers to injection into the vitreous of the eye (near the retina at the back of the eye). The expressions "suitable for intravitreal administration," "suitable for intravitreal injection," and the like mean that the formulation in question can be safely injected into the vitreous of a subject's eye without causing any adverse reactions beyond those known to be associated with intravitreal injection of EYLEA.

The term "pharmaceutical formulation" herein refers to formulations including pharmaceutically acceptable carriers, e.g., used to administer VEGF receptor fusion proteins (e.g., aflibercept or conbercept) to a subject for a therapeutic/medicinal use.

The term "pharmaceutically acceptable" refers to a formulation that within the scope of sound medical judgement is suitable for administration with the eye.

The term "subject" herein refers to any mammalian (e.g., rabbit, mouse, rat or monkey) subject, particularly a human, e.g., for whom diagnosis, prognosis or therapy is desired with the formulations as described herein.

The term "aqueous" formulation refers to a formulation which includes water.

The term "treat" or "treatment" refers to a therapeutic measure that reverses, stabilizes or eliminates an undesired disease or disorder (e.g., an angiogenic eye disorder or cancer), for example, by causing the regression, stabilization or elimination of one or more symptoms or indicia of such disease or disorder by any clinically measurable degree, e.g., with regard to an angiogenic eye disorder, by causing a reduction in or maintenance of diabetic retinopathy severity score (DRSS), by improving or maintaining vision (e.g., in best corrected visual acuity e.g., as measured by an increase in ETDRS letters), increasing or maintaining visual field and/or reducing or maintaining central retinal thickness and, with respect to cancer, stopping or reversing the growth, survival and/or metastasis of cancer cells in the subject. Typically, the therapeutic measure is administration of one or more doses of a therapeutically effective amount of VEGF receptor fusion protein to the subject with the disease or disorder.

"Prevent" or "prevention" refer to a prophylactic measure to cease the development of an undesired disease or disorder (e.g., an angiogenic eye disorder).

SE-UPLC can be used in the present invention to quantitate the presence of high molecular weight species in a formulation. SE refers to size exclusion chromatography. UPLC refers to ultra-performance liquid chromatography. Suitable SE columns, which may be used in a UPLC system, to characterize such HMW species of VEGF receptor fusion proteins (e.g., aflibercept or conbercept) in a formulation, are capable of resolving molecules in the molecular weight range of about 10,000-450,000 Daltons. See for example, the ACQUITY UPLC Protein BEH SEC 200 Å Column. In an embodiment of the invention, two of such columns are connected in tandem when quantitating HMW species in a formulation. UPLC brings improvements over HPLC (high performance liquid chromatography) in sensitivity and resolution. UPLC uses instrumentation that operates at high pressures and uses finer particles (typically less than about 2.5 µm) than that used in HPLC. Moreover, the UPLC mobile phases operate at high linear velocities than HPLC.

Embodiments herein include formulations that comprise a high concentration (e.g., about 60 mg/ml, about 80 mg/ml, about 90 mg/ml, about 100 mg/ml, about 113.3 mg/ml, about 114.3 mg/ml, about 120 mg/ml, about 133.3 mg/ml, about 140 mg/ml, about 150 mg/ml, about 200 mg/ml or about 250 mg/ml) of VEGF receptor fusion protein (e.g., aflibercept or conbercept). Suitable formulations included herein comprise a high concentration of VEGF receptor fusion protein, a buffer, a thermal stabilizer and a surfactant. In some aspects, a suitable formulation further includes a viscosity reducing agent. In other aspects, the suitable formulation substantially excludes all viscosity reducing agents. Typical formulations have a pH of from about 5.0 to about 6.8 (e.g., 5.8), but can include any pH useful for administration of the VEGF receptor fusion protein to the eye of a subject.

The present invention includes formulations that include a VEGF receptor fusion protein (e.g., aflibercept or conbercept) in association with one or more further therapeutic agents (e.g., an Ang-2 inhibitor (e.g., an anti-ANG2 antibody or antigen-binding fragment thereof or nesvacumab), a Tie-2 receptor activator, an anti-PDGF, PDGF receptor or PDGF receptor beta antibody or antigen-binding fragment thereof and/or an additional VEGF antagonist such as bevacizumab, ranibizumab, pegaptanib or a soluble form of human vascular endothelial growth factor receptor-3 (VEGFR-3) comprising extracellular domains 1-3, expressed as an Fc-fusion protein) as well as methods of prevention or treatment comprising administering such formulations as discussed herein. In an embodiment of the invention, a formulation of the present invention includes a VEGF receptor fusion protein, such as aflibercept, but excludes any further therapeutic agent (e.g., which is an antibody or antigen-binding fragment thereof).

The term "in association with" indicates that a formulation and a further therapeutic agent can be formulated into a single composition, e.g., for simultaneous delivery, or formulated separately into two or more compositions (e.g., a kit). The further therapeutic agent may, itself, be formulated in its own pharmaceutical formulation. Each can be administered to a subject at the same time as the other or at a different time than when the other is administered; for example, each administration may be given non-simultaneously (e.g., separately or sequentially) at intervals over a given period of time. Moreover, the formulation and the further therapeutic agent may be administered to a subject by the same or by a different route.

In an embodiment of the invention, a formulation of the present invention includes any one or more of sodium sulfate (e.g., 50 mM); sodium thiocyanate (e.g., 50 mM); sodium citrate (e.g., 40 mM); glycine (e.g., 50 mM); sodium chloride (e.g., 50 mM); lysine (e.g., 50 mM); sodium aspartate (e.g., 50 mM); and/or sodium glutamate (e.g., 50 mM). For example, in an embodiment the formulation comprises a combination of sodium citrate (e.g., 50 mM) and arginine hydrochloride (e.g., 50 mM); glycine (e.g., 50 mM) and arginine hydrochloride (e.g., 50 mM); sodium aspartate (e.g., 50 mM) and arginine hydrochloride (e.g., 50 mM); or sodium glutamate (e.g., 50 mM) and arginine hydrochloride (e.g., 50 mM).

VEGF Receptor Fusion Proteins and Other VEGF Inhibitors

For purposes herein, a "VEGF receptor fusion protein" refers to a molecule that comprises one or more VEGF receptors or domains thereof, fused to another polypeptide, which interferes with the interaction between VEGF and a natural VEGF receptor, e.g., wherein two of such fusion polypeptides are associated thereby forming a homodimer or other multimer. Such VEGF receptor fusion proteins may be referred to as a "VEGF-Trap" or "VEGF Trap". VEGF receptor fusion proteins within the context of the present disclosure that fall within this definition include, chimeric polypeptides which comprise two or more immunoglobulin (Ig)-like domains of a VEGF receptor such as VEGFR1 (also known as Flt1) and/or VEGFR2 (also known as Flk1 or KDR), and may also contain a multimerizing domain (for example, an Fc domain).

An exemplary VEGF receptor fusion protein is a molecule referred to as VEGF1R2-FcΔC1(a) which is encoded by the nucleic acid sequence of SEQ ID NO:1 or nucleotides 79-1374 or 79-1371 thereof.

VEGF1R2-FcΔC1(a) comprises three components:
(1) a VEGFR1 component comprising amino acids 27 to 129 of SEQ ID NO:2;
(2) a VEGFR2 component comprising amino acids 130 to 231 of SEQ ID NO:2; and
(3) a multimerization component ("FcΔC1(a)") comprising amino acids 232 to 457 of SEQ ID NO:2 (the C-terminal amino acids of SEQ ID NO:2, i.e., K458, may or may not be included in the VEGF receptor fusion proteins, see U.S. Pat. No. 7,396,664 or 7,354,579, incorporated herein for all purposes). Note that amino acids 1 to 26 of SEQ ID NO:2 are the signal sequence. In an embodiment of the invention, the VEGF receptor fusion protein comprises amino acids 27-458 or 27-457 of SEQ ID NO: 2.

In an embodiment of the invention, the VEGF receptor fusion protein comprises
(1) an immunoglobin-like (Ig) domain 2 of a first VEGF receptor (e.g., VEGFR1), and
(2) an Ig domain 3 of a second VEGF receptor (e.g., VEGFR2),
(3) and, optionally, further including an Ig domain 4 of the second VEGF receptor (e.g., VEGFR2) and
(4) a multimerizing component (e.g., Fc domain of IgG).

For example, in an embodiment of the invention, the VEGF receptor fusion protein has the following arrangement of said domains:

[VEGFR1 Ig domain 2]-[VEGFR2 Ig domain 3]-[MC] (e.g., a homodimer thereof) or

[VEGFR1 Ig domain 2]-[VEGFR2 Ig domain 3]-[VEGFR2 Ig domain 4]-[MC] (e.g., a homodimer thereof).

In an embodiment of the invention, the VEGF receptor fusion protein is a VEGF mini-trap which is a VEGF trap molecule with a truncated multimerizing component (e.g., Fc), e.g., wherein the mini-trap still includes an Fc hinge region. See e.g., WO2005/00895 or U.S. Pat. No. 7,396,664.

Note that the present disclosure also includes, within its scope, high concentration formulations including, instead of a VEGF receptor fusion proteins, VEGF binding molecules and anti-VEGF antibodies and antigen-binding fragments thereof, bevacizumab (e.g., at a concentration of about 80-90 or 88 mg/ml), ranibizumab (e.g., at a concentration of about 20-40 mg/ml, e.g., 21-35, 21 or 35 mg/ml), an anti-VEGF aptamer such as pegaptanib (e.g., pegaptanib sodium), a single chain (e.g., $V_L$-$V_H$) anti-VEGF antibody such as brolucizumab (e.g., at a concentration of about 200-400 or 200, 210, 400 or 420 mg/ml), an anti-VEGF DARPin such as the Abicipar Pegol DARPin (e.g., at a concentration of about 70-140, 70 or 140 mg/ml), or a bispecific anti-VEGF antibody, e.g., which also binds to ANG2, such as RG7716 (e.g., at a concentration of about 100-400, 100, 105, 400 or 420 mg/ml).

In order to minimize the repetitiveness of the embodiments discussed herein, it is contemplated that the scope of the present invention includes embodiments wherein any of the formulations discussed herein include, in place of a VEGF receptor fusion protein, an anti-VEGF antibody or antibody fragment or other VEGF binding molecule as discussed herein (e.g., substituted with an anti-VEGF DARPin) at any of the concentrations discussed herein. For example, the present invention includes a formulation having 35 or 80 mg/ml ranibizumab, a buffer, a thermal stabilizer, a viscosity reducing agent and a surfactant.

DARPins are Designed Ankyrin Repeat Proteins. DARPins generally contain three to four tightly packed repeats of approximately 33 amino acid residues, with each repeat containing a β-turn and two anti-parallel α-helices. This rigid framework provides protein stability whilst enabling the presentation of variable regions, normally comprising six amino acid residues per repeat, for target recognition.

An "anti-VEGF" antibody or antigen-binding fragment of an antibody refers to an antibody or fragment that specifically binds to VEGF.

Illustrative VEGF receptor fusion proteins include aflibercept (EYLEA®, Regeneron Pharmaceuticals, Inc.) or conbercept (sold commercially by Chengdu Kanghong Biotechnology Co., Ltd.). See International patent application publication no. WO2005/121176 or WO2007/112675. The terms "aflibercept" and "conbercept" include biosimilar versions thereof. A biosimilar version of a reference product (e.g., aflibercept) generally refers to a product comprising the identical amino acid sequence, but includes products which are biosimilar under the U.S. Biologics Price Competition and Innovation Act.

Pharmaceutical formulations of the present invention are "high concentration". High concentration pharmaceutical formulations of the present invention include VEGF receptor fusion protein at a concentration of at least 41 mg/ml, of at least 80 mg/ml, of at least 100 mg/ml, of at least 125 mg/ml, of at least 140 mg/ml, of at least 150 mg/ml, of at least 175 mg/ml, of at least 200 mg/ml, of at least 225 mg/ml, of at least 250 mg/ml, or of at least 275 mg/ml. Alternatively, "high concentration" can refer to formulations that include a concentration of VEGF receptor fusion protein of from about 140 mg/ml to about 160 mg/ml, at least about 140 mg/ml but less than 160 mg/ml, from about 41 mg/ml to about 275 mg/ml, from about 70 mg/ml to about 75 mg/ml or from about 80 mg/ml to about 250 mg/ml. In some aspects, the VEGF receptor fusion protein concentration in the formulation is about any of the following concentrations: 41 mg/ml; 42 mg/ml; 43 mg/ml; 44 mg/ml; 45 mg/ml; 46 mg/ml; 47 mg/ml; 48 mg/ml; 49 mg/ml; 50 mg/ml; 51 mg/ml; 52 mg/ml; 53 mg/ml; 54 mg/ml; 55 mg/ml; 56 mg/ml; 57 mg/ml; 58 mg/ml; 59 mg/ml; 60 mg/ml; 61 mg/ml; 62 mg/ml; 63 mg/ml; 64 mg/ml; 65 mg/ml; 66 mg/ml; 67 mg/ml; 68 mg/ml; 69 mg/ml; 70 mg/ml; 71 mg/ml; 72 mg/ml; 73 mg/ml; 74 mg/ml; 75 mg/ml; 76 mg/ml; 77 mg/ml; 78 mg/ml; 79 mg/ml; 80 mg/ml; 81 mg/ml; 82 mg/ml; 83 mg/ml; 84 mg/ml; 85 mg/ml; 86 mg/ml; 87 mg/ml; 88 mg/ml; 89 mg/ml; 90 mg/ml; 91 mg/ml; 92 mg/ml; 93 mg/ml; 94 mg/ml; 95 mg/ml; 96 mg/ml; 97 mg/ml; 98 mg/ml; 99 mg/ml; 100 mg/ml; 101 mg/ml; 102 mg/ml; 103 mg/ml; 104 mg/ml; 105 mg/ml; 106 mg/ml; 107 mg/ml; 108 mg/ml; 109 mg/ml; 110 mg/ml; 111 mg/ml; 112 mg/ml; 113 mg/ml; 113.3 mg/ml; 114 mg/ml; 114.1 mg/ml; 114.2 mg/ml; 114.3 mg/ml; 114.4 mg/ml; 114.5 mg/ml; 114.6 mg/ml, 114.7 mg/ml, 114.8 mg/ml; 114.9 mg/ml; 115 mg/ml; 116 mg/ml; 117 mg/ml; 118 mg/ml; 119 mg/ml; 120 mg/ml; 121 mg/ml; 122 mg/ml; 123 mg/ml; 124 mg/ml; 125 mg/ml; 126 mg/ml; 127 mg/ml; 128 mg/ml; 129 mg/ml; 130 mg/ml; 131 mg/ml; 132 mg/ml; 133 mg/ml; 133.3 mg/ml; 133.4 mg/ml, 134 mg/ml; 135 mg/ml; 136 mg/ml; 137 mg/ml; 138 mg/ml; 139 mg/ml; 140 mg/ml; 141 mg/ml; 142 mg/ml; 143 mg/ml; 144 mg/ml; 145 mg/ml; 146 mg/ml; 147 mg/ml; 148 mg/ml; 149 mg/ml; 150 mg/ml; 151 mg/ml; 152 mg/ml; 153 mg/ml; 154 mg/ml; 155 mg/ml; 156 mg/ml; 157 mg/ml; 158 mg/ml; 159 mg/ml; 160 mg/ml; 161 mg/ml; 162 mg/ml; 163 mg/ml; 164 mg/ml; 165 mg/ml; 166 mg/ml; 167 mg/ml; 168 mg/ml; 169 mg/ml; 170 mg/ml; 171 mg/ml; 172 mg/ml; 173 mg/ml; 174 mg/ml; 175 mg/ml; 176 mg/ml; 177 mg/ml; 178 mg/ml; 179 mg/ml; 180 mg/ml; 181 mg/ml; 182 mg/ml; 183 mg/ml; 184 mg/ml; 185 mg/ml; 186 mg/ml; 187 mg/ml; 188 mg/ml; 189 mg/ml; 190 mg/ml; 191 mg/ml; 192 mg/ml; 193 mg/ml; 194 mg/ml; 195 mg/ml; 196 mg/ml; 197 mg/ml; 198 mg/ml; 199 mg/ml; 200 mg/ml; 201 mg/ml; 202 mg/ml; 203 mg/ml; 204 mg/ml; 205 mg/ml; 206 mg/ml; 207 mg/ml; 208 mg/ml; 209 mg/ml; 210 mg/ml; 211 mg/ml; 212 mg/ml; 213 mg/ml; 214 mg/ml; 215 mg/ml; 216 mg/ml; 217 mg/ml; 218 mg/ml; 219 mg/ml; 220 mg/ml; 221 mg/ml; 222 mg/ml; 223 mg/ml; 224 mg/ml; 225 mg/ml; 226 mg/ml; 227 mg/ml; 228 mg/ml; 229 mg/ml; 230 mg/ml; 231 mg/ml; 232 mg/ml; 233 mg/ml; 234 mg/ml; 235 mg/ml; 236 mg/ml; 237 mg/ml; 238 mg/ml; 239 mg/ml; 240 mg/ml; 241 mg/ml; 242 mg/ml; 243 mg/ml; 244 mg/ml; 245 mg/ml; 246 mg/ml; 247 mg/ml; 248 mg/ml; 249 mg/ml; 250 mg/ml; 251 mg/ml; 252 mg/ml; 253 mg/ml; 254 mg/ml; 255 mg/ml; 256 mg/ml; 257 mg/ml; 258 mg/ml; 259 mg/ml; 260 mg/ml; 261 mg/ml; 262 mg/ml; 263 mg/ml; 264 mg/ml; 265 mg/ml; 266 mg/ml; 267 mg/ml; 268 mg/ml; 269 mg/ml; 270 mg/ml; 271 mg/ml; 272 mg/ml; 273 mg/ml; 274 mg/ml; or 275 mg/ml. Other VEGF receptor fusion protein concentrations are contemplated herein, as long as the concentration functions in accordance with embodiments herein.

In an embodiment of the invention, a pharmaceutical formulation of the present invention is of such a concentration as to contain about 4, 6, 8, 10, 12, 14, 16, 18 or 20 mg VEGF receptor fusion protein (e.g., aflibercept), or the amount of such protein in any of the acceptable doses thereof which are discussed herein, in about 100 µl or less, about 75 µl or less or about 70 µl or less, e.g., about 50 µl; 51 µl; 52 µl; 53 µl; 54 µl; 55 µl; 56 µl; 57 µl; 58 µl; 59 µl; 60 µl; 61 µl; 62 µl; 63 µl; 64 µl; 65 µl; 66 µl; 67 µl; 68 µl; 69 µl; 70 µl; 71 µl; 72 µl; 73 µl; 74 µl; 75 µl; 76 µl; 77 µl; 78 µl; 79 µl; 80 µl; 81 µl; 82 µl; 83 µl; 84 µl; 85 µl; 86 µl; 87 µl; 88 µl; 89 µl; 90 µl; 91 µl; 92 µl; 93 µl; 94 µl; 95 µl; 96 µl; 97 µl; 98 µl; 99 µl; or 100 µl.

The present invention includes any of the formulations set forth under "Illustrative Formulations" herein, but wherein the concentration of the VEGF receptor fusion protein (e.g., aflibercept) is substituted with a concentration which is set forth in this section ("VEGF Receptor Fusion Proteins and Other VEGF inhibitors").

Buffers

Buffers for use herein refer to solutions that resist pH change by use of acid-base conjugates. Buffers are capable of maintaining pH in the range of from about 5.0 to about 6.8, and more typically, from about 5.8 to about 6.5, and most typically, from about 6.0 to about 6.5. In some cases, the pH of the formulation of the present invention is about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, or about 6.8. Example buffers for inclusion in formulations herein include histidine-based buffers, for example, histidine, histidine hydrochloride, and histidine acetate. Buffers for inclusion in formulations herein can alternatively be phosphate-based buffers, for example, sodium phosphate, acetate-based buffers, for example, sodium acetate or acetic acid, or can be citrate-based, for example, sodium citrate or citric acid. It is also recognized that buffers can be a mix of the above, as long as the buffer functions to buffer the formulations in the above described pH ranges. In some cases, the buffer is from about 5 mM to about 25 mM, or more typically, about 5 mM to about 15 mM. Buffers can be about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, or about 25 mM.

In an embodiment of the invention, a histidine-based buffer is prepared using histidine and histidine monohydrochloride.

Surfactants

Surfactant for use herein refers to ingredients that protect the higher concentration of VEGF receptor fusion protein from various surface and interfacial induced stresses. As such, surfactants can be used to limit or minimize VEGF receptor fusion protein aggregation, and promote protein solubility. Suitable surfactants herein have been shown to be non-ionic, and can include surfactants that have a polyoxyethylene moiety. Illustrative surfactants in this category include: polysorbate 20, polysorbate 80, poloxamer 188, polyethylene glycol 3350, and mixtures thereof. Surfactants in the formulations can be present at from about 0.02% to about 0.1% weight per volume (w/v), and more typically, about 0.02% to about 0.04% (w/v). In some cases, the surfactant is about 0.02% (w/v), about 0.03% (w/v), about 0.04% (w/v), about 0.05% (w/v), about 0.06% (w/v), about 0.07% (w/v), about 0.08% (w/v), about 0.09% (w/v), or about 0.1% (w/v).

Thermal Stabilizers

Thermal stabilizers for use herein refers to ingredients that provide thermal stability against thermal denaturation of the VEGF receptor fusion protein, as well as protect against loss of VEGF receptor fusion protein potency or activity. Suitable thermal stabilizers include sugars, and can be sucrose, trehalose, sorbitol or mannitol, or can be amino acids, for example L-proline, L-arginine (e.g., L-arginine monohydrochloride), or taurine. Additionally, thermal stabilizers may also include substituted acrylamides or propane sulfonic acid, or may be compounds like glycerol.

In some cases, the formulations herein include both a sugar and taurine, a sugar and an amino acid, a sugar and propane sulfonic acid, a sugar and taurine, glycerol and taurine, glycerol and propane sulfonic acid, an amino acid and taurine, or an amino acid and propane sulfonic acid. In addition, formulations can include a sugar, taurine and propane sulfonic acid, glycerol, taurine and propane sulfonic acid, as well as L-proline, taurine and propane sulfonic acid.

Embodiments herein typically have thermal stabilizers present alone, each independently present at a concentration of, or present in combination at a total concentration of, from about 2% (w/v) to about 10% (w/v) or 4% (w/v) to about 10% (w/v), or about 4% (w/v) to about 9% (w/v), or about 5% (w/v) to about 8% (w/v). Thermal stabilizers in the formulation can be at a concentration of about 2% (w/v), about 2.5% (w/v), about 3% (w/v), about 4% (w/v), about 5% (w/v), about 6% (w/v), about 7% (w/v), about 8% (w/v), about 9% (w/v), about 10% (w/v) or about 20% (w/v).

With respect to taurine and propane sulfonic acid, in an embodiment of the invention, these thermal stabilizers can be present in the formulations at about from 25 mM to about 100 mM, and more typically from about 50 mM to about 75 mM (as compared to the other thermal stabilizers).

Viscosity Reducing Agents

Viscosity reducing agents typically are used to reduce or prevent protein aggregation. Viscosity reducing agents for inclusion herein include: sodium chloride, magnesium chloride, D- or L-arginine (e.g., L-arginine monohydrochloride), lysine, or mixtures thereof. When present herein, viscosity reducing agents can be present at from about 10 mM to about 100 mM, and more typically from about 30 mM to about 75 mM, and even more typically from about 40 mM to about 70 mM. In some cases the viscosity reducing agent is present at about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM or about 100 mM.

Formulation Viscosity

Formulations in accordance with embodiments herein can also have a pharmaceutically acceptable viscosity for ocular administration, for example, intravitreal injection. Viscosity generally refers to the measure of resistance of a fluid which is being deformed by either shear stress or tensile stress (typically measured by techniques known in the art, viscometer or rheometer, for example). Typical viscosities of formulations in accordance with embodiments herein are from about 5.0 cP (centipoise) to about 15 cP, from about 11 cP to about 14 cP, from about 12 cP to about 15 cP or from about 11 cP to about 12 cP. As such, formulation viscosity herein can be about 5.0 cP, about 6.0, about 7.1 cP, about 7.2 cP, about 7.3 cP, about 7.4 cP, about 7.5 cP, about 7.6 cP, about 10 cP, about 10.5 cP, about 11.0 cP, about 11.5 cP, about 12.0 cP, about 12.5 cP, about 13.0 cP, about 13.5 cP, about 14.0 cP, about 14.5 cP, or about 15.0 cP (e.g., when measured at 20° C.).

Various embodiments herein do not require inclusion of an inorganic salt, or other viscosity reducing agent, to maintain these highly useful viscosities. Typically, high concentration protein solutions require viscosity reducing agents to avoid protein aggregation and higher viscosity, making the formulations difficult for intravitreal injection and reducing the potency of the VEGF receptor fusion protein. As such, embodiments herein include formulations that have had substantially no, or no added, sodium chloride (NaCl), magnesium chloride ($MgCl_2$), D- or L-arginine hydrochloride, lysine or other viscosity reducing agent.

Formulation Osmolality

Osmolality is a critical attribute for injectable formulations. It is desirable to have products match physiological osmotic conditions. Furthermore, osmolality provides confirmation of soluble content in solution. In an embodiment of the invention, the osmolality of a formulation of the present invention is less than or equal to about 506 mmol/Kg or from about 250 to about 506 mmol/Kg., e.g., about 250, 260, 270, 280, 290, 299, 300, 310, 314, 315, 316, 324, 343, 346, 349, 369, 384, 403, 426, 430 or 506 mmol/Kg. In an embodiment of the invention, the osmolality is lower than about 250 mmol/Kg.

Purity and Stability of Formulations

High concentration VEGF receptor fusion protein containing formulations described herein are stable during manufacture and storage. The term "stable" herein refers to formulations that include VEGF receptor proteins that retain both chemical and physical stability over the period of formulation manufacturing and storage, e.g., that maintains integrity and has minimal degradation, denaturation, or unfolding. VEGF receptor protein stability can be determined using analytical techniques available in the art at different temperatures and over different periods of time. In particular, VEGF receptor chemical stability (potency) can be determined using various bioassays (for example, a BAF/3 VEGFR1/EPOR cell line used to determine VEGF 165 binding by the VEGF receptor fusion proteins herein), and physical stability, by size exclusion (SE) chromatographic analysis, UPLC (ultra-performance liquid chromatography) size exclusion (SE) chromatography, visual appearance, OD, pH, charge variant formation, and rate of high molecular weight (HMW) species formation. A stable VEGF receptor fusion protein is one that shows limited change in its OD, pH, formation of charge variants, and formation of HMW species.

A "high molecular weight" (HMW) species as used herein, with reference to a formulation containing a given VEGF Trap (e.g., aflibercept), refers to any species of polypeptide or polypeptide complex in the formulation which elutes from a size exclusion column (e.g., SE-UPLC) ahead of (e.g., with a higher molecular weight than) VEGF Trap polypeptide and/or a homodimer thereof. The percentage of HMW species refers to the percentage of such species relative to the overall quantity of polypeptides in the formulation, e.g., by SE-UPLC analysis.

In an embodiment of the invention, as discussed more fully in the Examples below, stable formulations show significant VEGF receptor fusion protein potency and physical stability for a period of up to 12 months, up to 24 months, and/or up to 36 months when stored at about 2° C. to about 8° C.

In an embodiment of the invention, formulation of the present invention is one that:

After about 28 days at about 37° C. has about a 3, 5, 10, 11, 12, 13, 14, 15, 16, 17, 18, 20, 30, 35 or 37% (or 10-15% or 15-20% or 10-20%) increase in high molecular weight species (e.g., as measured by SE-UPLC or SEC)

After about 28 days at about 37° C. has about a 5, 6, 9, 10, 11, 12, 13, 14, 15, 16, 17, 18, 19, 20, 21 or 22% (or 5-20% or 5-10% or 10-15% or 15-20%) decrease in main species (e.g., as measured by SE-UPLC or SEC)

After about 28 days at about 37° C., has about 80, 81, 82, 83, 84, 85, 86 or 87% (or about 80-85%) or more protein as main species (e.g., as measured by SE-UPLC or SEC)

After about 28 days at about 37° C. has about a 1 or 1.5 or 2% (or 1-2%) increase in low molecular weight species (e.g., as measured by SE-UPLC or SEC)

After about one month at about 37° C. has about a 16% increase in high molecular weight species; and/or about a 17% decrease in main species and/or about a 0.5% or <1% increase in low molecular weight species; and/or after about two months at about 5° C., has about a 1% decrease in main species, and/or about a 1% increase in high molecular weight species and/or no significant or detectable amounts low molecular weight (LMW) species; and/or after about 2 months at about 5° C., has about 97% main species (e.g., as measured by SE-UPLC or SEC)

After about 12 months at about 2-8° C. has about a 3-3.5% increase in high molecular weight species (e.g., as measured by SE-UPLC or SEC)

After about 12 months at about 2-8° C. has less than about a 1% or a 1, 2, 3 or 4% (e.g., 1-4% or 3-4%) decrease in main species (e.g., as measured by SE-UPLC or SEC)

After about 12 months at about 2-8° C., has about 94 or 95% or more protein as main species (e.g., as measured by SE-UPLC or SEC)

After about 3 months at about 2-8° C. has about a 1 or 2% increase in high molecular weight species (e.g., as measured by SE-UPLC or SEC)

After about 6 months at about 2-8° C. has about a <1, 1 or 2% increase in high molecular weight species (e.g., as measured by SE-UPLC or SEC)

After about 5½ or 6 months at about 5° C. has about 2.5, 3.0 or 3.5 (or about 2.5-3.5%) total high molecular weight species (e.g., as measured by SE-UPLC or SEC).

After about 6 months at about 2-8° C. has less than about a 1% or 1 or 2% (or about 0.5-2% or 1-2%) decrease in main species (e.g., as measured by SE-UPLC or SEC)

After about 6 months at about 2-8° C., has about 96 or 97 or 98% (or 96-98%) or more protein as main species (e.g., as measured by SE-UPLC or SEC)

After about 24 months or 36 months at about 2-8° C., had less than about 5 or 6 or 7% (e.g., about 1.5, 2, 3, 4 or 5%) (or 1.5-5% or 1.5-2.5%) increase in high molecular weight species; and/or has about 3.0, 3.25, 3.5, 4.0, 4.5 or 5% total high molecular weight species; and/or a decrease of about 2 or 3% (or 2-3%) main species; and/or a total amount of main species of about 95 or 96% or more (or 95-96%) (e.g., as measured by SE-UPLC or SEC)

After about 1 month at about 37° C., has about 97, 98, 99 or 100% (or 97-100%) of aflibercept in the formulation which is recoverable by RP-HPLC Immediately after manufacture and purification, has less than about 1.5, 2, 2.5, 3.0 or 3.5% high molecular weight species (e.g., as measured by SE-UPLC or SEC)

After about 6 months at about 37° C., has at least about 70% or 75% (e.g., 70-75%) of aflibercept as main species/main peak (e.g., as measured by capillary isoelectric focusing (cIEF) or imaged capillary isoelectric focusing) (non-acidic and non-basic species)

After about 36 months at about 2-8° C., has about a 1 or 2% (or 1-2%) increase in acidic species (e.g., as measured by capillary isoelectric focusing (cIEF) or imaged capillary isoelectric focusing)

After about 36 months at about 2-8° C., has about a 1% or less decrease in main species/main peak (e.g., as measured by capillary isoelectric focusing (cIEF) or imaged capillary isoelectric focusing)

After about 36 months at about 2-8° C., has about 78-79% main species/main peak (e.g., as measured by capillary isoelectric focusing (cIEF) or imaged capillary isoelectric focusing)

and/or

When administered intravitreally to a mammal, such as a human or rabbit or mouse (e.g., with an angiogenic eye disorder such as wet AMD), does not cause any adverse events that are clinically different from those observed for EYLEA (e.g., when EYLEA is dosed intravitreally at 0.5 or 2.0 mg); or does not cause clinically significant inflammation in the eye, prolonged intraocular pressure (TOP) increases, prolonged increases in blood pressure or decreases and/or retinal detachment.

Further, in an embodiment of the invention, high concentration VEGF receptor fusion proteins are stable as they show little or no formation of acidic charge variants over the course of manufacture and storage, for example, little or no formation of charge variants as tested by Imaged Capillary Isoelectric Focusing, for example.

In an embodiment of the invention, a formulation of the present invention exhibits less than or equal to about 8% low molecular weight (LMW) species.

In an embodiment of the invention, a formulation of the present invention has less than about 0.2, 0.4 or 0.5 EU (endotoxin units)/ml of endotoxin;

In an embodiment of the invention, a formulation of the present invention is essentially free of particulate matter or particulate matter of about 1, 2, 5, 10, 25 or 50 micrometers (or more) in size.

In an embodiment of the invention, when a formulation of the present invention is analyzed by non-reduced CE-SDS (SDS capillary gel electrophoresis), at least 97% of the total peak area is the main peak.

In an embodiment of the invention, when a formulation of the present invention is analyzed by size-exclusion UPLC (SE-UPLC), at least 93, 94 or 95% of the total peak area is the main peak and less than or equal to 3.5, 4, 5 or 6% is aggregate.

In an embodiment of the invention, a formulation of the present invention is at about 2° C., 3° C., 4° C., 5° C., 6° C., 7° C. or 8° C., 2-8° C. (e.g., an average temperature of 5° C.), 23° C., 25° C., 30° C. or 37° C.

Illustrative Formulations

Illustrative high concentration VEGF receptor fusion protein containing formulations include the following:

Formulation A: 80 mg/ml aflibercept, 10 mM histidine-based buffer, 5% (w/v) sucrose, 0.03% (w/v) polysorbate 20, and 40 mM sodium chloride, with a pH of 5.8 to 6.2.

Formulation B: 80 mg/ml aflibercept, 10 mM phosphate-based buffer, 5% (w/v) sucrose, 0.03% (w/v) polysorbate 20, and 40 mM sodium chloride, with a pH of 5.8 to 6.2.

Formulation C: 80 mg/ml aflibercept, 10 mM citrate-based buffer, 5% (w/v) sucrose, 0.03% (w/v) polysorbate 20, and 40 mM sodium chloride, with a pH of 5.8 to 6.2.

Formulation D: 80 mg/ml aflibercept, 10 mM histidine-based buffer, 5% (w/v) sucrose, 0.03% (w/v) polysorbate 80, and 40 mM sodium chloride, with a pH of 6.2.

Formulation E: 80 mg/ml aflibercept, 10 mM phosphate-based buffer, 5% (w/v) sucrose, 0.03% (w/v) polysorbate 80, and 40 mM sodium chloride, with a pH of 5.8 to 6.2.

Formulation F: 80 mg/ml aflibercept, 10 mM citrate-based buffer, 5% (w/v) sucrose, 0.03% (w/v) polysorbate 80, and 40 mM sodium chloride, with a pH of 5.8 to 6.2.

Formulation G: 80 mg/ml aflibercept, 10 mM histidine-based buffer, 8% (w/v) sucrose, and 0.03% (w/v) polysorbate 20, with a pH of 5.8 to 6.2, and, optionally, specifically excluding a viscosity reducing agent.

Formulation H: 80 mg/ml aflibercept, 10 mM phosphate-based buffer, 8% (w/v) sucrose, and 0.03% (w/v) polysorbate 20, with a pH of 5.8 to 6.2, and, optionally, specifically excluding a viscosity reducing agent.

Formulation I: 80 mg/ml aflibercept, 10 mM citrate-based buffer, 8% (w/v) sucrose, and 0.03% (w/v) polysorbate 20, with a pH of 5.8 to 6.2, and, optionally, specifically excluding a viscosity reducing agent.

Formulation J: 80 mg/ml aflibercept, 10 mM histidine-based buffer, 8% (w/v) sucrose, and 0.03% (w/v) polysorbate 80, with a pH of 5.8 to 6.2, and, optionally, specifically excluding a viscosity reducing agent.

Formulation K: 80 mg/ml aflibercept, 10 mM phosphate-based buffer, 8% (w/v) sucrose, and 0.03% (w/v) polysorbate 80, with a pH of 5.8 to 6.2, and, optionally, specifically excluding a viscosity reducing agent.

Formulation L: 80 mg/ml aflibercept, 10 mM citrate-based buffer, 8% (w/v) sucrose, and 0.03% (w/v) polysorbate 80, with a pH of 5.8 to 6.2, and, optionally, specifically excluding a viscosity reducing agent.

Formulation M: 150 mg/ml aflibercept, 10 mM histidine-based buffer, 5% (w/v) sucrose, 0.03% (w/v) polysorbate 20, and 40 mM sodium chloride, with a pH of 5.8 to 6.2.

Formulation N: 150 mg/ml aflibercept, 10 mM phosphate-based buffer, 5% (w/v) sucrose, 0.03% (w/v) polysorbate 20, and 40 mM sodium chloride, with a pH of 5.8 to 6.2.

Formulation O: 150 mg/ml aflibercept, 10 mM citrate-based buffer, 5% (w/v) sucrose, 0.03% (w/v) polysorbate 20, and 40 mM sodium chloride, with a pH of 5.8 to 6.2.

Formulation P: 150 mg/ml aflibercept, 10 mM histidine-based buffer, 5% (w/v) sucrose, 0.03% (w/v) polysorbate 80, and 40 mM sodium chloride, with a pH of 6.2.

Formulation Q: 150 mg/ml aflibercept, 10 mM phosphate-based buffer, 5% (w/v) sucrose, 0.03% (w/v) polysorbate 80, and 40 mM sodium chloride, with a pH of 5.8 to 6.2.

Formulation R: 150 mg/ml aflibercept, 10 mM citrate-based buffer, 5% (w/v) sucrose, 0.03% (w/v) polysorbate 80, and 40 mM sodium chloride, with a pH of 5.8 to 6.2.

Formulation S: 150 mg/ml aflibercept, 10 mM histidine-based buffer, 8% (w/v) sucrose, and 0.03% (w/v) polysorbate 20, with a pH of 5.8 to 6.2, and, optionally, specifically excluding a viscosity reducing agent.

Formulation T: 150 mg/ml aflibercept, 10 mM phosphate-based buffer, 8% (w/v) sucrose, and 0.03% (w/v) polysorbate 20, with a pH of 5.8 to 6.2 (e.g., 6.2), and, optionally, specifically excluding a viscosity reducing agent.

Formulation U: 150 mg/ml aflibercept, 10 mM citrate-based buffer, 8% (w/v) sucrose, and 0.03% (w/v) polysorbate 20, with a pH of 5.8 to 6.2, and, optionally, specifically excluding a viscosity reducing agent.

Formulation V: 150 mg/ml aflibercept, 10 mM histidine-based buffer, 8% (w/v) sucrose, and 0.03% (w/v) polysorbate 80, with a pH of 5.8 to 6.2, and, optionally, specifically excluding a viscosity reducing agent.

Formulation W: 150 mg/ml aflibercept, 10 mM phosphate-based buffer, 8% (w/v) sucrose, and 0.03% (w/v) polysorbate 80, with a pH of 5.8 to 6.2, and, optionally, specifically excluding a viscosity reducing agent.

Formulation X: 150 mg/ml aflibercept, 10 mM citrate-based buffer, 8% (w/v) sucrose, and 0.03% (w/v) polysorbate 80, with a pH of 5.8 to 6.2, and, optionally, specifically excluding a viscosity reducing agent.

Formulation Y: 80 mg/ml conbercept, 10 mM histidine-based buffer, 5% (w/v) sucrose, 0.03% (w/v) polysorbate 20, and 40 mM sodium chloride, with a pH of 5.8 to 6.2.

Formulation Z: 80 mg/ml conbercept, 10 mM phosphate-based buffer, 5% (w/v) sucrose, 0.03% (w/v) polysorbate 20, and 40 mM sodium chloride, with a pH of 5.8 to 6.2.

Formulation AA: 80 mg/ml conbercept, 10 mM citrate-based buffer, 5% (w/v) sucrose, 0.03% (w/v) polysorbate 20, and 40 mM sodium chloride, with a pH of 5.8 to 6.2.

Formulation BB: 80 mg/ml conbercept, 10 mM histidine-based buffer, 5% (w/v) sucrose, 0.03% (w/v) polysorbate 80, and 40 mM sodium chloride, with a pH of 6.2.

Formulation CC: 80 mg/ml conbercept, 10 mM phosphate-based buffer, 5% (w/v) sucrose, 0.03% (w/v) polysorbate 80, and 40 mM sodium chloride, with a pH of 5.8 to 6.2.

Formulation DD: 80 mg/ml conbercept, 10 mM citrate-based buffer, 5% (w/v) sucrose, 0.03% (w/v) polysorbate 80, and 40 mM sodium chloride, with a pH of 5.8 to 6.2.

Formulation EE: 80 mg/ml conbercept, 10 mM histidine-based buffer, 8% (w/v) sucrose, and 0.03% (w/v) polysorbate 20, with a pH of 5.8 to 6.2, and, optionally, specifically excluding a viscosity reducing agent.

Formulation FF: 80 mg/ml conbercept, 10 mM phosphate-based buffer, 8% (w/v) sucrose, and 0.03% (w/v) polysorbate 20, with a pH of 5.8 to 6.2, and, optionally, specifically excluding a viscosity reducing agent.

Formulation GG: 80 mg/ml conbercept, 10 mM citrate-based buffer, 8% (w/v) sucrose, and 0.03% (w/v) polysorbate 20, with a pH of 5.8 to 6.2, and, optionally, specifically excluding a viscosity reducing agent.

Formulation HH: 80 mg/ml conbercept, 10 mM histidine-based buffer, 8% (w/v) sucrose, and 0.03% (w/v) polysorbate 80, with a pH of 5.8 to 6.2, and, optionally, specifically excluding a viscosity reducing agent.

Formulation II: 80 mg/ml conbercept, 10 mM phosphate-based buffer, 8% (w/v) sucrose, and 0.03% (w/v) polysorbate 80, with a pH of 5.8 to 6.2, and, optionally, specifically excluding a viscosity reducing agent.

Formulation JJ: 80 mg/ml conbercept, 10 mM citrate-based buffer, 8% (w/v) sucrose, and 0.03% (w/v) polysorbate 80, with a pH of 5.8 to 6.2, and, optionally, specifically excluding a viscosity reducing agent.

Formulation KK: 150 mg/ml conbercept, 10 mM histidine-based buffer, 5% (w/v) sucrose, 0.03% (w/v) polysorbate 20, and 40 mM sodium chloride, with a pH of 5.8 to 6.2.

Formulation LL: 150 mg/ml conbercept, 10 mM phosphate-based buffer, 5% (w/v) sucrose, 0.03% (w/v) polysorbate 20, and 40 mM sodium chloride, with a pH of 5.8 to 6.2.

Formulation MM: 150 mg/ml conbercept, 10 mM citrate-based buffer, 5% (w/v) sucrose, 0.03% (w/v) polysorbate 20, and 40 mM sodium chloride, with a pH of 5.8 to 6.2.

Formulation NN: 150 mg/ml conbercept, 10 mM histidine-based buffer, 5% (w/v) sucrose, 0.03% (w/v) polysorbate 80, and 40 mM sodium chloride, with a pH of 6.2.

Formulation OO: 150 mg/ml conbercept, 10 mM phosphate-based buffer, 5% (w/v) sucrose, 0.03% (w/v) polysorbate 80, and 40 mM sodium chloride, with a pH of 5.8 to 6.2.

Formulation PP: 150 mg/ml conbercept, 10 mM citrate-based buffer, 5% (w/v) sucrose, 0.03% (w/v) polysorbate 80, and 40 mM sodium chloride, with a pH of 5.8 to 6.2.

Formulation QQ: 150 mg/ml conbercept, 10 mM histidine-based buffer, 8% (w/v) sucrose, and 0.03% (w/v) polysorbate 20, with a pH of 5.8 to 6.2, and, optionally, specifically excluding a viscosity reducing agent.

Formulation RR: 150 mg/ml conbercept, 10 mM phosphate-based buffer, 8% (w/v) sucrose, and 0.03% (w/v) polysorbate 20, with a pH of 5.8 to 6.2, and, optionally, specifically excluding a viscosity reducing agent.

Formulation SS: 150 mg/ml conbercept, 10 mM citrate-based buffer, 8% (w/v) sucrose, and 0.03% (w/v) polysorbate 20, with a pH of 5.8 to 6.2, and, optionally, specifically excluding a viscosity reducing agent.

Formulation TT: 150 mg/ml conbercept, 10 mM histidine-based buffer, 8% (w/v) sucrose, and 0.03% (w/v) polysorbate 80, with a pH of 5.8 to 6.2, and, optionally, specifically excluding a viscosity reducing agent.

Formulation UU: 150 mg/ml conbercept, 10 mM phosphate-based buffer, 8% (w/v) sucrose, and 0.03% (w/v) polysorbate 80, with a pH of 5.8 to 6.2, and, optionally, specifically excluding a viscosity reducing agent.

Formulation VV: 150 mg/ml conbercept, 10 mM citrate-based buffer, 8% (w/v) sucrose, and 0.03% (w/v) polysorbate 80, with a pH of 5.8 to 6.2, and, optionally, specifically excluding a viscosity reducing agent.

Formulation WW: 140 mg/ml VEGF receptor fusion protein (e.g., aflibercept), 10 mM histidine-based buffer, 5% (w/v) sucrose, 0.03% (w/v) polysorbate 20, and 50 mM taurine, with a pH of 5.8.

Formulation XX: 140 mg/ml VEGF receptor fusion protein (e.g., aflibercept), 20 mM histidine-based buffer, 4% (w/v) proline, 0.03% (w/v) polysorbate 20, and 50 mM arginine hydrochloride, with a pH of 5.8.

Formulation YY: 140 mg/ml VEGF receptor fusion protein (e.g., aflibercept), 20 mM histidine-based buffer, 2.5% (w/v) sucrose, 2.0% (w/v) proline, 0.03% (w/v) polysorbate 20, and 50 mM taurine, with a pH of 5.8.

Formulation ZZ: 140 mg/ml VEGF receptor fusion protein (e.g., aflibercept), 10 mM histidine-based buffer, 2.5% (w/v) sucrose, 2.0% (w/v) proline, 0.03% (w/v) polysorbate 20, and 50 mM arginine hydrochloride, with a pH of 5.8.

Formulation AAA: 140 mg/ml VEGF receptor fusion protein (e.g., aflibercept), 20 mM histidine-based buffer, 5% (w/v) sucrose, 0.03% (w/v) polysorbate 20, and 50 mM PSA, with a pH of 5.8.

Formulation BBB: 140 mg/ml VEGF receptor fusion protein (e.g., aflibercept), 20 mM histidine-based buffer, 2.5% (w/v) sucrose, 2.0% (w/v) proline, 0.03% (w/v) polysorbate 20, and 50 mM PSA, with a pH of 5.8.

Formulation CCC: 80, 100, 120 or 140 mg/ml VEGF receptor fusion protein (e.g., aflibercept), 20 mM histidine-based buffer, 5% (w/v) sucrose, 0.03% (w/v) polysorbate 20, and 50 mM arginine hydrochloride, with a pH of 5.8.

Formulation DDD: 140 mg/ml VEGF receptor fusion protein (e.g., aflibercept), 10 mM histidine-based buffer, 4% (w/v) proline, 0.03% (w/v) polysorbate 20, and 50 mM PSA, with a pH of 5.8.

Formulation EEE: 140 mg/ml VEGF receptor fusion protein (e.g., aflibercept), 20 mM histidine-based buffer, 5% (w/v) sucrose, and 0.03% (w/v) polysorbate 20 and, optionally, no thermal stabilizer, with a pH of 5.8.

Formulation FFF: 140 mg/ml VEGF receptor fusion protein (e.g., aflibercept), 10 mM sodium phosphate, 5% (w/v) sucrose and 0.03% polysorbate 20 with a pH of 6.2.

Formulation GGG: 140 mg/ml VEGF receptor fusion protein (e.g., aflibercept); 20 mM histidine, pH 5.8; 5% sucrose; 0.03% polysorbate 20; 50 mM sodium sulfate Formulation HHH: 140 mg/ml VEGF receptor fusion protein (e.g., aflibercept); 20 mM histidine, pH 5.8; 5% sucrose; 0.03% polysorbate 20; 50 mM sodium thiocyanate Formulation III: 140 mg/ml VEGF receptor fusion protein (e.g., aflibercept); 20 mM histidine, pH 5.8; 5% sucrose, 0.03% polysorbate 20; 40 mM sodium citrate Formulation JJJ: 140 mg/ml VEGF receptor fusion protein (e.g., aflibercept); 20 mM histidine, pH 5.8; 5% Sucrose, 0.03% polysorbate 20; 50 mM glycine Formulation KKK: 140 mg/ml VEGF receptor fusion protein (e.g., aflibercept); 20 mM histidine, pH 5.8; 5% sucrose, 0.03% polysorbate 20; 50 mM sodium chloride Formulation LLL: 140 mg/ml VEGF receptor fusion protein (e.g., aflibercept); 20 mM histidine, pH 5.8; 5% sucrose; 0.03% polysorbate 20; 50 mM lysine Formulation MMM: 140 mg/ml VEGF receptor fusion protein (e.g., aflibercept); 20 mM histidine, pH 5.8; 5% sucrose; 0.03% polysorbate 20; 50 mM sodium aspartate Formulation NNN: 140 mg/ml VEGF receptor fusion protein (e.g., aflibercept); 20 mM histidine, pH 5.8; 5% sucrose; 0.03% polysorbate 20; 50 mM sodium glutamate Formulation OOO: 140 mg/ml VEGF receptor fusion protein (e.g., aflibercept); 20 mM histidine, pH 5.8; 5% sucrose; 0.03% polysorbate 20; 50 mM sodium citrate; 50 mM arginine hydrochloride Formulation PPP: 140 mg/ml VEGF receptor fusion protein (e.g., aflibercept); 20 mM histidine, pH 5.8; 5% sucrose; 0.03% polysorbate 20; 50 mM glycine; 50 mM arginine hydrochloride Formulation QQQ: 140 mg/ml VEGF receptor fusion protein (e.g., aflibercept); 20 mM histidine, pH 5.8; 5% sucrose; 0.03% polysorbate 20; 50 mM sodium aspartate; 50 mM arginine hydrochloride Formulation RRR: 140 mg/ml VEGF receptor fusion protein (e.g., aflibercept); 20 mM histidine, pH 5.8; 5% sucrose; 0.03% polysorbate 20; 50 mM sodium glutamate; 50 mM arginine hydrochloride Formulation SSS: 140 mg/ml VEGF receptor fusion protein (e.g., aflibercept); 20 mM His, pH 5.8; 5% sucrose; 0.03% polysorbate 20; 10 mM L-arginine hydrochloride Formulation TTT: 140 mg/ml VEGF receptor fusion protein (e.g., aflibercept); 20 mM His, pH 5.8; 5% sucrose; 0.03% polysorbate 20; 100 mM L-arginine hydrochloride Formulation UUU: 30 mg/ml VEGF receptor fusion protein (e.g., aflibercept), 10% sucrose, 10 mM phosphate, 0.03% polysorbate 20, pH 6.2

Formulation VVV: 30 mg/ml VEGF receptor fusion protein (e.g., aflibercept), 20% sucrose, 10 mM phosphate, 0.03% polysorbate 20, pH 6.2

Formulation WWW: 60 mg/ml VEGF receptor fusion protein (e.g., aflibercept), 10% sucrose, 10 mM phosphate, 0.03% polysorbate 20, pH 6.2

Formulation XXX: 60 mg/ml VEGF receptor fusion protein (e.g., aflibercept), 20% sucrose, 10 mM phosphate, 0.03% polysorbate 20, pH 6.2

Formulation YYY: 120 mg/ml VEGF receptor fusion protein (e.g., aflibercept), 10% sucrose, 10 mM phosphate, 0.03% polysorbate 20, pH 6.2

Formulation ZZZ: 120 mg/ml VEGF receptor fusion protein (e.g., aflibercept), 20% sucrose, 10 mM phosphate, 0.03% polysorbate 20, pH 6.2

Formulation AAAA: 120 mg/ml VEGF receptor fusion protein (e.g., aflibercept), 10% sucrose, 10 mM phosphate, 0.03% polysorbate 20, 50 mM NaCl, pH 6.2

Formulation BBBB: 120 mg/ml VEGF receptor fusion protein (e.g., aflibercept), 20% sucrose, 10 mM phosphate, 0.03% polysorbate 20, 50 mM NaCl, pH 6.2

Formulation CCCC: 140 mg/ml VEGF receptor fusion protein (e.g., aflibercept), 10 mM sodium phosphate, 5% sucrose, 40 mM sodium chloride, 0.03% PS20, pH 6.2

Formulation DDDD: 80 mg/ml VEGF receptor fusion protein (e.g., aflibercept), 20 mM histidine-based buffer, 5% (w/v) sucrose, 0.03% (w/v) polysorbate 20, and 50 mM L-arginine monohydrochloride, with a pH of 5.8.

Formulation EEEE: 120.0 mg/ml VEGF receptor fusion protein (e.g., aflibercept) (e.g., +12 mg/ml), 20 mM histidine-based buffer (e.g., +2 mM), 5% (w/v) sucrose (e.g., +0.5%), 0.03% (w/v) polysorbate 20 (e.g., 0.02-0.04%), and 50 mM L-arginine monohydrochloride (e.g., +5 mM), with a pH of 5.8 (e.g., 5.6-6.0 or 5.5-6.1).

Formulation FFFF: 113.3 mg/ml VEGF receptor fusion protein (e.g., aflibercept) (e.g., 102-125 mg/ml), 20 mM histidine-based buffer (e.g., +2 mM), 5% (w/v) sucrose (e.g., +0.5%), 0.03% (w/v) polysorbate 20 (e.g., 0.02-0.04%), and 50 mM L-arginine monohydrochloride (e.g., +5 mM), with a pH of 5.8 (e.g., 5.6-6.0 or 5.5-6.1).

Formulation GGGG: 114.3 mg/ml VEGF receptor fusion protein (e.g., aflibercept) (e.g., 103-126 mg/ml), 10 mM histidine-based buffer (e.g., +1 mM), 5% (w/v) sucrose (e.g., +0.5%), 0.03% (w/v) polysorbate 20 (e.g., 0.02-0.04%), and 50 mM L-arginine monohydrochloride (e.g., +5 mM), with a pH of 5.8 (e.g., 5.6-6.0 or 5.5-6.1).

Formulation HHHH: 100.0 mg/ml VEGF receptor fusion protein (e.g., aflibercept) (e.g., +10 mg/ml), 20 mM histidine-based buffer (e.g., +2 mM), 5% (w/v) sucrose (e.g., +0.5%), 0.03% (w/v) polysorbate 20 (e.g., 0.02-0.04%), and 50 mM L-arginine monohydrochloride (e.g., +5 mM), with a pH of 5.8 (e.g., 5.6-6.0 or 5.5-6.1).

Formulation IIII: 133.3 mg/ml VEGF receptor fusion protein (e.g., aflibercept) (e.g., +13 mg/ml), 20 mM histidine-based buffer (e.g., +2 mM), 5% (w/v) sucrose (e.g., +0.5%), 0.03% (w/v) polysorbate 20 (e.g., 0.02-0.04%), and 50 mM L-arginine monohydrochloride (e.g., +5 mM), with a pH of 5.8 (e.g., 5.6-6.0 or 5.5-6.1).

Formulation JJJJ: 150 mg/ml aflibercept (e.g., aflibercept) (e.g., +15 mg/ml), 10 mM sodium phosphate, 8% (w/v) sucrose (e.g., +0.8%), 0.03% (w/v) polysorbate 20 (e.g., 0.02-0.04%) and 50 mM L-arginine hydrochloride, pH 6.2 (e.g., 6.0-6.4 or 5.9-6.5).

Formulation KKKK: 114.3 mg/ml VEGF receptor fusion protein (e.g., aflibercept) (e.g., +14 mg/ml), 20 mM histidine-based buffer (e.g., +2 mM), 5% (w/v) sucrose (e.g., +0.5%), 0.03% (w/v) polysorbate 20 (e.g., 0.02-0.04%), and 50 mM L-arginine monohydrochloride (e.g., +5 mM), with a pH of 5.8 (e.g., 5.6-6.0 or 5.5-6.1);

or any formulation which is set forth herein.

In an embodiment of the invention, the concentration of any formulation constituent (e.g., all constituents) listed above (e.g., any one of formulations A-KKKK) or which is discussed herein is ±about 3%, 5% or about 10% of the concentration specifically mentioned.

Methods of Manufacture

Embodiments herein include methods of manufacturing a pharmaceutical formulation of the present invention including a VEGF receptor fusion protein (e.g., any of formulations A-KKKK as set forth herein) comprising combining the components of the formulation into a single composition, and, optionally, introducing the formulation into a vessel or device e.g., a vial, or delivery device, e.g., a pre-filled syringe. The formulations, vials or devices that are the product of such methods are part of the present invention.

In an embodiment of the invention, the method of manufacturing a VEGF receptor fusion protein containing pharmaceutical formulation of the present invention (e.g., any of formulations A-KKKK as set forth herein) comprises the steps of culturing a host cell (e.g., Chinese hamster ovary cell) comprising one or more polynucleotides encoding a VEGF receptor fusion protein (e.g., aflibercept) in a culture medium and under conditions whereby the protein is expressed; and, purifying the protein from the host cell and/or culture medium and combining a portion of the protein with excipients of a pharmaceutical formulation as set forth herein. Again, the formulations, vials or devices that are the product of such methods are part of the present invention.

In an embodiment of the invention, a determination is made as to the amount and type of VEGF receptor fusion protein needed in the formulation to make it a high concentration and for its end-use. The same determination is made regarding the amount and type of buffer, the amount and type of surfactant, the amount and type of thermal stabilizer, and the inclusion, or specific exclusion, of a viscosity reducing agent. These components are combined and mixed, making sure that the formulation pH is at the desired value, e.g., between about 5.0 and about 6.8 (e.g., 5.8), and/or that the viscosity is at a desired value, e.g., about 6.0, 7.3, 11.5 or 12.0 cP at 20° C. In an embodiment of the invention, high concentration VEGF receptor fusion protein containing formulations can be sterilized and stored in a stable condition, e.g., for up to 24 or 36 months at 2° C. to 8° C. (e.g., 5° C.).

See, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.

Angiogenic Eye Disorders and Cancer

The pharmaceutical formulations of the present invention comprising VEGF receptor fusion proteins (e.g., any of pharmaceutical formulations A-KKKK) can be used in the treatment or prevention of any angiogenic eye disorder by administration of a therapeutically effective amount of VEGF receptor fusion protein in a formulation of the present invention to a subject in need thereof, e.g., by intravitreal injection. Angiogenic eye disorders herein refer to any disease of the eye which is caused by or associated with the growth or proliferation of blood vessels and/or by blood vessel leakage. Non-limiting examples of angiogenic eye disorders that are treatable or preventable using the formulations and methods herein, include:

age-related macular degeneration (wet),
macular edema,
macular edema following retinal vein occlusion,
retinal vein occlusion (RVO),
central retinal vein occlusion (CRVO),
branch retinal vein occlusion (BRVO),
diabetic macular edema (DME),
choroidal neovascularization (CNV),
iris neovascularization,
neovascular glaucoma,
post-surgical fibrosis in glaucoma,
proliferative vitreoretinopathy (PVR),
optic disc neovascularization,
corneal neovascularization,
retinal neovascularization,
vitreal neovascularization,
pannus,
pterygium,
vascular retinopathies,
diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in an subject that does not suffer from DME) and
Diabetic retinopathy in a patient who has diabetic macular edema (DME).

The pharmaceutical formulations of the present invention comprising VEGF receptor fusion proteins (e.g., any of pharmaceutical formulations A-KKKK) can be used in the treatment or prevention of any cancer by administration of a therapeutically effective amount of VEGF receptor fusion protein in a formulation of the present invention to a subject in need thereof, e.g., by intramuscular, intratumoral, subcutaneous or intravenous injection. Cancers include those whose growth, proliferation, survival and/or metastasis is dependent, to a degree, on angiogenesis. In an embodiment of the invention, the cancer is colorectal cancer, lung cancer, skin cancer, breast cancer, brain cancer, stomach cancer, renal cancer, prostate cancer, liver cancer or pancreatic cancer.

Thus, the present invention provides methods for treating or preventing an angiogenic eye disorder in a subject in need thereof comprising administering a therapeutically effective amount of VEGF receptor fusion protein (e.g., aflibercept) (e.g., about 4, 6, or 8.0, 8.1, 8.4 or 8.5 mg), e.g., in a pharmaceutical formulation according to the present invention, intraocularly, e.g., into the vitreous, of an eye of the subject. In an embodiment of the invention, both eyes are administered the VEGF receptor fusion protein. In an embodiment of the invention, therapeutically effective doses of the VEGF receptor fusion protein are administered about every 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks 18 weeks, 19 weeks, 20 weeks, 21 weeks, 22 weeks, 23 weeks or 24 weeks. In an embodiment of the invention, such methods of treatment or prevention are done in the absence of significant increases in blood pressure (systolic and/or diastolic) and/or the development of hypertension (e.g., Grade 1, Grade 2 or Grade 3) and/or abnormally high intraocular pressure in the subject. In an embodiment of the invention, the method includes the step of, following said administration, monitoring the subject for significant increases in blood pressure (systolic and/or diastolic) and/or the development of hypertension (e.g., Grade 1, Grade 2 or Grade 3) and/or abnormally high intraocular pressure.

Modes of Administration

The pharmaceutical formulations of the present invention which include a VEGF receptor fusion protein may be administered in accordance with known medically approved delivery systems. In embodiments herein, these delivery systems may include administering the formulations to the patient by ocular, intraocular, intrachoroidal, intravitreal or subconjunctival injection. Alternatively, pharmaceutical formulations of the present invention can also be administered to the patient by topical routes, e.g., eye drops, eye gels, eye ointments, and the like. Other possible routes of delivery for the formulations herein include intradermal, intramuscular, intraperitoneal, intravenous, subcutaneous, intranasal, epidural and oral.

In an embodiment of the invention, intravitreal injection of a pharmaceutical formulation of the present invention includes the step of piercing the eye with a syringe and needle (e.g., 30-gauge injection needle) containing the formulation and injecting the formulation (e.g., less than or equal to about 100 microliters; about 40, 50, 55, 56, 57, 57.1, 58, 60, 70 or 75 microliters) into the vitreous of the eye (e.g., with a sufficient volume as to deliver a therapeutically effective amount of VEGF receptor fusion protein, e.g., of about 4, 5, 6, 7, 8.0, 8.1, 8.2, 8.3, 8.4, 8.5, 8.6, 8.7, 8.8 or 8.9, 9, 10, 12, 14, 16, 18 or 20 mg VEGF receptor fusion protein). Optionally, the method includes the steps of administering a local anesthetic (e.g., proparacaine, lidocaine or tetracaine), an antibiotic (e.g., a fluoroquinolone), antiseptic (e.g., povidone-iodine) and/or a pupil dilating agent to the eye being injected. In an embodiment of the invention, a sterile field around the eye to be injected is established before the injection. In an embodiment of the invention, following intravitreal injection, the subject is monitored for elevations in intraocular pressure and/or blood pressure. In an embodiment of the invention, the other eye is also injected by the same procedure.

Amounts of VEGF Receptor Fusion Protein to be Administered

Each dose of high concentration VEGF receptor fusion protein to a subject over the course of a treatment may contain the same or substantially the same amount of fusion protein. Alternatively, the quantity of any one dose may be different or variable over a treatment course.

An effective or therapeutically effective amount of VEGF receptor fusion protein for treating or preventing cancer (e.g., which is mediated, at least in part, by angiogenesis) or an angiogenic eye disorder refers to the amount of the VEGF receptor fusion protein sufficient to cause the regression, stabilization or elimination of the cancer or angiogenic eye disorder, e.g., by regressing, stabilizing or eliminating one or more symptoms or indicia of the cancer or angiogenic eye disorder by any clinically measurable degree, e.g., with regard to an angiogenic eye disorder, by causing a reduction in or maintenance of diabetic retinopathy severity score (DRSS), by improving or maintaining vision (e.g., in best corrected visual acuity e.g., as measured by an increase in ETDRS letters), increasing or maintaining visual field and/or reducing or maintaining central retinal thickness and, with respect to cancer, stopping or reversing the growth, survival and/or metastasis of cancer cells in the subject. In an embodiment of the invention, an effective or therapeutically effective amount of VEGF receptor fusion protein for treating or preventing an angiogenic eye disorder is about 0.5 mg to about 10 mg or 0.5 mg to about 20 mg per dose, including: about 0.5 mg or more; or about 2 mg or more, e.g., about 2.1 mg; 2.2 mg; 2.3 mg; 2.4 mg; 2.5 mg; 2.6 mg; 2.7 mg; 2.8 mg; 2.9 mg; 3.0 mg; 3.1 mg; 3.2 mg; 3.3 mg; 3.4 mg; 3.5 mg; 3.6 mg; 3.7 mg; 3.8 mg; 3.9 mg; 4.0 mg; 4.1 mg; 4.2 mg; 4.3 mg; 4.4 mg; 4.5 mg; 4.6 mg; 4.7 mg; 4.8 mg; 4.9 mg; 5.0 mg; 5.1 mg; 5.2 mg; 5.3 mg; 5.4 mg; 5.5 mg; 5.6 mg; 5.7 mg; 5.8 mg; 5.9 mg; 6.0 mg; 6.1 mg; 6.2 mg; 6.3 mg; 6.4 mg; 6.5 mg; 6.6 mg; 6.7 mg; 6.8 mg; 6.9 mg; 7.0 mg; 7.1 mg; 7.2 mg; 7.3 mg; 7.4 mg; 7.5 mg; 7.6 mg; 7.7 mg; 7.8 mg; 7.9 mg; 8.0 mg; 8.1 mg; 8.2 mg; 8.3 mg; 8.4 mg; 8.5 mg; 8.6 mg; 8.7 mg; 8.8 mg; 8.9 mg; 9 mg; 9.1 mg; 9.2 mg; 9.3 mg; 9.4 mg; 9.5 mg; 9.6 mg; 9.7 mg; 9.8 mg; 9.9 mg, 10.0 mg, 10.1 mg; 10.2 mg; 10.3 mg; 10.4 mg; 10.5 mg; 10.6 mg; 10.7 mg; 10.8 mg; 10.9 mg; 11 mg; 11.1 mg; 11.2 mg; 11.3 mg; 11.4 mg; 11.5 mg; 11.6 mg; 11.7 mg; 11.8 mg; 11.9 mg; 12 mg; 12.1 mg; 12.2 mg; 12.3 mg; 12.4 mg; 12.5 mg; 12.6 mg; 12.7 mg; 12.8 mg; 12.9 mg; 13 mg; 13.1 mg; 13.2 mg; 13.3 mg; 13.4 mg; 13.5 mg; 13.6 mg; 13.7 mg; 13.8 mg; 13.9 mg; 14 mg; 14.1 mg; 14.2 mg; 14.3 mg; 14.4 mg; 14.5 mg; 14.6 mg; 14.7 mg; 14.8 mg; 14.9 mg; 15 mg; 15.1 mg; 15.2 mg; 15.3 mg; 15.4 mg; 15.5 mg; 15.6 mg; 15.7 mg; 15.8 mg; 15.9 mg; 16 mg; 16.1 mg; 16.2 mg; 16.3 mg; 16.4 mg; 16.5 mg; 16.6 mg; 16.7 mg; 16.8 mg; 16.9 mg; 17 mg; 17.1 mg; 17.2 mg; 17.3 mg; 17.4 mg; 17.5 mg; 17.6 mg; 17.7 mg; 17.8 mg; 17.9 mg; 18 mg; 18.1 mg; 18.2 mg; 18.3 mg; 18.4 mg; 18.5 mg; 18.6 mg; 18.7 mg; 18.8 mg; 18.9 mg; 19 mg; 19.1 mg; 19.2 mg; 19.3 mg; 19.4 mg; 19.5 mg; 19.6 mg; 19.7 mg; 19.8 mg; 19.9 mg; or 20 mg. In an embodiment of the invention, an effective or therapeutically effective amount of VEGF receptor fusion protein for treating or preventing cancer is about 4 mg/kg (e.g., intravenously). This dose may be administered, for example, every 2 weeks.

In an embodiment of the invention, a VEGF receptor fusion protein is administered in a volume sufficient to deliver the desired dose of fusion protein, e.g., as discussed above. In an embodiment of the invention, the volume delivered (e.g., for treating or preventing an angiogenic eye disorder, e.g., by intravitreal injection) is less than or equal to about 100 microliters (e.g., about any of the following volumes: 25 microliters; 26 microliters; 27 microliters; 28 microliters; 29 microliters; 30 microliters; 31 microliters; 32 microliters; 33 microliters; 34 microliters; 35 microliters; 36 microliters; 37 microliters; 38 microliters; 39 microliters; 40 microliters; 41 microliters; 42 microliters; 43 microliters; 44 microliters; 45 microliters; 46 microliters; 47 microliters; 48 microliters; 49 microliters; 50 microliters; 51 microliters; 52 microliters; 53 microliters; 54 microliters; 55 microliters; 56 microliters; 57 microliters; 58 microliters; 59 microliters; 60 microliters; 61 microliters; 62 microliters; 63 microliters; 64 microliters; 65 microliters; 66 microliters; 67 microliters; 68 microliters; 69 microliters; 70 microliters; 71 microliters; 72 microliters; 73 microliters; 74 microliters; 75 microliters; 76 microliters; 77 microliters; 78 microliters; 79 microliters; 80 microliters; 81 microliters; 82 microliters; 83 microliters; 84 microliters; 85 microliters; 86 microliters; 87 microliters; 88 microliters; 89 microliters; 90 microliters; 91 microliters; 92 microliters; 93 microliters; 94 microliters; 95 microliters; 96 microliters; 97 microliters; 98 microliters or 99 microliters).

In an embodiment of the invention, the formulation is administered (e.g., for treating or preventing an angiogenic eye disorder, e.g., by intravitreal injection) in a volume which is about 60 microliters or less, about 70 microliters or less or about 75 microliters or less or about 100 microliters or less. For example, in an embodiment of the invention, about 2, 4, 6, 8.0, 8.1, 8.0-8.1, 8.2, 8.3, 8.4, 8.5, 8.6, 8.7, 8.8 or 8.9, 9.0 or 10 mg of VEGF receptor fusion protein is administered in about 50, 60, 70 or 75 microliters.

The scope of the present invention also encompasses methods for delivering 0.5 or 2 mg of VEGF receptor fusion protein (e.g., for treating or preventing an angiogenic eye disorder, e.g., by intravitreal injection) in pharmaceutical formulation of the present invention in a low volume such as less than 50 μl (e.g., about 1, 5, 10, 17, 17.5, 18, 18.5, 20, 30, 40 or 45 μl).

The present invention also includes a composition including or consisting or consisting essentially of a "single dosage volume" of pharmaceutical formulation of the present invention, i.e., a volume containing a single dose of VEGF receptor fusion protein (e.g., aflibercept) in a pharmaceutical formulation of the present invention (e.g., about 50 μl or 60 μl, 70 μl or 75 μl or whatever volume contains about 4, 6, 8 or 10 mg of VEGF receptor fusion protein). As discussed below, a container (e.g., vial or injection device) comprising a single dosage volume, optionally including a small overfill volume of formulation, is also part of the present invention.

Containers and Injection Devices

High concentration VEGF receptor fusion protein formulations in accordance with embodiments herein (e.g., any of formulations A-KKKK) can be pre-packaged or pre-loaded in various useful containers and injection devices. Thus, the present invention includes containers and injection devices containing such formulations. In one embodiment herein, the container is a vial which may be sterile. In another embodiment herein, the container is a test tube which may be sterile. In an embodiment of the invention, an injection device (which may be sterile) is a syringe (e.g., a pre-filled syringe or autoinjector). In an embodiment of the invention, the injection device is an intravitreal implant, e.g., a refillable intravitreal implant.

A "pre-filled" syringe is a syringe which is filled with a formulation of the present invention prior to sale or use by the physician or patient.

"Sterile" herein refers to aseptic or free from substantially all, or all, living microorganisms and their spores.

Syringes as used herein include barrels made, for example, of glass or polymer, for example, cycloolefin as described in U.S. Patent Publication No. 2017/0232199, incorporated herein for all purposes, a plunger and a needle.

Containers and injection devices may be coated with silicone (e.g., silicone oil or baked-silicone (e.g., ≤40 μg or ≤100 μg)).

In an embodiment of the invention, a container or injection device is substantially metal-free or substantially tungsten-free or low-tungsten.

In an embodiment of the invention, the syringe contains one or more dose line graduations and/or is a dose metering system.

Containers in accordance with embodiments herein can hold the high concentration VEGF receptor fusion protein formulations. In some aspects, the container or injection device can include a label stating indications of use. In some instances, the container or injection device herein can include package inserts with instructions for use as described throughout this specification.

In other embodiments, a volume containing a single dose or multiple doses (e.g., 2 or more than 2) of a high concentration VEGF receptor fusion protein (e.g., wherein the dose is 2 mg, 4 mg, 6 mg, 8 mg or 10 mg of VEGF receptor fusion protein), as described above, can be pre-packaged into a container or injection device, e.g., a sterile syringe, for example, for storage until use. In one example, the volume in the container includes a single dose of VEGF receptor fusion protein optionally further including a small amount of overfill volume. Sterile, pre-loaded syringes can be maintained under storage conditions (e.g., 2° C.-8° C.), for example, for up to 12 months, 24 months or 36 months. Overfill is an excess volume that is meant to be sufficient to permit withdrawal and/or administration of the proper volume. In an embodiment of the invention, the container has a single dosage volume or multiple dosage volumes and about 5%-10% overfill volume.

Syringe sizes can be, for example, 0.3 cc, 0.5 cc or 1 cc, for example. Sterile syringes typically include a needle useful for ocular injection, typically about ½ inch, or 12.5 mm to 16 mm in length, and can be 29 gauge, 30 gauge, 31 gauge, 32 gauge or 33 gauge based on the patient and health care specialist preference. Other needle lengths and gauges can be used, as long as the needle is effective at accomplishing intravitreal injection.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

Additional Formulations

The present invention includes the following formulations comprising greater than 40 mg/ml VEGF receptor fusion protein (e.g., aflibercept or conbercept) and:

(a) a buffer including a histidine salt (e.g., histidine-HCl or histidine-acetate, for example, 10 mM to 50 mM) and having pH ranging from 5.7 to 6.2; a sugar (e.g., more than 6%, but not more than 10%) such as sucrose, trehalose, mannitol or glucose; a surfactant selected from the group consisting of polysorbate 20 and polysorbate 80 (e.g., 0% to 0.1%);

(b) a histidine containing buffer such as L-histidine/histidine hydrochloride (e.g., 10 mM); a non-ionic surfactant such as polysorbate 20 (e.g., 0.03%), an inorganic salt such as NaCl (e.g., 40 mM), and a carbohydrate such as sucrose (e.g., 5%), e.g. pH 6.0-6.5 (e.g., 6.2 or 6.5);

(c) citric acid (e.g., 5 mM, 10 mM, 15 mM, 20 mM, 25 mM or 30 mM), sucrose (e.g., 1%, 2%, 3%, 4%, 5%, 6%, 7%, 8%, 9% or 10%), arginine (e.g., 5 mM, 10 mM, 15 mM, 20 mM, 25 mM, 30 mM, 35 mM, 40 mM, 45 mM or 50 mM or 100 mM), and polysorbate 20 (e.g., 0.01%, 0.02%, 0.03%, 0.04%, 0.05%, 0.06%, 0.07%, 0.08%, 0.09% or 0.10%);

(d) a buffer such as phosphate, histidine, acetate, succinate, citrate, glutamate, and/or lactate (e.g., at 5-20 or 5-50 mM); a non-ionic surfactant such as a polysorbate (e.g., PS20 or PS80), a polyethylene glycol dodecyl ether, a poloxamer, Tetramethylbutyl)phenyl-polyethylene glycol, an alkylsaccharide or an alkylglycoside, a tonicifying agent such as a polyol or an amino acid, for example, sucrose, trehalose, sorbitol, mannitol, glycerol, proline, arginine, methionine, glycine, or lysine, wherein the formulation has a final osmolality of about 300 mOsm/kg, and wherein the concentration of chloride anion is less than about 10 mM; pH 5.0-6.5; or (e) 10 mM sodium phosphate, 40 mM sodium chloride, 0.03% polysorbate 20, and 5% sucrose, pH 6.2.

EXAMPLES

The following examples are provided for illustrative purposes only and are not intended to limit the scope of the invention. Efforts have been made to ensure accuracy with respect to numbers used, but some experimental errors and deviations should be accounted for. Any formulations set forth in these examples are part of the present invention.

In these examples, when an experiment is conducted at 2-8° C., the temperature is targeted to 5° C. with a tolerance of +3° C. variation.

Example 1: 80 mg/ml VEGF Receptor Fusion Protein Formulations Maintain

Potency, Physical Stability and Charge Over A 36 Month Period.

A series of four different formulations having 80 mg/ml VEGF receptor fusion protein (aflibercept) were tested for long term potency, physical stability and development of charge variants. The ingredient listing of each of the four formulations is shown in Table 1-1. Each formulation was evaluated for VEGF receptor fusion protein HMW species formation over the course of storage at 2° C. to 8° C. for 36 months, as well as for the percent main species by SE-UPLC. Each VEGF receptor fusion protein containing formulation was also evaluated using Imaged Capillary Isoelectric Focusing over the same course of time and temperature. Finally, each formulation's potency was tested by bioassay over the same course of time and temperature.

TABLE 1-1

| VEGF Receptor Fusion Protein Containing Formulations | | | | | | |
|---|---|---|---|---|---|---|
| Formulation | VEGFT (mg/mL) | Sodium phosphate (mM) | Histidine (mM) | Sucrose (w/v) | Polysorbate 20 (w/v) | Sodium Chloride (mM) | pH |
| F1 (B) | 80 | 10 | NA | 5 | 0.03 | 40 | 6.2 |
| F2 (H) | 80 | 10 | NA | 8 | 0.03 | 0 | 6.2 |
| F3 (D) | 80 | NA | 10 | 5 | 0.03 | 40 | 6.2 |
| F4 (G) | 80 | NA | 10 | 8 | 0.03 | 0 | 6.2 |

TABLE 1-2

| % HMW Species | | | | |
|---|---|---|---|---|
| Months at 2-8 C. | Formulation B Formulation 1 | Formulation H Formulation 2 | Formulation D Formulation 3 | Formulation G Formulation 4 |
| 0.0 | 1.7 | 1.6 | 1.6 | 1.3 |
| 1 | 2.1 | 2.1 | 1.6 | 1.7 |
| 2.0 | 2.3 | 2.2 | 1.8 | 1.8 |
| 3.0 | 2.4 | 2.5 | 2.0 | 2.1 |
| 6.0 | 2.9 | 2.8 | 2.0 | 2.3 |
| 9.0 | 3.1 | 3.0 | 2.2 | 2.4 |
| 12.0 | 2.8 | 3.0 | | 2.4 |
| 18.0 | 3.2 | 3.2 | 2.6 | 2.5 |
| 24.0 | 3.6 | 3.6 | 3.1 | 2.8 |
| 36.0 | 4.2 | 4.2 | 3.2 | 3.2 |

TABLE 1-3

| % Main Peak | | | | |
|---|---|---|---|---|
| Months at 2-8 C. | Formulation B Formulation 1 | Formulation H Formulation 2 | Formulation D Formulation 3 | Formulation G Formulation 4 |
| 0.0 | 98.4 | 98.4 | 98.4 | 98.8 |
| 1 | 97.9 | 98.0 | 98.4 | 98.3 |
| 2.0 | 97.7 | 97.8 | 98.2 | 98.2 |
| 3.0 | 97.7 | 97.5 | 98.0 | 98.0 |
| 6.0 | 97.1 | 97.2 | 97.9 | 97.7 |
| 9.0 | 96.9 | 97.0 | 97.8 | 97.6 |
| 12.0 | 97.2 | 97.0 | | 97.4 |
| 18.0 | 96.8 | 96.8 | 97.4 | 97.5 |
| 24.0 | 96.5 | 96.4 | 96.8 | 97.2 |
| 36.0 | 95.7 | 95.7 | 96.8 | 96.8 |

TABLE 1-4

| | % Acidic Species | | | |
|---|---|---|---|---|
| Months at 2-8 C. | Formulation B Formulation 1 | Formulation H Formulation 2 | Formulation D Formulation 3 | Formulation G Formulation 4 |
| 0.0 | 15.8 | 15.1 | 16.0 | 15.2 |
| 12 | 15.6 | 15.9 | NP | 16.0 |
| 24.0 | 16.0 | 17.1 | 16.2 | 16.9 |
| 36.0 | 16.9 | 17.4 | 17.2 | 17.6 |

TABLE 1-5

| | % Main Species | | | |
|---|---|---|---|---|
| Months at 2-8 C. | Formulation B Formulation 1 | Formulation H Formulation 2 | Formulation D Formulation 3 | Formulation G Formulation 4 |
| 0.0 | 78.9 | 79.1 | 79.2 | 79.9 |
| 12 | 79.3 | 79.3 | NP | 79.7 |
| 24.0 | 79.3 | 78.5 | 79.5 | 79.3 |
| 36.0 | 78.6 | 78.1 | 78.7 | 78.6 |

Figure 1A:
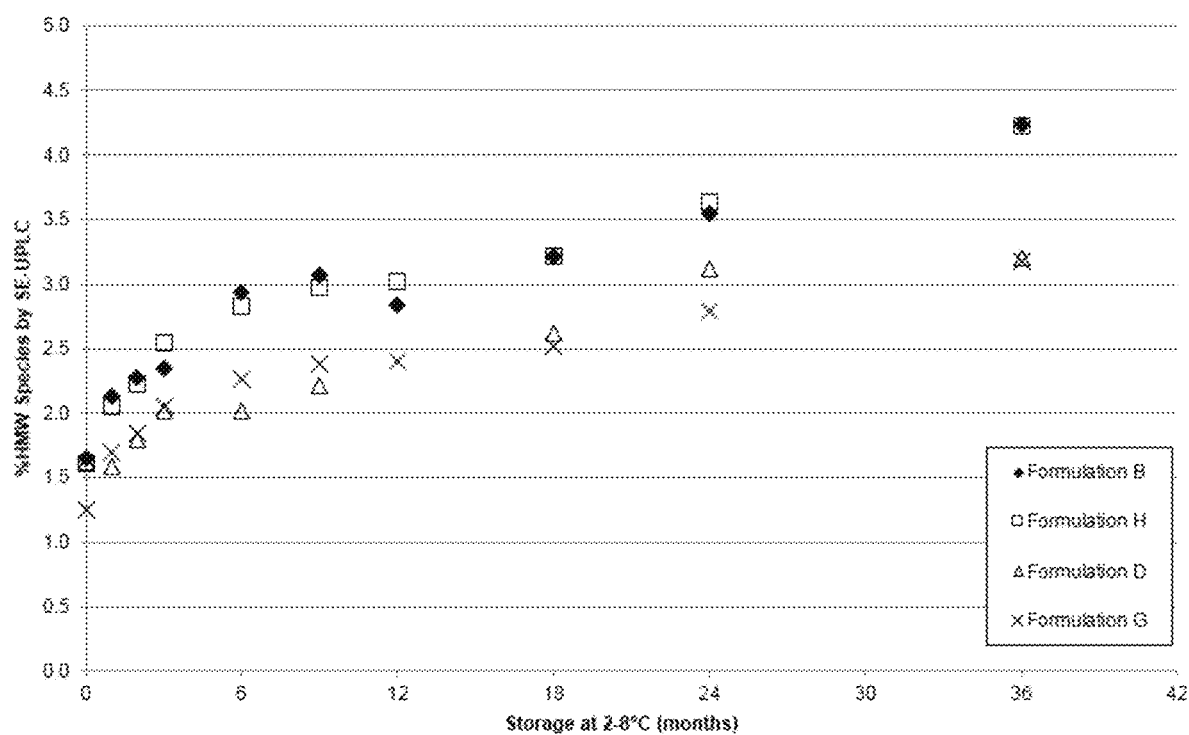
FIG. 1A is a graph determining VEGF receptor fusion protein (aflibercept) stability in four different formulations (B, H, D and G) over the course of 36 months at 2° C. to 8° C. VEGF receptor fusion protein stability was tested using size-exclusion ultra-performance liquid chromatography (SE-UPLC) to identify formation of high molecular weight (HMW) species (a sign of protein degradation).
Figure 1B:
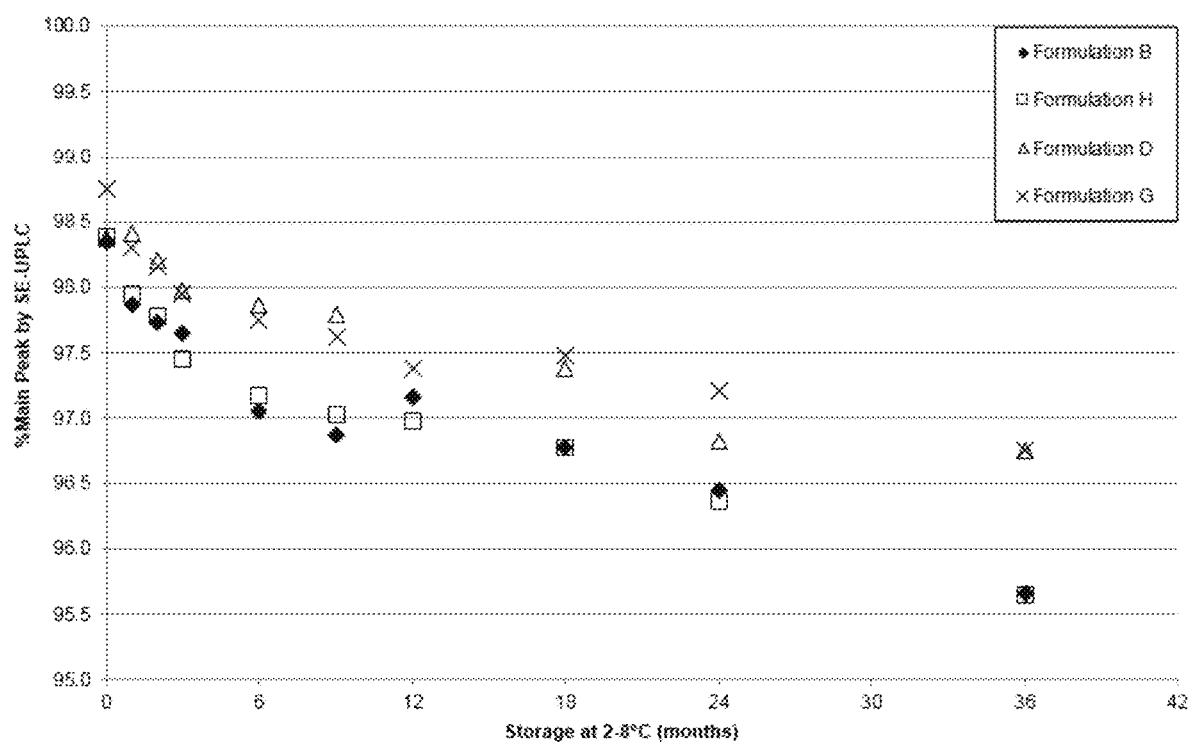
FIG. 1B is also a graph determining VEGF receptor fusion protein (aflibercept) stability in four formulations (B, H, D and G) over the course of 36 months at 2° C. to 8° C. VEGF receptor fusion protein stability was tested using SE-UPLC to identify the percent of the main species in each formulation.

Data is shown in FIGS. 1A, 1B, 1C and 1D. FIG. 1A shows the percent of VEGF receptor fusion protein HMW species formed for each of the four formulations. VEGF TRAP shows a slightly slower rate of HMW species formation when the formulation is histidine-based, as compared to sodium phosphate. As shown in FIG. 1A, the % HMW species after storage at 2° to 8° C. for 36 months increased by 2.6% in sodium phosphate formulations (Formulations 1 and 2), as compared to the 1.6 to 1.9% increase in histidine buffers (Formulations 3 and 4). The data was confirmed, as shown in FIG. 1B, where SE-UPLC was used to identify the percent of the VEGF receptor fusion protein main species present over the same time frame and temperature range. As a comparison point, assays were run on the current EYLEA® formulation (40 mg/ml) having 10 mM sodium phosphate, which showed a 1.2% increase in the % HMW species after storage at 2° to 8° C. for 36 months (not shown). In addition, each of the four 80 mg/ml VEGF TRAP formulations was tested for potency and compared to EYLEA® activity (not shown). Potency was maintained by bioassay for all four formulations as well as EYLEA®. These data show that formulations herein are able to maintain VEGF receptor fusion protein stability comparable to EYLEA®.

Figure 1C:
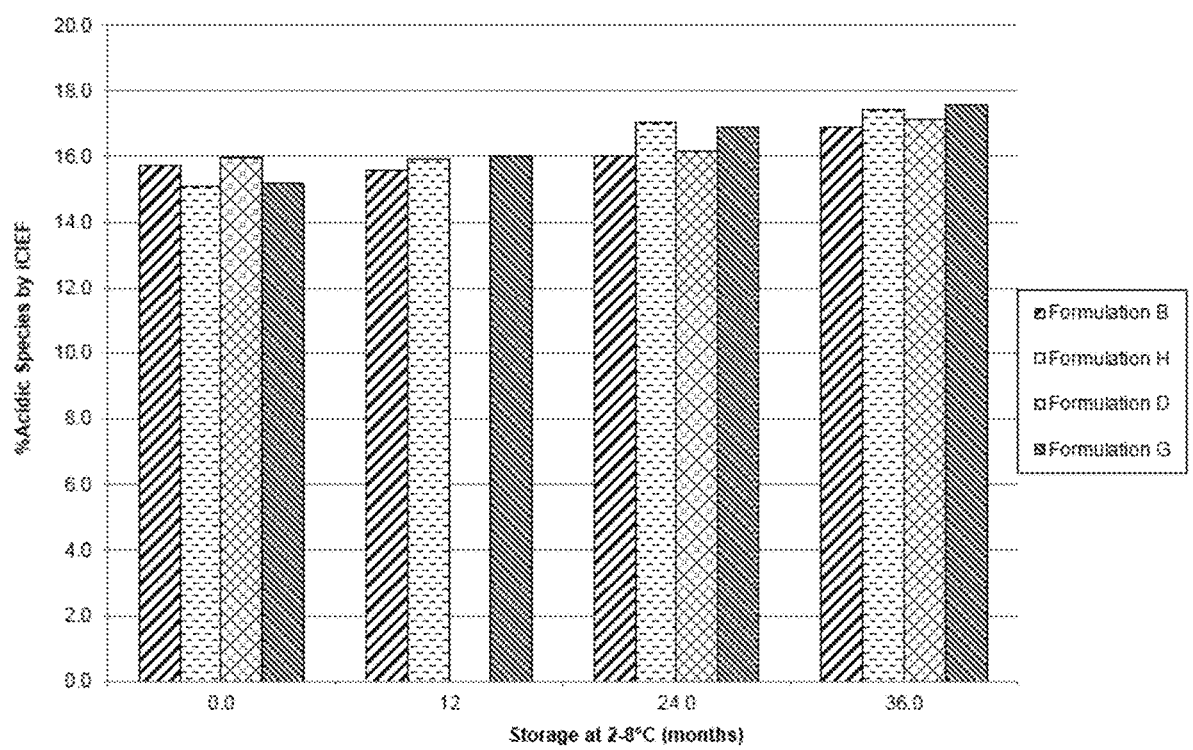
FIG. 1C is a bar graph showing formation of VEGF receptor fusion protein charge variants in four formulations (B, H, D and G) over the course of 36 months at 2° C. to 8° C. The level of acidic species was tested at manufacture (0.0), 12 months, 24 months and 36 months using imaged capillary isoelectric focusing (iCIEF).
Figure 1D:
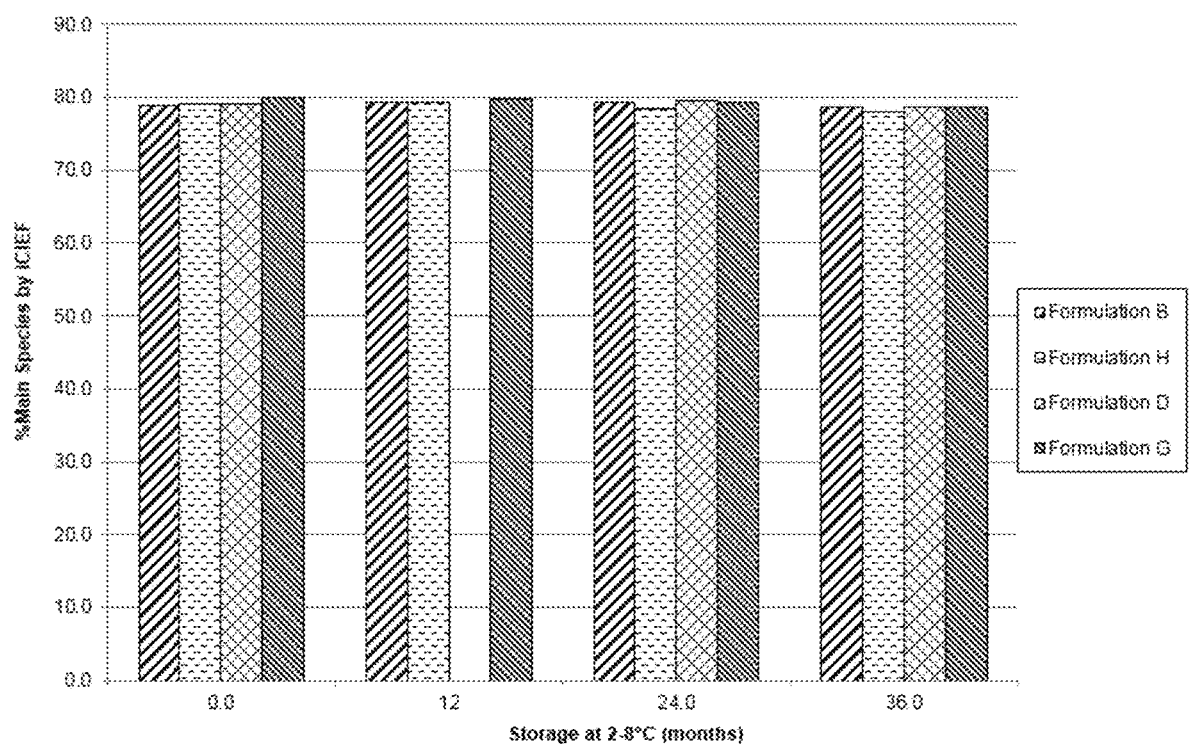
FIG. 1D is a bar graph showing formation of VEGF receptor fusion protein charge variants in four formulations (B, H, D and G) over the course of 36 months at 2° C. to 8° C. Identification of the main species was tested at manufacture (0.0), 12 months, 24 months and 36 months using iCIEF.

Referring to FIGS. 1C and 1D, the percent of VEGF TRAP charge variants formed after storage at 2° to 8° C. for 36 months was also tested. FIG. 1C shows that the VEGF TRAP in Formulations 1-4 showed no meaningful change in percent acidic species over the course of 36 months, and FIG. 1D shows the same finding for percent main species over the course of 36 months. The finding that the VEGF TRAP maintained charge variant species during storage shows that the quality of the VEGF TRAP was maintained, and processes like deamination, N-terminal pyroglutamate formation, isomerization, aggregation, etc. did not occur over the course of the storage parameters.

The data in Example 1 shows that formulations having double the VEGF TRAP concentration found in EYLEA®, can maintain physical stability, quality and potency over the course of 36 months at 2° to 8° C. Further, although all four formulations showed similar potency over the period, histidine containing formulations resulted in a slightly smaller increase in HMW species formation (sign of protein degradation), showing that under some circumstances, histidine may be a buffer of choice. However, the findings for both histidine and phosphate based buffers showed excellent stability over the course of the study.

Example 2: 150 mg/ml VEGF TRAP Stability in Sodium Phosphate Buffer/Sucrose Formulations Two sodium phosphate formulations were tested for physical stability of 150 mg/ml VEGF Trap (aflibercept) at 37° C. for 28 days. The ingredient listing of each of the two formulations is shown in Table 2-1. Each formulation was evaluated for HMW species formation over the course of storage at 37° C. for the 28 days as well as for the percent main species by SE-UPLC.

TABLE 2-1

| VEGF Receptor Fusion Protein (aflibercept) Containing Formulations for Example 2 | | | | | | |
|---|---|---|---|---|---|---|
| Formulation | VEGFT (mg/mL) | Sodium phosphate (mM) | Sucrose (w/v) | Polysorbate 20 (w/v) | Arginine-HCl (mM) | pH |
| F1 (T) | 150 | 10 | 8% | 0.03 | N/A | 6.2 |
| F2 (JJJJ) | 150 | 10 | 8% | 0.03 | 50 | 6.2 |

TABLE 2-2

| | % HMW Species | |
|---|---|---|
| Days at 37 C. | 10 mM Sodium Phosphate, 8% Sucrose, 0.03% Polysorbate 20, pH 6.2 Phosphate | 10 mM Sodium Phosphate, 8% Sucrose, 0.03% Polysorbate 20, 50 mM L-Arginine Monohydrochloride, pH 6.2 Phosphate-Arginine |
| 0.0 | 2.4 | 1.9 |
| 7 | 6.4 | 6.1 |
| 14.0 | 8.4 | 8.3 |
| 21.0 | 10.4 | 10.5 |
| 28.0 | 12.2 | 12.5 |

TABLE 2-3

| | % Main Peak | |
|---|---|---|
| Days at 37 C. | 10 mM Sodium Phosphate, 8% Sucrose, 0.03% Polysorbate 20, pH 6.2 Phosphate | 10 mM Sodium Phosphate, 8% Sucrose, 0.03% Polysorbate 20, 50 mM L-Arginine Monohydrochloride, pH 6.2 Phosphate-Arginine |
| 0.0 | 97.6 | 98.1 |
| 7 | 93.6 | 93.9 |
| 14.0 | 91.0 | 91.1 |
| 21.0 | 88.9 | 89.0 |
| 28.0 | 87.1 | 86.9 |

Figure 2A:
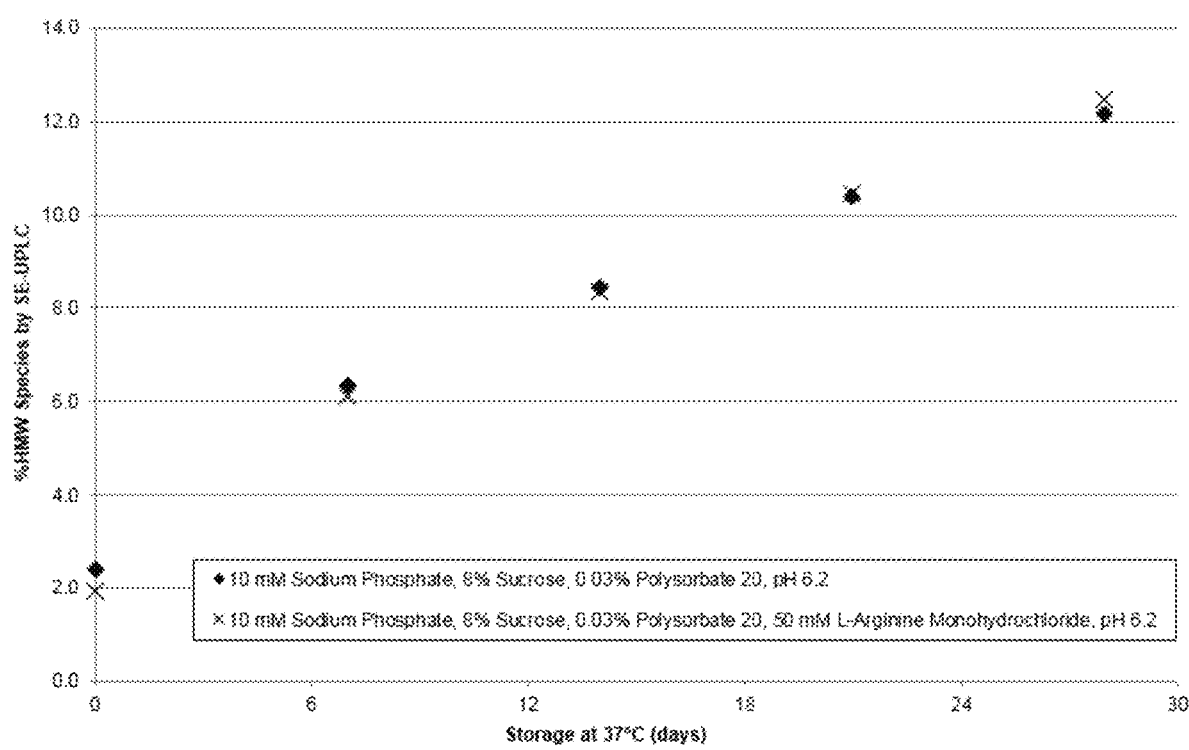
FIG. 2A is a graph showing 150 mg/ml VEGF receptor fusion protein (aflibercept) stability in a 10 mM sodium phosphate, 8% (w/v) sucrose and 0.03% polysorbate 20 (w/v) formulation pH6.2 with and without L-arginine monohydrochloride over the course of 28 days at 37° C. VEGF receptor fusion protein stability was tested using SE-UPLC to identify formation of HMW species.
Figure 2B:
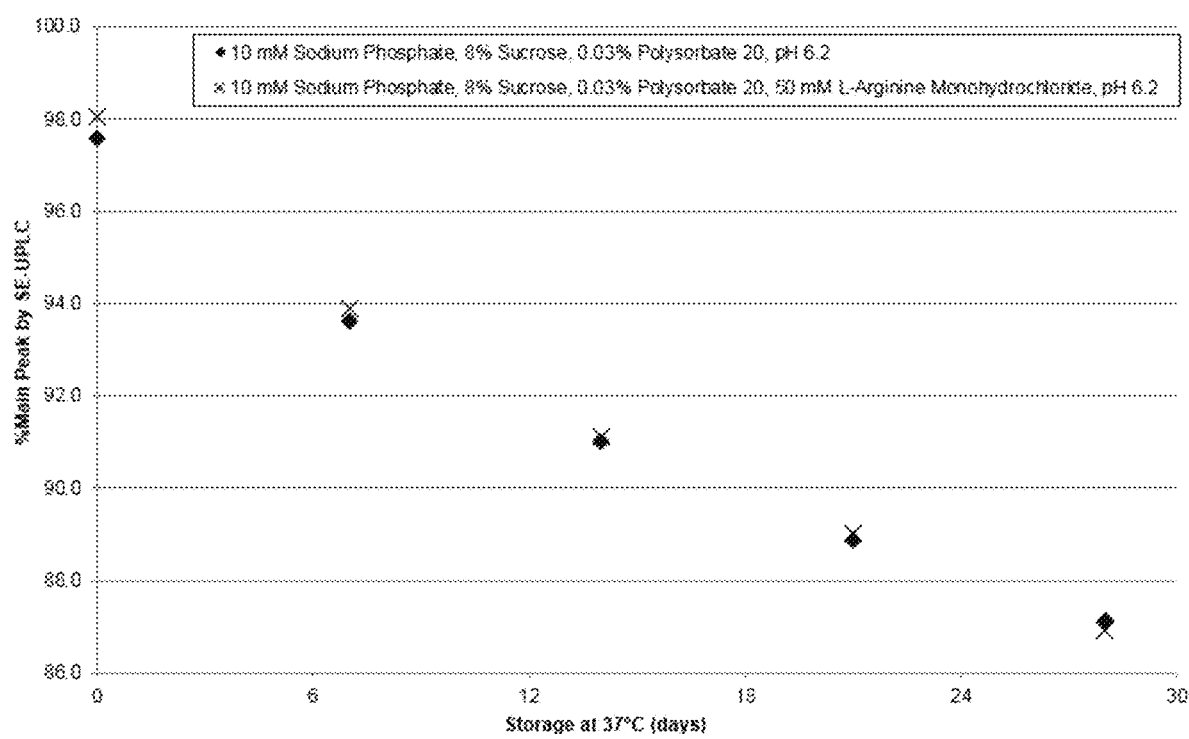
FIG. 2B is a graph showing 150 mg/ml VEGF receptor fusion protein stability in a 10 mM sodium phosphate, 8% sucrose (w/v) and 0.03% polysorbate 20 (w/v) formulation pH6.2 with and without L-arginine monohydrochloride over the course of 28 days at 37° C. VEGF receptor fusion protein stability was tested using SE-UPLC to identify the percent of the main species in each formulation.

FIG. 2A shows that there was no meaningful difference of % HMW species formed between the two formulations during storage at 37° C. for 28 days, which as confirmed by the percent of main species by SE-UPLC (FIG. 2B). There was no change in the appearance, turbidity or pH of the two formulations over the course of the 28 days (not shown).

The results were then compared to formulations that included 40 mg/ml EYLEA®, and Formulation 1 from Example 1 (80 mg/ml VEGF TRAP in sodium phosphate buffer). As expected, the 150 mg/ml VEGF TRAP formulations showed a higher percent of HMW species formation as compared to the EYLEA® formulation, and a somewhat higher percent of HMW species formation as compared to Formulation 1 of Example 1.

Further testing was performed on high concentration VEGF TRAP containing formulations, and histidine containing formulations showed better protection of these molecules than did formulations based in sodium phosphate. Further, inclusion of sodium chloride into each of the tested formulations actually caused destabilization of the VEGF TRAP at 37° C. The data in Example 2 shows that even at high concentrations of 150 mg/ml VEGF receptor fusion protein, and fairly extreme temperature storage, the formulations herein provide excellent protection for physical stability.

Example 3: Pharmaceutically Acceptable Formulation Viscosity can be Attained for 150 mg/ml VEGF TRAP A number of VEGF Trap (aflibercept) containing formulations were tested for their viscosity behavior. Formulations having from between 10 mg/ml to 160 mg/ml VEGF Trap were tested in the presence and absence of various viscosity reducing agents.

Figure 3A:
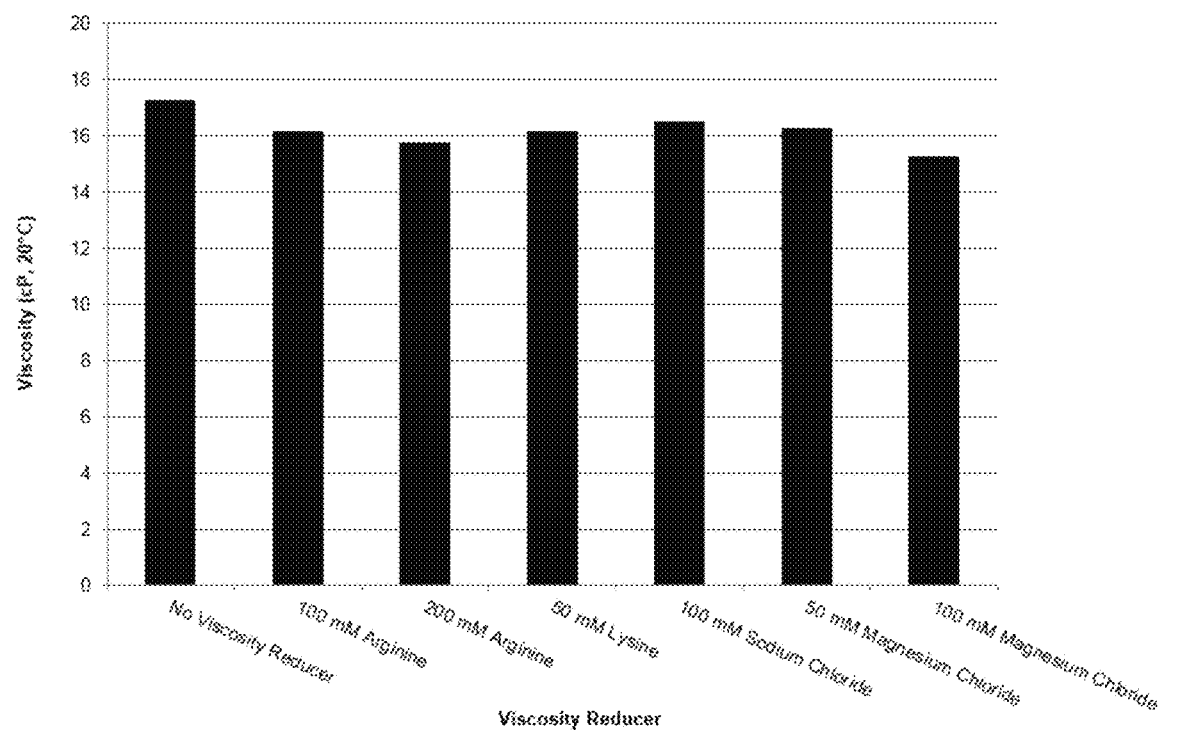
FIG. 3A is a bar graph showing viscosity of 10 mM sodium phosphate buffered formulations having 155 mg/ml VEGF receptor fusion protein and no salt, 100 mM arginine, 200 mM arginine, 50 mM lysine, 200 mM lysine, 50 mM sodium chloride or 100 mM sodium chloride. Viscosity was measured in cP at 20° C.
Figure 3B:
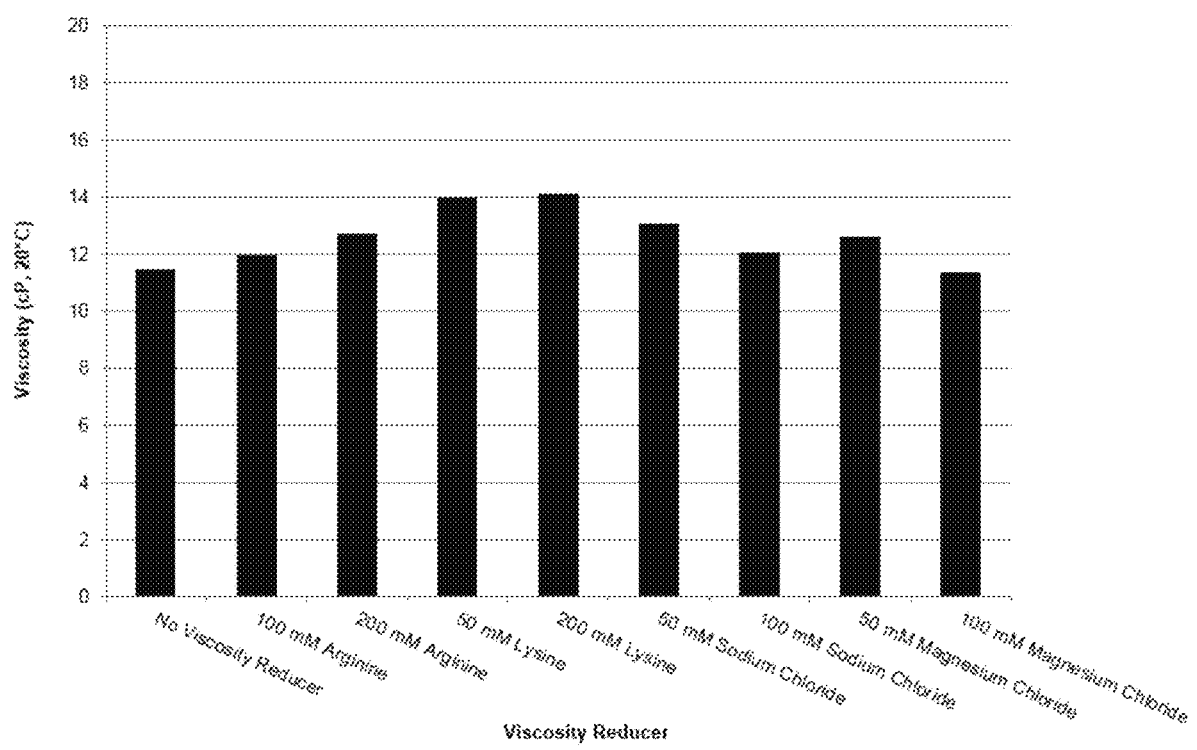
FIG. 3B is a bar graph showing viscosity of 10 mM histidine buffered formulations having 155 mg/ml VEGF receptor fusion protein and no salt, 100 mM arginine, 200 mM arginine, 50 mM lysine, 200 mM lysine, 50 mM sodium chloride or 100 mM sodium chloride. Viscosity was measured in cP at 20° C.

FIG. 3A shows formulations having 155 mg/ml VEGF Trap in 10 mM sodium phosphate buffer, 5% sucrose and a pH of 6.2 in combination with no inorganic salt, arginine, lysine, sodium chloride and magnesium chloride showed little difference in viscosity. In each case viscosity was measured in cP at 20° C. A range of viscosity between about 17 cP (no inorganic salt) and 15 cP (100 mM magnesium chloride) was observed, with little variation between which viscosity reducing agent was used, or with the presence of a viscosity reducing agent at all. FIG. 3B shows a similar series of formulations, except that the base buffer is 10 mM histidine and pH 5.8. Here, the lack of any inorganic salt provided a formulation with a viscosity of 11.5 cP, and 50 mM lysine a viscosity of 14 cP. The histidine containing buffer provided excellent viscosity, one in line with other low-concentration biologic injectables.

Figure 3C:
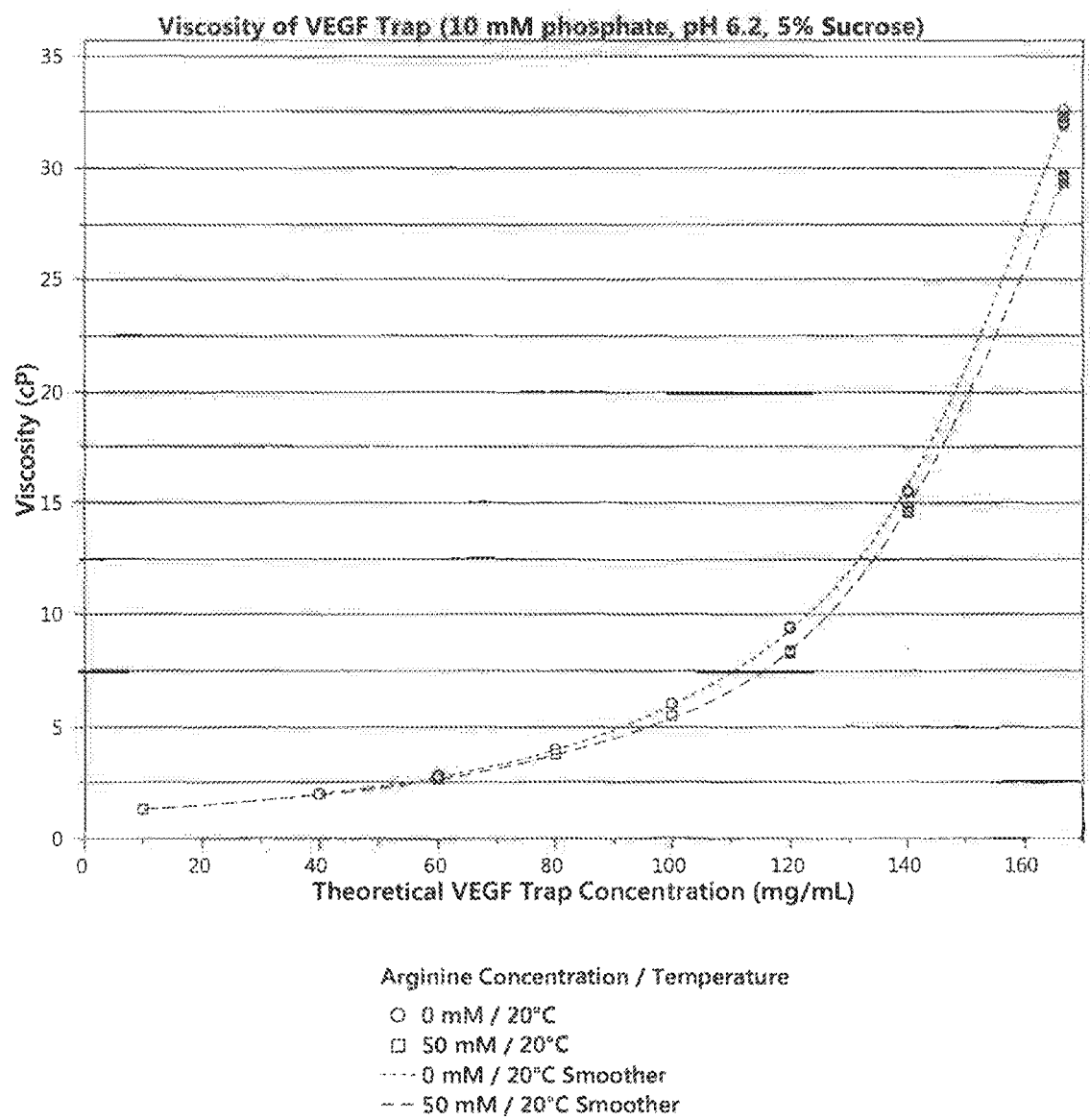
FIG. 3C is a graph showing viscosity of various concentrations of VEGF receptor fusion protein under different formulation conditions (with or without 50 mM arginine hydrochloride). Viscosity was measured in cP at 20° C.

FIG. 3C shows viscosity of VEGF Trap between the concentrations of 10 mg/ml and 160 mg/ml, with 10 mM sodium phosphate, 5% sucrose at a pH of 6.2 in the absence of arginine, and in 50 mM of arginine hydrochloride. Inclusion of the viscosity reducing agent resulted in similar viscosities for all VEGF Trap concentrations tested. As shown in FIGS. 3A and 3B, the viscosity reducing agent had little positive effect on the formulation viscosity, even at higher protein concentrations. This is a surprising result, as arginine and other viscosity reducing agents have previously been shown to have beneficial properties on high concentration protein viscosity.

TABLE 3-1

Viscosity-Phosphate formulations (cP at 20° C.)

| Buffer Composition | 10 mM Sodium Phosphate, 5% Sucrose, pH 6.2 |
|---|---|
| No Viscosity Reducer | 17.3 |
| 100 mM Arginine | 16.2 |
| 200 mM Arginine | 15.8 |
| 50 mM Lysine | 16.2 |
| 100 mM Sodium Chloride | 16.5 |
| 50 mM Magnesium Chloride | 16.3 |
| 100 mM Magnesium Chloride | 15.3 |

TABLE 3-2

Viscosity-Histidine formulations (cP at 20° C.)

| Buffer Composition | 10 mM Histidine, pH 5.8 |
|---|---|
| No Viscosity Reducer | 11.5 |
| 100 mM Arginine | 12.0 |
| 200 mM Arginine | 12.7 |
| 50 mM Lysine | 14.0 |
| 200 mM Lysine | 14.1 |
| 50 mM Sodium Chloride | 13.1 |
| 100 mM Sodium Chloride | 12.1 |
| 50 mM Magnesium Chloride | 12.6 |
| 100 mM Magnesium Chloride | 11.4 |

Example 4: Arginine Hydrochloride Improves Stability of 150 mg/ml VEGF TRAP in Sodium Phosphate Buffer/Sucrose Formulations Two sodium phosphate formulations were tested for physical stability of 150 mg/ml VEGF Trap (aflibercept) at 2-8° C. for 12 months. The ingredient listing of each of the two formulations is shown in Table 4-1. Formulation 2 further includes 50 mM arginine hydrochloride. Each formulation was evaluated for HMW species formation over the course of storage at 37° C. for the 12 months as well as for the percent main species by SE-UPLC.

TABLE 4-1

VEGF Receptor Fusion Protein (aflibercept) Containing Formulations for Example 3

| Formulation | VEGFT (mg/mL) | Sodium phosphate (mM) | Sucrose (w/v) | Polysorbate 20 (w/v) | pH | Arginine Hydrochloride (mM) |
|---|---|---|---|---|---|---|
| F1 (T) | 150 | 10 | 8% | 0.03 | 6.2 | 0 |
| F2 (JJJJ) | 150 | 10 | 8% | 0.03 | 6.2 | 50 |

Figure 4A:
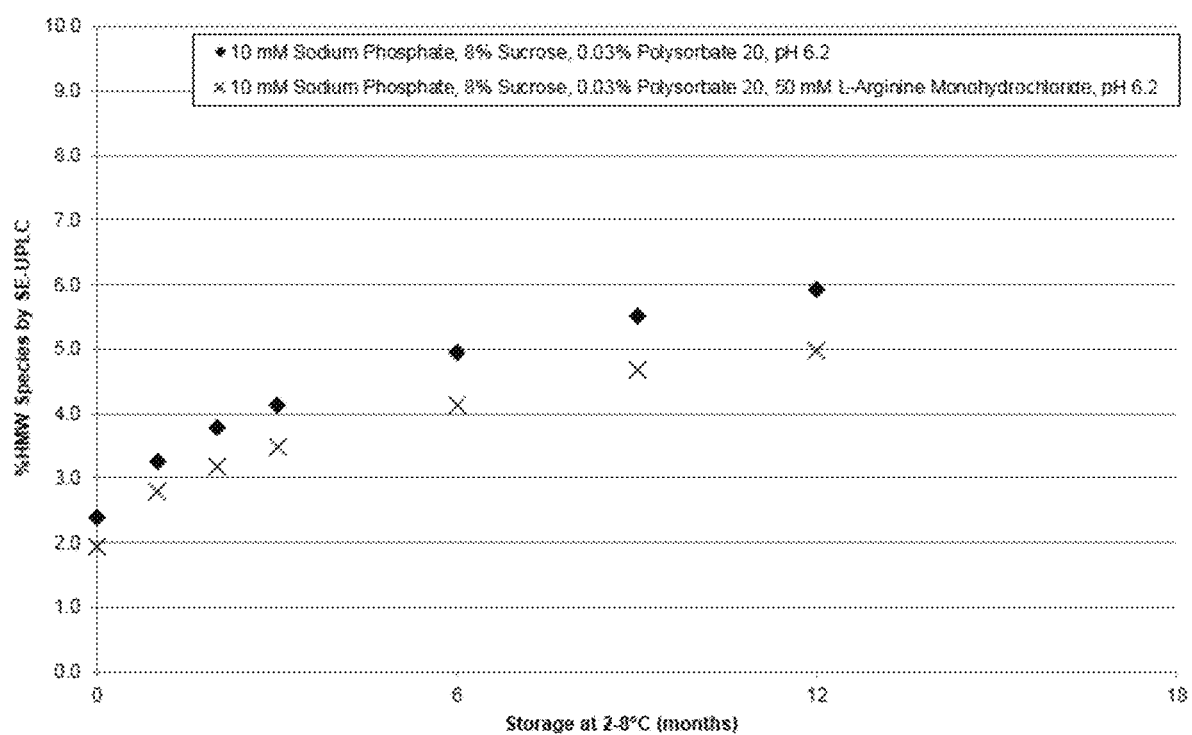
FIG. 4A is a graph showing 150 mg/ml VEGF receptor fusion protein stability in 10 mM sodium phosphate, 8% (w/v) sucrose, and 0.03% (w/v) polysorbate 20, pH6.2 with and without 50 mM L-arginine monohydrochloride over 12 months at 5° C. The VEGF receptor fusion protein was at 150 mg/ml. VEGF receptor fusion protein stability was tested using SE-UPLC to identify formation of HMW species.
Figure 4B:
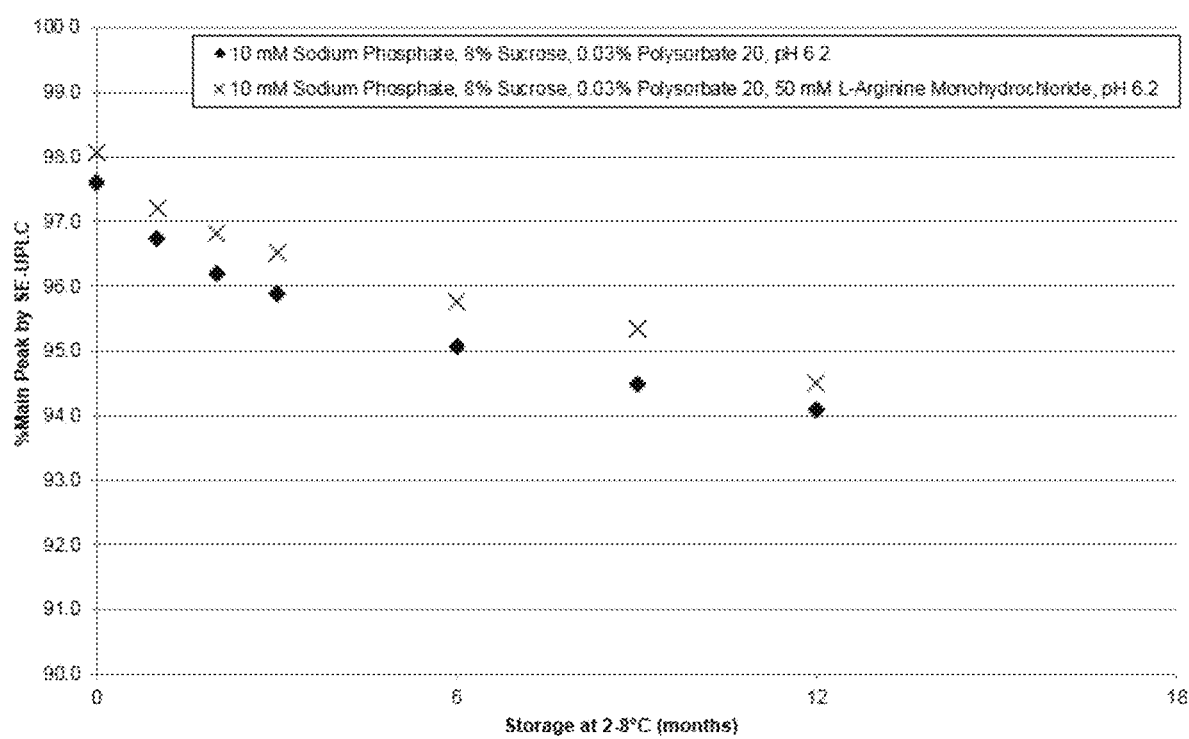
FIG. 4B is a graph showing 150 mg/ml VEGF receptor fusion protein stability in 10 mM sodium phosphate, 8% (w/v) sucrose, and 0.03% (w/v) polysorbate 20, pH6.2 with and without 50 mM L-arginine monohydrochloride over 12 months at 5° C. The VEGF receptor fusion protein was at 150 mg/ml. VEGF receptor fusion protein stability was tested using SE-UPLC to identify the percent of the main species in each formulation.

FIG. 4A shows that inclusion of 50 mM arginine hydrochloride to the formulation improved the VEGF TRAP physical stability. This stabilizing attribute on the VEGF TRAP was confirmed in FIG. 4B, where the percent main species remains higher for the VEGF TRAP in the presence of 50 mM arginine hydrochloride. This data shows that there are situations under which addition of arginine hydrochloride provides a stabilizing effect to the stored VEGF TRAP. Tabulated size-exclusion chromatography data are set forth in Table 4-2 and 4-3.

TABLE 4-2

% HMW Species

| Months at 2-8 C. | 10 mM Sodium Phosphate, 8% Sucrose, 0.03% Polysorbate 20, pH 6.2 | 10 mM Sodium Phosphate, 8% Sucrose, 0.03% Polysorbate 20, 50 mM L-Arginine Monohydrochloride, pH 6.2 |
|---|---|---|
| 0.0 | 2.4 | 1.9 |
| 1 | 3.3 | 2.8 |
| 2.0 | 3.8 | 3.2 |
| 3.0 | 4.1 | 3.5 |
| 6.0 | 4.9 | 4.1 |
| 9.0 | 5.5 | 4.7 |
| 12.0 | 5.9 | 5.0 |

TABLE 4-3

% Main Peak

| Months at 2-8 C. | 10 mM Sodium Phosphate, 8% Sucrose, 0.03% Polysorbate 20, pH 6.2 | 10 mM Sodium Phosphate, 8% Sucrose, 0.03% Polysorbate 20, 50 mM L-Arginine Monohydrochloride, pH 6.2 |
|---|---|---|
| 0.0 | 97.6 | 98.1 |
| 1 | 96.8 | 97.2 |
| 2.0 | 96.2 | 96.8 |
| 3.0 | 95.9 | 96.5 |
| 6.0 | 95.1 | 95.8 |
| 9.0 | 94.5 | 95.3 |
| 12.0 | 94.1 | 94.5 |

Figure 5:
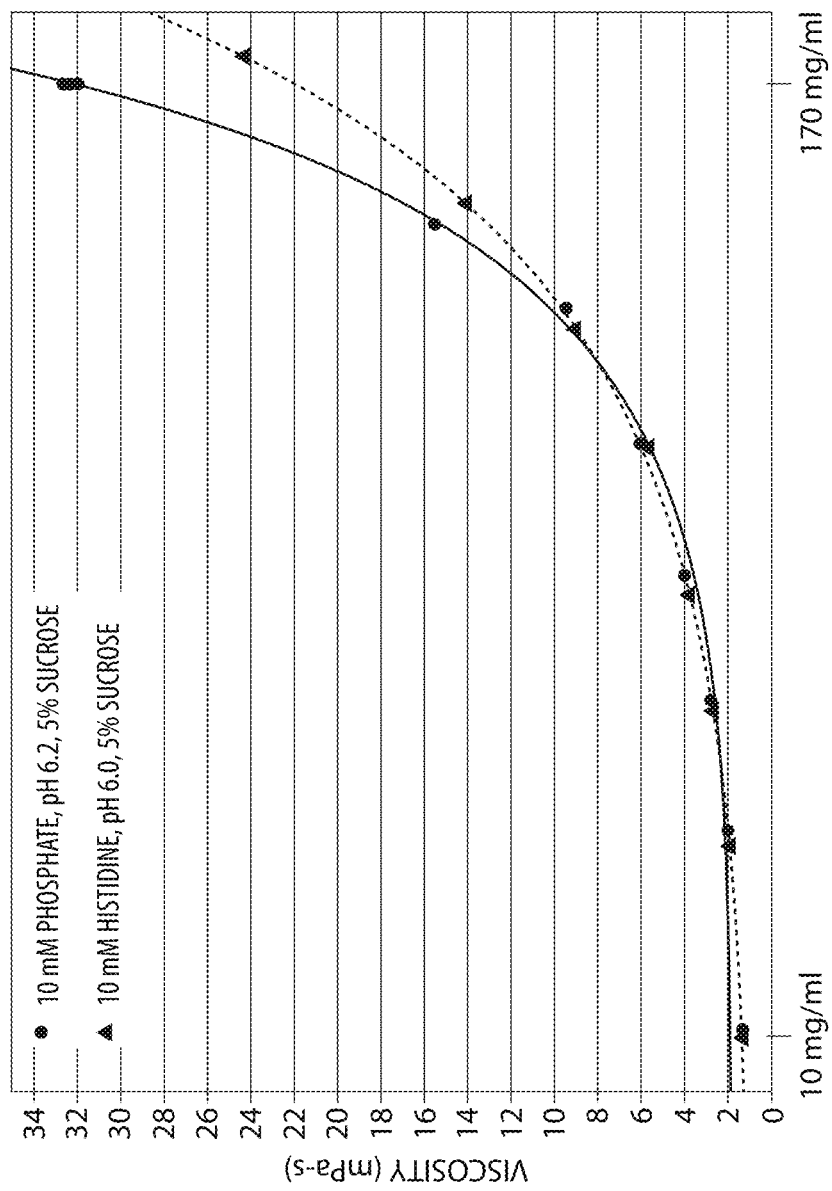
FIG. 5 is a graph that shows viscosity of formulations under two buffer conditions at 20° C., 10 mM phosphate buffer or 10 mM histidine buffer. The VEGF receptor fusion protein concentration is varied from 10 mg/ml to 170 mg/ml. Viscosity was measured in mPa-S.

Example 5: Viscosity of 10 mg/ml to 170 mg/ml VEGF TRAP in Histidine and Phosphate Buffers FIG. 5 showed that 10 mM phosphate buffer and 10 mM histidine buffer both had highly useful viscosities for a range of VEGF Trap (aflibercept) concentrations. At higher VEGF Trap concentrations, the histidine buffer showed an improvement in viscosity (relative to phosphate). Viscosity was measured at 20° C.

Figure 6:
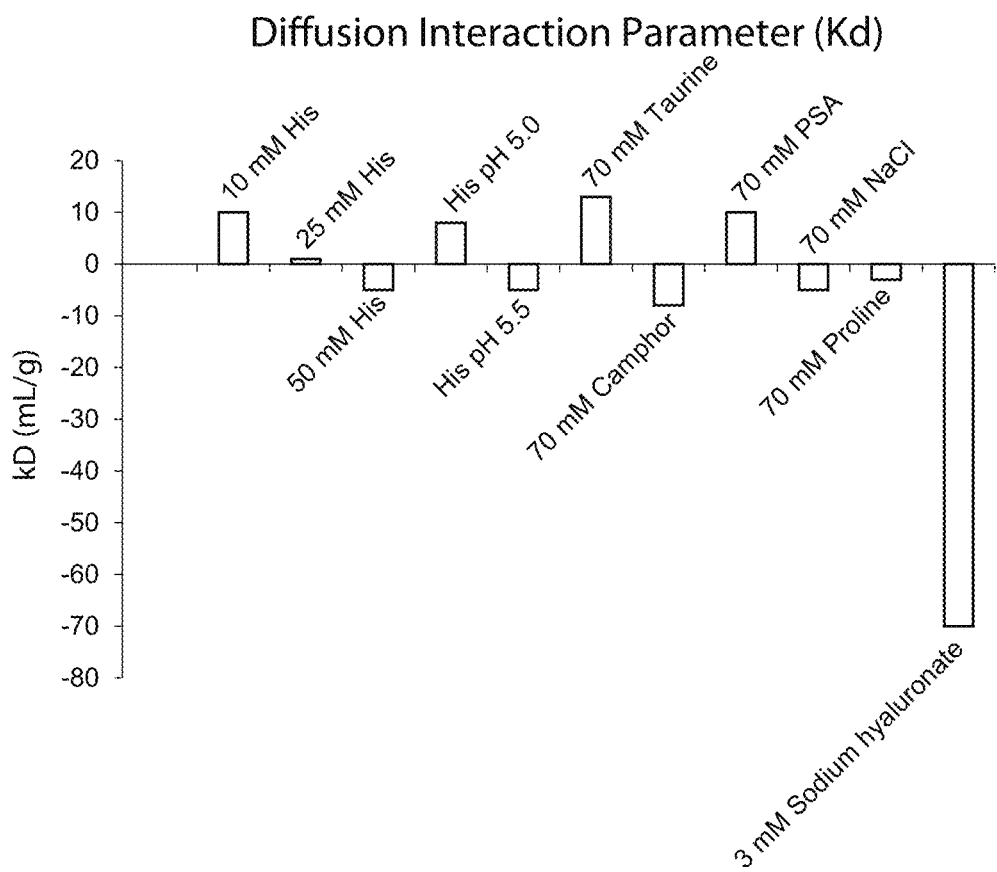
FIG. 6 shows a dynamic light scattering screen for a number of different formulation conditions, each having from 2 to 10 mg/ml protein. The diffusion interaction parameter indicated that taurine and PSA (propane sulfonic acid) improved Kd.

Example 6: Taurine and Propane Sulfonic Acid Provide Improved Stability to High Concentration VEGF Trap (Aflibercept) Formulations An experiment was conducted to determine the effect on protein stability with a number of formulation combinations. FIG. 6 shows a dynamic light scattering plot for formulations having anywhere from 2 mg/ml protein to 10 mg/ml protein (aflibercept). Formulations that included 70 mM taurine or 70 mM PSA showed reduced self-interaction at higher concentrations. These data indicate that taurine and PSA can be useful inclusions in high concentration protein formulations, like the ones at issue in this case.

Example 7: Long Term Study of Stability of Various Histidine Containing Formulations A total of 9 different aflibercept formulations were tested with varying buffer concentration, thermal stabilizers and hydrophobic salts. The 9 formulations, F1-F9, are summarized below in Table 7-1.

TABLE 7-1

Formulations F1-F9.

| Formulation | VEGFT (mg/mL) | Buffer Type | Buffer Concentration (mM) | Sucrose (% w/v) | Proline (% w/v) | Polysorbate 20 (w/v) | Stabilizer (mM) | Stabilizer Concentration (mM) | pH |
|---|---|---|---|---|---|---|---|---|---|
| F1 (WW) | 140 | His | 10 | 5 | 0 | 0.03 | Taurine | 50 | 5.8 |
| F2 (XX) | 140 | His | 20 | 0 | 4 | 0.03 | Arginine HCl | 50 | 5.8 |
| F3 (YY) | 140 | His | 20 | 2.5 | 2 | 0.03 | Taurine | 50 | 5.8 |
| F4 (ZZ) | 140 | His | 10 | 2.5 | 2 | 0.03 | Arginine HCl | 50 | 5.8 |
| F5 (AAA) | 140 | His | 20 | 5 | 0 | 0.03 | PSA | 50 | 5.8 |
| F6 (BBB) | 140 | His | 20 | 2.5 | 2 | 0.03 | PSA | 50 | 5.8 |

TABLE 7-1-continued

Formulations F1-F9.

| Formulation | VEGFT (mg/mL) | Buffer Type | Buffer Concentration (mM) | Sucrose (% w/v) | Proline (% w/v) | Polysorbate 20 (w/v) | Stabilizer (mM) | Stabilizer Concentration (mM) | pH |
|---|---|---|---|---|---|---|---|---|---|
| F7 (CCC) | 140 | His | 20 | 5 | 0 | 0.03 | Arginine HCl | 50 | 5.8 |
| F8 (DDD) | 140 | His | 10 | 0 | 4 | 0.03 | PSA | 50 | 5.8 |
| F9 (EEE) | 140 | His | 20 | 5 | 0 | 0.03 | NA | NA | 5.8 |

VEGFT = VEGF Trap (aflibercept)

Fourteen (14) mL of each formulation was compounded in 15 mL Falcon tubes. The formulation was then sterile filtered using a 0.22 μM syringe filter and filled in sterile 2 mL Type 1 glass vials. Eight (8) vials were filled for each formulation with 0.4 mL volume in a laminar flow hood.

SE-UPLC (molecular weight species) was performed on all samples to determine the chemical stability of each formulation.

Figure 7:
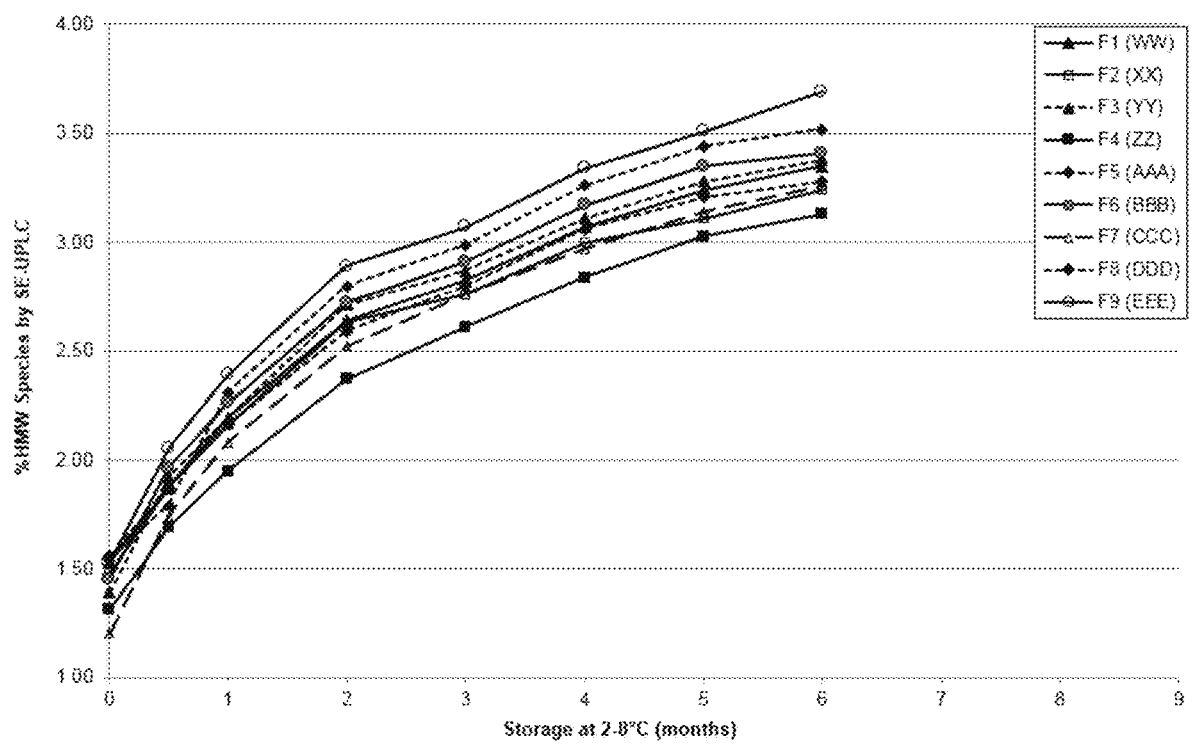
FIG. 7 is a graph monitoring the percentage of high molecular weight (HMW) species in formulations F1-F9 (formulations WW-EEE) over time as measured by size-exclusion ultra-performance liquid chromatography (SE-UPLC) after storage at 5° C. for 6 months. Formulations F1-F9 are set forth in Table 7-1 herein.

The percentage of HMW species over time for each of formulations F1-F9 are shown in FIG. 7 (see also Table 7-2). Formulations F4 and F7 exhibited the lowest percentage of HMW species after 4 months at 5° C. The results showed that addition of excipients like arginine and proline significantly reduced the rate of % HMW species formation in VEGF Trap formulations.

TABLE 7-2

SE-UPLC Analysis (2-8° C.)

|  | F1 (WW) | | F2 (XX) | | F3 (YY) | |
|---|---|---|---|---|---|---|
| Months at 2-8 C. | % HMW | % Main Peak | % HMW | % Main Peak | % HMW | % Main Peak |
| 0.0 | 1.53 | 98.46 | 1.48 | 98.52 | 1.39 | 98.61 |
| 0.5 | 1.87 | 98.13 | 1.87 | 98.13 | 1.92 | 98.08 |
| 1.0 | 2.19 | 97.81 | 2.16 | 97.84 | 2.19 | 96.15 |
| 2.0 | 2.64 | 97.36 | 2.63 | 97.37 | 2.71 | 97.29 |
| 3.0 | 2.83 | 97.17 | 2.76 | 97.24 | 2.87 | 97.13 |
| 4.0 | 3.07 | 96.93 | 3.00 | 97.00 | 3.11 | 96.89 |
| 5.0 | 3.24 | 96.76 | 3.11 | 96.89 | 3.28 | 96.72 |
| 6.0 | 3.35 | 96.65 | 3.24 | 96.76 | 3.38 | 96.62 |

|  | F4 (ZZ) | | F5 (AAA) | | F6 (BBB) | |
|---|---|---|---|---|---|---|
| Months at 2-8 C. | % HMW | % Main Peak | % HMW | % Main Peak | % HMW | % Main Peak |
| 0.0 | 1.31 | 98.69 | 1.55 | 98.45 | 1.45 | 98.55 |
| 0.5 | 1.69 | 98.31 | 1.79 | 98.21 | 1.96 | 98.04 |
| 1.0 | 1.95 | 98.05 | 2.31 | 97.69 | 2.26 | 97.74 |
| 2.0 | 2.37 | 97.63 | 2.80 | 97.20 | 2.72 | 97.28 |
| 3.0 | 2.61 | 97.39 | 2.99 | 97.01 | 2.91 | 97.09 |
| 4.0 | 2.84 | 97.16 | 3.26 | 96.74 | 3.17 | 96.83 |
| 5.0 | 3.03 | 96.97 | 3.44 | 96.56 | 3.35 | 96.65 |
| 6.0 | 3.13 | 96.87 | 3.52 | 96.48 | 3.41 | 96.59 |

|  | F7 (CCC) | | F8 (DDD) | | F9 (EEE) | |
|---|---|---|---|---|---|---|
| Months at 2-8 C. | % HMW | % Main Peak | % HMW | % Main Peak | % HMW | % Main Peak |
| 0.0 | 1.20 | 98.80 | 1.56 | 98.44 | 1.53 | 98.47 |
| 0.5 | 1.74 | 98.26 | 1.87 | 98.13 | 2.05 | 97.95 |
| 1.0 | 2.08 | 97.92 | 2.16 | 97.84 | 2.39 | 97.61 |
| 2.0 | 2.52 | 97.48 | 2.59 | 97.41 | 2.89 | 97.11 |
| 3.0 | 2.76 | 97.24 | 2.80 | 97.20 | 3.07 | 96.93 |
| 4.0 | 2.97 | 97.03 | 3.06 | 96.94 | 3.34 | 96.66 |
| 5.0 | 3.14 | 96.86 | 3.21 | 96.79 | 3.51 | 96.49 |
| 6.0 | 3.26 | 96.74 | 3.28 | 96.72 | 3.69 | 96.31 |

Example 8: Stability Study of 140 mg/mL VEGF Trap with Varying Arginine Concentrations The impact of varying the concentration of arginine-HCl on the stability of four 140 mg/mL VEGF Trap (aflibercept) eye drug product formulations was studied. The evaluation of stability was performed at the storage condition of 2-8° C. The drug product (DP) was also incubated under stress (37° C.) conditions. The four formulations being evaluated in this stability study (F1-F4) are described in Table 8-1 set forth below.

TABLE 8-1

Formulations F1-F4

| | Composition | | | | | |
|---|---|---|---|---|---|---|
| Formulation Number | VEGFT (mg/mL) | Histidine (mM) | Sucrose (w/v) | Polysorbate 20 | L-Arginine- | pH |
| F1 | 140 | 20 | 5 | 0.03 | 0 | 5.8 |
| F2 | | | | | 10 | |
| F3 | | | | | 50 | |
| F4 | | | | | 100 | |

Approximately 145 mL of 187 mg/mL VEGF Trap histidine formulations were thawed. Thirty six (36) mL of each formulation, with the exception of F3, was compounded; 39 mL of bulk F3 was compounded. Each formulation was filter sterilized within a LFH (laminar flow hood) using a 0.22 µm Durapore PVDF sterilizing filter prior to filling. Clean depyrogenated 2 mL type I Schott glass vials stoppered with 13 mm serum stoppers (S2-F451 4432/50B2-40) were used to perform stability studies.

SE-UPLC analysis of the formulations was performed as set forth above. The % HMW measurements, using SE-UPLC, in each formulation over time are set forth in FIG. 8 (A-B). See also Tables 8-2 and 8-3.

When stored at 5° C., these formulations exhibited a reduction in the rate of formation of % HMW species that was proportional to the concentration of arginine-HCl. Under stress, however, this effect was reversed. The formulations, at 37° C., exhibited an apparent increase in % HMW species proportional to the concentration of arginine-HCl. This property made the discovery of arginine's beneficial effects on aflibercept in the presence of histidine buffer highly unlikely. Typically, for formulation development in the biotechnology industry, the effect of various excipients on a drug is initially screened under stress (e.g., at elevated temperature such as 37° C.) for a short period of time. The purpose of this approach it to rapidly eliminate excipients which will not likely perform well in the absence of stress (e.g., at lower temperature such as 5° C.) over a longer period of time. Here, arginine was identified as a helpful excipient in spite of its effect on stability at 37° C. Since formulated drug product is typically stored for months at 4-5° C. after manufacture, aflibercept in arginine and histidine buffer would be a highly valuable formulation for long term, stable drug product storage.

TABLE 8-2

SE-UPLC Analysis (2-8° C.)

| Months at 2-8 C. | F1 (EEE) | | F2 (SSS) | |
|---|---|---|---|---|
| | % Main Peak | % HMW | % Main Peak | % HMW |
| 0.0 | 97.79 | 2.21 | 97.78 | 2.22 |
| 0.5 | 97.56 | 2.43 | 97.59 | 2.41 |
| 1.0 | 97.30 | 2.70 | 97.34 | 2.66 |
| 1.5 | 97.21 | 2.79 | 97.26 | 2.74 |
| 2.0 | 97.05 | 2.95 | 97.08 | 2.92 |
| 2.5 | 96.96 | 3.04 | 97.02 | 2.98 |
| 3.0 | 96.82 | 3.18 | 96.88 | 3.12 |
| 6.0 | 96.35 | 3.65 | 96.40 | 3.60 |

| Months at 2-8 C. | F3 (CCC) | | F4 (TTT) | |
|---|---|---|---|---|
| | % Main Peak | % HMW | % Main Peak | % HMW |
| 0.0 | 97.85 | 2.15 | 97.81 | 2.19 |
| 0.5 | 97.67 | 2.33 | 97.73 | 2.27 |
| 1.0 | 97.47 | 2.53 | 97.59 | 2.41 |
| 1.5 | 97.37 | 2.63 | 97.50 | 2.50 |
| 2.0 | 97.22 | 2.78 | 97.36 | 2.64 |
| 2.5 | 97.14 | 2.86 | 97.31 | 2.69 |
| 3.0 | 97.04 | 2.96 | 97.16 | 2.84 |
| 6.0 | 96.60 | 3.40 | 96.77 | 3.23 |

TABLE 8-3

SE-UPLC Analysis (37° C.)

| Days at 37 C. | F1 (EEE) | | F2 (SSS) | |
|---|---|---|---|---|
| | % Main Peak | % HMW | % Main Peak | % HMW |
| 0.0 | 97.79 | 2.21 | 97.78 | 2.22 |
| 7 | 93.66 | 6.34 | 93.32 | 6.68 |
| 14.0 | 89.48 | 10.35 | 88.79 | 10.98 |
| 21.0 | 86.64 | 13.08 | 85.69 | 13.82 |
| 28.0 | 83.90 | 15.85 | 82.66 | 16.90 |

| Days at 37 C. | F3 (CCC) | | F4 (TTT) | |
|---|---|---|---|---|
| | % Main Peak | % HMW | % Main Peak | % HMW |
| 0.0 | 97.85 | 2.15 | 97.81 | 2.19 |
| 7 | 92.38 | 7.61 | 91.32 | 8.68 |
| 14.0 | 86.90 | 12.91 | 84.61 | 15.21 |
| 21.0 | 83.11 | 16.65 | 80.11 | 19.47 |
| 28.0 | 79.44 | 20.29 | 75.80 | 23.91 |

Example 9: VEGF Trap Stability in the Presence of Counterions from the Hofmeister Series and Other Excipients The effect of various counterions and other excipients on stability of several formulations was determined.

A. Counterion Screening

Counter ions (e.g., sulfate, thiocyanate and citrate) were tested in the form of sodium salts with high concentration VEGF Trap (aflibercept) formulations (140 mg/ml). Additionally, other amino add excipients (e.g., glycine and lysine) were also tested.

Approximately 42 ml of 187 mg/ml VEGF Trap eye drug substance were thawed. 50 ml of intermediate formulated drug substance (155.56 mg/ml), having a 110% concentration of the 140 mg/ml formulated drug substance and target excipient concentration (excluding the counterions, glycine and lysine), were prepared.

The intermediate formulated drug substance was further diluted with the 0.5 M stock excipient solutions (counterions, glycine or lysine) to produce the 140 mg/ml formulated drug substance formulations listed in Table 9-1 below. Each final formulation was filter sterilized with a 0.22 µm PVDF syringe filter within a laminar flow hood prior to filling into clean depyrogenated 2 mL type I Schott glass vials stoppered with 13 mm serum stoppers S2-F451 4432/50 82-40 (ELN item #19700004 Wash #0 000078949). Sixty (60) vials were filled with 0.5 ml of each formulation. Six (6) vials were filled with 1.5 ml.

TABLE 9-1

Formulations for Counterion Screening

| Excipient (mM) | Formulation | VEGF Trap conc. |
|---|---|---|
| Sodium sulfate 50 mM | 20 mM Histidine/0.03% PS20/5% Sucrose/50 mM Sodium Sulfate | 140 |
| Sodium thiocyanate 50 mM | 20 mM Histidine/0.03% PS20/5% Sucrose/50 mM Sodium thiocyanate | 140 |
| Sodium Citrate 50 mM | 20 mM Histidine/0.03% PS20/5% Sucrose/50 mM Sodium Citrate | 140 |

TABLE 9-1-continued

Formulations for Counterion Screening

| Excipient (mM) | Formulation | VEGF Trap conc. |
|---|---|---|
| Glycine 50 mM | 20 mM Histidine/0.03% PS20/5% Sucrose/50 mM Glycine | 140 |
| Sodium chloride 50 mM | 20 mM Histidine/0.03% PS20/5% Sucrose/50 mM sodium chloride | 140 |
| Lysine 50 mM | 20 mM Histidine/0.03% PS20/5% Sucrose/50 mM Lysine | 140 |

B. Glutamate and Aspartate Screening

The stability of VEGF Trap (aflibercept) high concentration formulations (140 mg/ml) in the presence of organic counter ions in combination with arginine hydrochloride was tested. In addition, two new counter ions (glutamate and asparate) were tested for compatibility with high concentration VEGF Trap (in combination and without arginine hydrochloride). The formulations tested are summarized below in Table 9-2.

Approximately 50 ml of 187 mg/ml VEGF Trap drug substance were thawed. 60 ml of intermediate formulated drug substance (155.56 mg/ml) with a 110% of the 140 mg/ml formulated drug substance and target excipient concentration (excluding the counterions, citrate, glycine, glutamate and aspartate) was prepared. The intermediate formulated drug substance was further diluted with the 1M stock excipient solutions (arginine hydrochloride, sodium citrate, glycine, sodium glutamate and sodium aspartate) to produce the 140 mg/ml formulated drug substance formulations listed in the table below. Each final formulation was filter sterilized with a 0.22 μm PVDF syringe filter within a laminar flow hood prior to filling into clean depyrogenated 2 ml type I Schott glass vials stoppered with 13 mm serum stoppers S2-F451 4432/50 B2-40 (ELN item #19700004 Wash #0000078949). Sixty (60) vials were filled with 0.5 ml of each formulation. Six (6) vials were filled with 1.5 ml.

TABLE 9-2

Formulations for Glutamate And Aspartate Screening

| Excipient (mM) | Formulation | VEGF Trap conc. |
|---|---|---|
| Sodium Citrate 50 mM + Arginine Hydrochloride 50 mM | 20 mM Histidine/0.03% PS20/5% Sucrose/50 mM Sodium Citrate/50 mM Arginine hydrochloride | 140 |
| Glycine 50 mM + Arginine hydrochloride 50 mM | 20 mM Histidine/0.03% PS20/5% Sucrose/50 mM Glycine/50 mM Arginine hydrochloride | 140 |
| Sodium aspartate 50 mM + Arginine hydrochloride 50 mM | 20 mM Histidine/0.03% PS20/5% Sucrose/50 mM Sodium Aspartate/50 mM Arginine hydrochloride | 140 |
| Sodium glutamate 50 mM + Arginine hydrochloride 50 mM | 20 mM Histidine/0.03% PS20/5% Sucrose/50 mM Sodium Glutamate/50 mM Arginine hydrochloride | 140 |
| Sodium aspartate 50 mM | 20 mM Histidine/0.03% PS20/5% Sucrose/50 mM sodium aspartate | 140 |
| Sodium glutamate 50 mM | 20 mM Histidine/0.03% PS20/5% Sucrose/50 mM Sodium glutamate | 140 |

Figure 9:
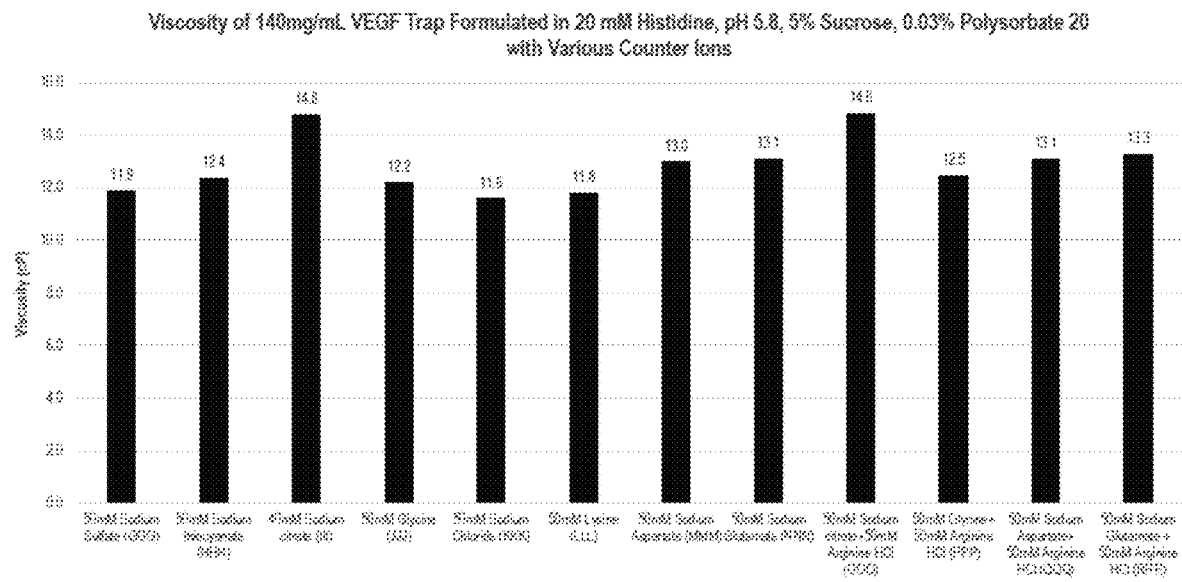
FIG. 9 shows the viscosity (cp) for Formulations F1-F12, at 20° C., at the initial time point. Formulations F1-F12 are set forth in Table A below.

Viscosity testing was performed using a RHEOSENSE m-VROC® viscometer. Approximately, 0.5 mL of undiluted sample was loaded onto a glass syringe. The sample was equilibrated to the desired temperature and injected into a chip or measuring cell. Viscosity was calculated by measuring the pressure drop from inlet to the outlet which is correlated to the shear-stress at the wall of the chip. Results are expressed as mPas-1 or cp. See FIG. 9 and Table 9-3.

Osmolality testing was performed using a VAPRO vapor pressure osmometer. Approximately, 10 μL of undiluted sample was inoculated into a paper disc. The dew point temperature depression, a function of the solution vapor pressure, was measured through a sensitive thermocouple and reported as osmolality of the solution. Results are expressed as mmol/kg or mOsm. See FIG. 10 and Table 9-3.

High molecular weight species in certain formulations over time, after storage at 37° C. or 5° C., was also evaluated by SE-UPLC. See FIGS. 11 (A-B) and Tables 9-4 and 9-5.

Dynamic light scattering experiments were performed using a DynaPro® Plate Reader II. Approximately, 100 μL of undiluted sample was loaded onto a 96-well plate. Thirty five acquisitions were obtained for each well at 25° C. Analysis of autocorrelation function using regularization was performed on the DYNAMICS v7.1 software. Radius (nm) vs % intensity plots and % mass vs radius (nm) plots were generated to derive the average molecular radius and % polydispersity values (% Pd) for each sample. See FIG. 12.

TABLE 9-3

Viscosity and Osmolality of Various Formulations

| Parameter tested | 50 mM Sodium Sulfate (GGG) | 50 mM Sodium thiocyanate (HHH) | 40 mM Sodium citrate (III) | 50 mM Glycine (JJJ) | 50 mM Sodium Chloride (KKK) | 50 mM Lysine (LLL) |
|---|---|---|---|---|---|---|
| viscosity (cp) | 11.9 | 12.4 | 14.8 | 12.2 | 11.6 | 11.8 |
| Osmolality (mOsmol/Kg) | 384 | 324 | 403 | 299 | 349 | 349 |

| | 50 mM Sodium Aspartate | 50 mM Sodium Glutamate | 50 mM Sodium citrate + 50 mM Arginine HCl | 50 mM Glycine + 50 mM Arginine HCl | 50 mM Sodium Aspartate + 50 mM Arginine HCl | 50 mM Sodium Glutamate + 50 mM Arginine HCl |
|---|---|---|---|---|---|---|

TABLE 9-3-continued

Viscosity and Osmolality of Various Formulations

| Parameter tested | (MMM) | (NNN) | (OOO) | (PPP) | (QQQ) | (RRR) |
|---|---|---|---|---|---|---|
| viscosity (cp) | 13.0 | 13.1 | 14.8 | 12.5 | 13.1 | 13.3 |
| Osmolality (mOsmol/Kg) | 343 | 346 | 506 | 369 | 426 | 430 |

TABLE 9-4

SE-UPLC Analysis; % HMW (37° C.)

| % HMW (Days at 37 C.) | 50 mM Sodium Sulfate (GGG) | 50 mM Sodium thiocyanate (HHH) | 40 mM Sodium citrate (III) | 50 mM Glycine (JJJ) | 50 mM Sodium Chloride (KKK) | 50 mM Lysine (LLL) |
|---|---|---|---|---|---|---|
| 0 | 2.3 | 2.3 | 2.3 | 2.3 | 2.3 | 2.2 |
| 7 | 8.6 | 15.5 | 8.2 | 6.3 | 8.1 | 7.7 |
| 14 | 13.5 | 24.8 | 12.1 | 9.5 | 12.4 | 11.7 |
| 28 | 22.0 | 39.2 | 19.1 | 15.3 | 20.4 | 19.3 |

TABLE 9-5

SE-UPLC Analysis; % HMW (5° C.)

| % HMW (Months at 5 C.) | 50 mM Sodium Sulfate (GGG) | 50 mM Sodium thiocyanate (HHH) | 40 mM Sodium citrate (III) | 50 mM Glycine (JJJ) | 50 mM Sodium Chloride (KKK) | 50 mM Lysine (LLL) |
|---|---|---|---|---|---|---|
| 0 | 2.3 | 2.3 | 2.3 | 2.3 | 2.3 | 2.2 |
| 0.25 | 2.3 | 2.4 | 2.4 | 2.3 | 2.3 | 2.3 |
| 0.5 | 2.4 | 2.5 | 2.5 | 2.4 | 2.4 | 2.3 |
| 1 | 2.5 | 2.8 | 2.7 | 2.6 | 2.6 | 2.5 |
| 2 | 2.8 | 2.9 | 2.9 | 2.8 | 2.8 | 2.8 |
| 3 | 3.1 | 3.3 | 3.2 | 3.1 | 3.2 | 3.0 |

Example 10: Tolerability of IVT Delivery of High Dose VEGF Trap (140 mg/ml) in Normal Rabbits Anti-VEGF therapeutics, administered via intravitreal injection, are currently the standard of care for treatment of neovascular age-related macular degeneration, diabetic macular edema, and retinal vascular occlusive disease. However, the monthly or bi-monthly intravitreal injections represent a significant treatment burden on patients, caregivers, and physicians. There is a pressing need for more effective and durable therapies in clinical practice. This study is to investigate the tolerability of stably formulated high dose VEGF Trap (140 mg/ml, equivalently 14 folds of the clinical dose) in normal New Zealand white rabbit eyes.

Two formulations of high dose VEGF-Trap (aflibercept) in histidine buffer or in phosphate buffer were tested. Three rabbits per cohort received 7 mg of VEGF Trap in 50 uL by single bilateral intravitreal injection of each formulation. Ocular inflammation signs were monitored by slit lamp, optical coherence tomography (OCT) and fundus angiograph at day 1, day 4, week 1 then weekly until 12 weeks post-intravitreal administration. Intraocular pressure was measured with Tonopen before and 10 minutes and 30 minutes post intravitreal injection, then at every follow up time point. Animals were euthanized at week 12.

The rabbit eyes were dosed with either:
(1) 140 mg/ml aflibercept, 20 mM Histidine, 5% Sucrose, 50 mM Arginine HCl, 0.03% PS20, pH 5.8; or
(2) 140 mg/ml aflibercept, 10 mM Sodium phosphate, 5% Sucrose, 40 mM Sodium Chloride, 0.03% PS20, pH 6.2.

Two of six eyes from the histidine buffer group showed dark shadows in the vitreous until 8 weeks post IVT, which were confirmed by slit-lamp examination as local cataract due to posterior lens injury, procedure related. One of 6 eyes the from phosphate buffer group showed dark shadows in the vitreous until 8 weeks post IVT, which were confirmed by slit-lamp examination as local cataract due to posterior lens injury (procedure related).

The high dose VEGF Trap (140 mg/ml) formulations tested were well tolerated in normal New Zealand White rabbit eyes within 12 weeks post-single intravitreal administration. After a single intravitreal injection of 7 mg of VEGF Trap, no signs of abnormalities or inflammation were seen in the fundus. The vitreous was clear and the retinal vascular pattern appeared normal. No retinal detachment, hemorrhage or optic nerve head changes were seen. There was no intraocular pressure change compared to baseline. The baseline fluorescein angiography (FA) and OCT images of rabbit eyes are represented in FIG. 13(A-D). The time course FA and OCT images of rabbit eyes in each treatment group over 8 weeks is represented in FIGS. 14, 15, 16 and 17. Data from the left eye (OS) or right eye (OD) of rabbits 326 and 329 are shown.

Example 11: Evaluation of Stability of Formulations UUU-BBBB

This study examined the stability of 60 mg/ml and 120 mg/ml VEGF Trap (aflibercept) in 10 mM phosphate, 10% or 20% sucrose (Suc.), 0 or 50 mM NaCl, 0.03% polysorbate 20, pH 6.2 when incubated at 37° C. for up to 6 months. The formulations for this stability study are set forth below in Table 11-1.

TABLE 11-1

Formulations UUU-BBBB

| Formulation Designation | [VEGF Trap] mg/mL | % Sucrose | mM NaCl |
|---|---|---|---|
| F1 (UUU) | 30 | 10 | — |
| F2 (VVV) | 30 | 20 | — |
| F3 (WWW) | 60 | 10 | — |
| F4 (XXX) | 60 | 20 | — |
| F5 (YYY) | 120 | 10 | — |
| F6 (ZZZ) | 120 | 20 | — |
| F7 (AAAA) | 120 | 10 | 50 |
| F8 (BBBB) | 120 | 20 | 50 |

Base formulation: 10 mM phosphate, 0.03% polysorbate 20, pH 6.2
VEGF Trap = aflibercept The formulation was filter sterilized with a PVDF 0.2 µm filter in a laminar flow hood prior to dispensing.

Vials containing each formulation were stored at 37° C. for 1 month.

TABLE 11-2

Reverse-phase High Performance Liquid Chromatography (RP-HPLC) Results

| Formulation | Storage Condition | Actual Incubation (months) | % VEGFT Recovered | [VGFT] mg/ml |
|---|---|---|---|---|
| 30 mg/mL 10% sucrose (UUU) | 37° C. | 0.0 | 100.0 | 29.99 |
|  |  | 1.0 | 97.9 | 29.37 |
| 30 mg/mL 20% sucrose (VVV) | 37° C. | 0.0 | 100.0 | 29.97 |
|  |  | 1.0 | 98.2 | 29.44 |
| 60 mg/mL 10% sucrose (WWW) | 37° C. | 0.0 | 100.0 | 58.90 |
|  |  | 1.0 | 98.3 | 57.89 |
| 60 mg/mL 20% sucrose (XXX) | 37° C. | 0.0 | 100.0 | 58.80 |
|  |  | 1.0 | 98.9 | 58.18 |
| 120 mg/mL 10% sucrose (YYY) | 37° C. | 0.0 | 100.0 | 120.80 |
|  |  | 1.0 | 97.4 | 117.63 |
| 120 mg/mL 20% sucrose (ZZZ) | 37° C. | 0.0 | 100.0 | 117.85 |
|  |  | 1.0 | 98.9 | 116.51 |
| 120 mg/mL 10% sucrose 50 mM NaCl (AAAA) | 37° C. | 0.0 | 100.0 | 120.14 |
|  |  | 1.0 | 97.9 | 117.64 |
| 120 mg/mL 20% sucrose 50 mM NaCl (BBBB) | 37° C. | 0.0 | 100.0 | 120.55 |
|  |  | 1.0 | 97.0 | 116.94 |

VGFT = VEGF Trap, aflibercept

TABLE 11-3

Size-exclusion Ultra Performance Liquid Chromatography (SE-UPLC) Results

| Formulation | Storage Condition | Actual Incubation (months) | Total % HMW | % Native | Total % LMW |
|---|---|---|---|---|---|
| 30 mg/mL VGFT 10% sucrose (UUU) | 37° C. | 0 | 0.8 | 99.0 | 0.1 |
|  |  | 1.0 | 4.1 | 94.0 | 1.9 |
| 30 mg/mL VGFT 20% sucrose (VVV) | 37° C. | 0 | 0.8 | 99.0 | 0.2 |
|  |  | 1.0 | 2.4 | 95.6 | 2.0 |
| 60 mg/mL VGFT 10% sucrose (WWW) | 37° C. | 0 | 1.0 | 98.8 | 0.2 |
|  |  | 1.0 | 7.8 | 89.5 | 2.7 |
| 60 mg/mL VGFT 20% sucrose (XXX) | 37° C. | 0 | 1.0 | 98.8 | 0.2 |
|  |  | 1.0 | 4.4 | 92.8 | 2.7 |
| 120 mg/mL VGFT 10% sucrose (YYY) | 37° C. | 0 | 1.3 | 98.5 | 0.2 |
|  |  | 1.0 | 18.3 | 79.5 | 2.2 |
| 120 mg/mL VGFT 20% sucrose (ZZZ) | 37° C. | 0 | 1.2 | 98.5 | 0.2 |
|  |  | 1.0 | 10.7 | 87.1 | 2.2 |
| 120 mg/mL VGFT 10% sucrose 50 mM NaCl (AAAA) | 37° C. | 0 | 1.3 | 98.5 | 0.2 |
|  |  | 1.0 | 20.8 | 77.1 | 2.2 |
| 120 mg/mL VGFT 20% sucrose 50 mM NaCl (BBBB) | 37° C. | 0 | 1.2 | 98.5 | 0.3 |
|  |  | 1.0 | 13.0 | 84.8 | 2.2 |

VGFT = VEGF Trap, aflibercept

All of the formulations were essentially particle-free by visual inspection and optical density measurement. There was no significant protein loss in recovery by RP-HPLC after 1 month at 37° C. (Table 11-2) and this trend continued out to 6 months.

The main degradation pathway for VEGF Trap was aggregation under these conditions (FIGS. 18 (A-B); Table 11-3). The stability of VEGF Trap was dependent on the protein and sucrose concentrations. Formulations with lower VEGF Trap concentrations and higher sucrose were more stable. Maintaining the same protein:sucrose ratio did not result in the same degradation rate. For example, F1 and F4 have the same protein:sucrose ratio of 3:1 but F4 was less stable than F1 due to its higher protein concentration. Similar trends were observed out to 6 months.

Example 12: Repeat-Dose Intravitreal Toxicology Study in Monkeys with Different Aflibercept Formulations The safety of various formulations in cynomolgus monkeys is assessed in this example. A total of 7 intravitreal doses are administered to both eyes approximately Q4W to Groups 1-3; a total of 3 intravitreal doses are administered to both eyes approximately Q4W to groups 4-9. A terminal necropsy is performed approximately one week after last dose (N=3/sex/group) with recovery necropsy (2/sex/group) approximately 12-week after last dose The following assessments are performed:
Safety assessment based on clinical signs, body weights, vital signs, electrocardiographic data (pre-dose end of treatment and end of recovery), blood pressure measurements (via tail cuff), clinical and anatomic pathology
Comprehensive ocular exams at regular intervals during the dosing and recovery intervals including slit lamp microscopy, indirect ophthalmoscopy and intraocular pressure measurements
Fundus photography, fluorescein angiography and electroretinography at pre-treatment, during study week 9 (all groups), week 26 (Groups 1-3 only) and end of recovery period
Blood and vitreous samples (at termination) for bioanalytical, ADA analysis and toxicokinetic evaluation Stability and purity data after storage at 37° C., 25° C. and 2-8° C. are shown in FIGS. 19 (A-E). See also Tables 13-1-13-4.

TABLE 13-1

Size-Exclusion Chromatography (SEC) Purity Analysis

| Months | % Main | % HMW | % LMW |
|---|---|---|---|
| 37° C. | | | |
| 0 | 98.23 | 1.77 | 0 |
| 0.229 | 92.88 | 7.07 | 0.05 |
| 0.459 | 88.59 | 11.18 | 0.23 |
| 0.688 | 84.67 | 15.03 | 0.3 |
| 0.918 | 81.84 | 17.59 | 0.57 |

TABLE 13

Study group summary*

| Group | Test Material | IVT Dose Volume (μL/dose/eye) | mg aflibercept/eye | N/sex | N/sex for terminal necropsy | N/sex for Recovery |
|---|---|---|---|---|---|---|
| 1 | 20 mM Histidine, 50 mM Arginine, 5% Sucrose, 0.03% PS20 | 50 | 0 (control) | 5 | 3 | 2 |
| 2 | 80 mg/mL Aflibercept in 20 mM Histidine, 50 mM Arginine, 5% Sucrose, 0.03% PS20 | 50 | 4 | 5 | 3 | 2 |
| 3 | ~140 mg/mL Aflibercept in 20 mM Histidine, 50 mM Arginine, 5% Sucrose, 0.03% PS20 | 50 | ~7 | 5 | 3 | 2 |
| 4 | 20 mM Histidine, 5% Sucrose, 0.03% PS20 | 50 | 0 (control) | 5 | 3 | 2 |
| 5 | 80 mg/mL Aflibercept in 20 mM Histidine, 5% Sucrose, 0.03% PS20 | 50 | 4 | 5 | 3 | 2 |
| 6 | ~140 mg/mL Aflibercept in 20 mM Histidine, 5% Sucrose, 0.03% PS20 | 50 | ~7 | 5 | 3 | 2 |
| 7 | 20 mM Histidine, 50 mM Glycine, 5% Sucrose, 0.03% PS20 | 50 | 0 (control) | 5 | 3 | 2 |
| 8 | 80 mg/mL Aflibercept in 20 mM Histidine, 50 mM Glycine, 5% Sucrose, 0.03% PS20 | 50 | 4 | 5 | 3 | 2 |
| 9 | ~140 mg/mL Aflibercept in 20 mM Histidine, 50 mM Glycine, 5% Sucrose, 0.03% PS20 | 50 | ~7 | 5 | 3 | 2 |

*each of said formulations are part of the present invention

It is expected that the formulations tested in any one or more of Groups 1, 2, 3, 4, 5, 6, 7, 8 and/or 9 will be determined to have a safety profile comparable to EYLEA in cynomolgus monkeys as measured in the assessments discussed above.

Example 13: Stability Study with VEGF Trap Product

A formulation including 114.3 mg/mL VEGF Trap (aflibercept) and 10 mM Histidine, pH 5.8, 5% Sucrose, 0.03% Polysorbate 20, 50 mM Arginine Monohydrochloride was prepared within a LFH (laminar flow hood) using a 0.22 μm Durapore PVDF sterilizing filter prior to filling. Clean depyrogenated 3 mL type I Schott glass vials were filled with 0.3 mL of Drug Product and stoppered with 13 mm serum stoppers (S2-F451 4432/50B2-40). Samples were analyzed at various timepoints after storage at 37° C. or 5° C. for purity by size-exclusion chromatography (SEC) to determine the presence (%) of high molecular weight species (HMW), low molecular weight species (LMW) and the main peak (main); as well as microflow imaging, HIAC liquid particle counting (by light obscuration) and microscopically to determine the presence of particles of various sizes.

TABLE 13-1-continued

Size-Exclusion Chromatography (SEC) Purity Analysis

| Months | % Main | % HMW | % LMW |
|---|---|---|---|
| 5° C. | | | |
| 0 | 98.23 | 1.77 | 0 |
| 1 | 97.73 | 2.27 | 0 |
| 2 | 97.4 | 2.59 | 0 |

TABLE 13-2

Microflow Imaging/Subvisible Particles
37° C.

| Months | ≥1 μm | ≥2 μm | ≥5 μm | ≥10 μm | ≥25 μm |
|---|---|---|---|---|---|
| T = 0 | 1125 | 234 | 42 | 9 | 0 |
| 28 days | 1128 | 184 | 17 | 0 | 0 |

TABLE 13-3

Subvisible Particulate Matter as Measured by Light Obscuration (HIAC)/Subvisible Particles 37° C.

| Months | ≥10 μm | ≥25 μm | ≥50 μm |
|---|---|---|---|
| T = 0 | 15 | 0 | 0 |
| 28 days | 23 | 1 | 1 |

TABLE 13-4

Microscopic Analysis of Subvisible Particles 37° C.

| Months | ≥10 μm | ≥25 μm | ≥50 μm |
|---|---|---|---|
| T = 0 | 8 | 1 | 1 |
| 28 days | 6 | 2 | 1 |

Example 14: Stability Study with Varying VEGF Trap Concentrations

The impact of varying the concentration of VEGF Trap on the stability of four VEGF Trap (aflibercept) eye drug product formulations was studied. The concentrations ranged between 80 and 140 mg/mL. The evaluation of stability was performed at the storage condition of 2-8° C. The drug product (DP) was also incubated under stress (37° C.) conditions. The four formulations (each of which is named "CCC" herein) being evaluated in this stability study are described in Table 14-1 set forth below.

Approximately 27 mL of each formulation was prepared within a LFH (laminar flow hood) using a 0.22 μm Durapore PVDF sterilizing filter prior to filling. Clean depyrogenated 2 mL type I Schott glass vials were filled and stoppered with 13 mm serum stoppers (S2-F451 4432/50B2-40). Samples were analyzed at various timepoints after storage at 37° C. or 2-8° C. for purity by size-exclusion-ultraperformance liquid chromatography (SE-UPLC) to determine the presence (%) of high molecular weight species (HMW) and the main peak (main).

Data showing the percentage HMW after incubation at 2-8° C. or 37° C. for up to 6 months are set forth in FIGS. 20 (A-B). See also Tables 14-2 and 14-3. When stored at 37° C. and 5° C., these formulations exhibited a positive correlation of the rate of HMW formation to the concentration of VEGF Trap. The 140 mg/mL formulation exhibited highest rate of % HMW species formation.

TABLE 14-1

Formulations tested.

| Formulation Number | L-Arginine mM | Histidine (mM) | Sucrose (w/v) | Polysorbate 20 (w/v) | VEGFT (mg/mL) | pH |
|---|---|---|---|---|---|---|
| F1 (CCC) | 50 | 20 | 5 | 0.03 | 80 | 5.8 |
| F2 (CCC) | | | | | 100 | |
| F3 (CCC) | | | | | 120 | |
| F4 (CCC) | | | | | 140 | |

TABLE 14-2

SE-UPLC Analysis (2-8° C.)

| Months at 2-8 C. | F1 (CCC): 80 mg/mL | | F2 (CCC): 100 mg/mL | | F4 (CCC): 120 mg/mL | | F3 (CCC): 140 mg/mL | |
|---|---|---|---|---|---|---|---|---|
| | % Main Peak | % HMW | % Main Peak | % HMW | % Main Peak | % HMW | % Main Peak | % HMW |
| 0.0 | 97.90 | 2.10 | 97.86 | 2.14 | 97.83 | 2.17 | 97.85 | 2.15 |
| 1 | 97.91 | 2.09 | 97.79 | 2.21 | 97.65 | 2.35 | 97.47 | 2.53 |
| 2.0 | 97.78 | 2.22 | 97.56 | 2.44 | 97.38 | 2.62 | 97.22 | 2.78 |
| 3.0 | 97.61 | 2.39 | 97.38 | 2.62 | 97.17 | 2.83 | 97.04 | 2.96 |
| 5.5 | 97.39 | 2.61 | 97.10 | 2.90 | 96.79 | 3.21 | | |
| 6.0 | 97.36 | 2.64 | 97.04 | 2.96 | 96.74 | 3.26 | 96.60 | 3.40 |

TABLE 14-3

SE-UPLC Analysis (37° C.)

| Days at 37 C. | F1 (CCC): 80 mg/mL | | F2 (CCC): 100 mg/mL | | F4 (CCC): 120 mg/mL | | F3 (CCC): 140 mg/mL | |
|---|---|---|---|---|---|---|---|---|
| | % Main Peak | % HMW | % Main Peak | % HMW | % Main Peak | % HMW | % Main Peak | % HMW |
| 0.0 | 97.90 | 2.10 | 97.86 | 2.14 | 97.83 | 2.17 | 97.85 | 2.15 |
| 7 | 94.83 | 5.15 | 93.82 | 6.17 | 92.81 | 7.18 | 92.38 | 7.61 |
| 14.0 | 92.00 | 7.77 | 90.31 | 9.39 | 88.67 | 11.13 | 86.90 | 12.91 |

TABLE 14-3-continued

| | SE-UPLC Analysis (37° C.) | | | | | | | |
|---|---|---|---|---|---|---|---|---|
| | F1 (CCC): 80 mg/mL | | F2 (CCC): 100 mg/mL | | F4 (CCC): 120 mg/mL | | F3 (CCC): 140 mg/mL | |
| Days at 37 C. | % Main Peak | % HMW | % Main Peak | % HMW | % Main Peak | % HMW | % Main Peak | % HMW |
| 21.0 | 89.47 | 10.31 | 87.00 | 12.58 | 85.04 | 14.85 | 83.11 | 16.65 |
| 28.0 | 86.76 | 12.71 | 83.98 | 15.55 | 81.19 | 18.46 | 79.44 | 20.29 |

Example 15: High Dose Eylea has Prolonged Duration of Action in the D,L-AAA Model of Sustained Neovascular Leak The effect of a four-fold increase in dose on duration of action of aflibercept to inhibit chronic retinal vascular leak in the D,L-AAA model was determined in this Example.

Animals used were New Zealand White rabbits 3 months post-DL-AAA (DL-α-aminoadipic acid) disease induction. The treatment groups were:

Placebo (formulation buffer) 50 mcl/eye; n=6 eyes
Aflibercept 500 mcg/eye in 50 mcl; n=7 eyes
Aflibercept 2 mg/eye in 50 mcl; n=8 eyes The formulation used in each treatment group was: 10 mM Histidine, 8% sucrose, 0.03% PS20, pH 5.8. Ophthalmic exams, which were performed at baseline and at weeks 1, 2, 4, 6, 7, 9, 10, 11, 13 and 18, were intra-ocular pressure (TOP), red-free (RF) imaging (to determine blood vessel morphology), fluorescein angiography (FA; to determine vascular leak), optical coherence tomography (OCT; to identify vitreal inflammation). Serum (ADA) and plasma (drug levels) were collected at baseline and at weeks 1, 2, 4, 6 and 9.

Data from FA exams of each group are set forth in FIG. 21. These data demonstrated that vascular leak inhibition in the retinas of animals receiving higher doses of aflibercept lasted longer than that of animals receiving lower doses. The number of treated eyes in which vascular permeability was completely inhibited was significantly greater in the 2 mg dose group at all sampling times up to 18 weeks post dosing.

What is claimed is:

1. An aqueous pharmaceutical formulation comprising:
a VEGF receptor fusion protein comprising two polypeptides that each comprises an immunoglobin-like (Ig) domain 2 of VEGFR1, an Ig domain 3 of VEGFR2, and a multimerizing component at a concentration of at least about 100 mg/ml;
about 5% sucrose;
L-arginine;
a histidine-based buffer; and
about 0.03% surfactant;
wherein the formulation has a pH of about 5.0 to about 6.8.

2. The formulation of claim 1 which is suitable for intravitreal administration.

3. The formulation of claim 1 further comprising sodium sulfate, sodium thiocyanate, glycine, NaCl, sodium aspartate and/or sodium glutamate.

4. The formulation of claim 1, wherein the VEGF receptor fusion protein comprises amino acids 27-457 of SEQ ID NO: 2.

5. The formulation of claim 1, wherein the VEGF receptor fusion protein is conbercept.

6. The formulation of claim 1, wherein the VEGF receptor fusion protein is aflibercept.

7. The formulation of claim 6, wherein the aflibercept is at a concentration of:
about 100 mg/ml;
about 111.5 mg/ml;
about 112.0 mg/ml;
about 113.3 mg/ml;
about 114.3 mg/ml;
about 115.6 mg/ml;
about 116.3 mg/ml;
about 120 mg/ml;
about 133 mg/ml;
about 140 mg/ml;
about 150 mg/ml;
about 200 mg/ml;
about 250 mg/ml;
that which contains about 4 mg aflibercept in about 40 µl or less;
that which contains about 6 mg aflibercept in about 60 µl or less;
that which contains about 8 mg aflibercept in about 80 µl or less; or
that which contains about 10 mg aflibercept in about 100 µl or less.

8. The formulation of claim 1 wherein:
(i) the osmolality is about 299 to about 506 mmol/Kg; and/or
(ii) the viscosity is from about 6-15 cP at 20° C.

9. The formulation of claim 1 wherein the pH is 5.8 to 6.5.

10. The formulation of claim 9 wherein the pH is about 5.8.

11. The formulation of claim 1, wherein the surfactant is a non-ionic surfactant.

12. The formulation of claim 11, wherein the non-ionic surfactant is selected from the group consisting of polysorbate 20, polysorbate 80, poloxamer 188, polyethylene glycol 3350 and mixtures thereof.

13. The formulation of claim 1, wherein the histidine-based buffer comprises histidine hydrochloride.

14. The formulation of claim 13 comprising about 10 mM to 20 mM histidine-based buffer.

15. The formulation of claim 1, wherein the L-arginine is L-arginine monohydrochloride.

16. The formulation of claim 1 wherein the VEGF receptor fusion protein has less than about 3.5% high molecular weight species immediately after manufacture and purification and/or less than or equal to about 6% high molecular weight species after storage for about 24 months at about 2-8° C.

17. A method for treating an angiogenic eye disorder in a subject in need thereof, the method comprising intravitreally injecting more than about 2 mg of the VEGF receptor fusion protein in a formulation of claim 1 into an eye of the subject.

18. The method of claim 17, comprising injecting about 4 mg, about 6 mg, about 8 mg or about 10 mg of the VEGF receptor fusion protein into the eye of the subject.

19. An aqueous pharmaceutical formulation comprising:
at least about 100 mg/ml of a VEGF receptor fusion protein comprising two polypeptides that each comprises an immunoglobin-like (Ig) domain 2 of VEGFR1, an Ig domain 3 of VEGFR2, and a multimerizing component;
about 10-100 mM L-arginine;
sucrose;
a histidine-based buffer; and
a surfactant;
wherein the formulation has a pH of about 5.0 to about 6.8;
wherein the VEGF receptor fusion protein has less than about 3.5% high molecular weight species immediately after manufacture and purification and/or less than or equal to about 6% high molecular weight species after storage for about 24 months at about 2-8° C.

20. The formulation of claim 19, wherein the VEGF receptor fusion protein is aflibercept.

21. The formulation of claim 19 wherein the VEGF receptor fusion protein is conbercept.

22. A container or injection device comprising the formulation of claim 19.

23. The container or injection device of claim 22, which is an injection device that is a pre-filled syringe.

24. A method for preparing the formulation of claim 19, comprising combining the VEGF receptor fusion protein, L-arginine, sucrose, histidine-based buffer, and surfactant into a single aqueous composition.

25. The method of claim 24, further comprising loading a volume of the formulation into a syringe.

26. A formulation which is the product of the method of claim 24.

27. A method for administering a formulation of claim 19 to a subject comprising intravitreally injecting the formulation into an eye of the subject.

28. A method for treating an angiogenic eye disorder in a subject in need thereof comprising administering an intravitreal injection of more than about 2 mg of the VEGF receptor fusion protein in a formulation of claim 19 to an eye of the subject.

29. The method of claim 28 comprising administering about 4 mg, about 6 mg, about 8 mg or about 10 mg of the VEGF receptor fusion protein to the eye of the subject.

30. The method of claim 28 wherein the VEGF receptor fusion protein is administered in about 100 microliters or less.

31. The method of claim 28 wherein more than about 2.0 mg of the VEGF receptor fusion protein is injected once every 8, 9, 10, 11, 12, 13, 14, 15, 16, 17, 18, 19, 20, 21, 22, 23 or 24 weeks.

32. The method of claim 28, wherein the angiogenic eye disorder is age-related macular degeneration (wet), macular edema, macular edema following retinal vein occlusion, retinal vein occlusion (RVO), central retinal vein occlusion (CRVO) branch retinal vein occlusion (BRVO), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, diabetic retinopathy, non-proliferative diabetic retinopathy and/or proliferative diabetic retinopathy.

33. The method of claim 32 for treating age-related macular degeneration (wet), diabetic retinopathy or diabetic macular edema, comprising intravitreally injecting, into the eye of the subject, about 8 mg of aflibercept in said formulation.

34. The method of claim 33 wherein the angiogenic eye disorder is age-related macular degeneration (wet).

35. The method of claim 33 wherein the angiogenic eye disorder is diabetic retinopathy.

36. The method of claim 33 wherein the angiogenic eye disorder is diabetic macular edema.

* * * * *

UNITED STATES PATENT AND TRADEMARK OFFICE
CERTIFICATE OF CORRECTION

PATENT NO. : 11,103,552 B2
APPLICATION NO. : 16/409631
DATED : August 31, 2021
INVENTOR(S) : Kenneth S. Graham et al.

Page 1 of 1

It is certified that error appears in the above-identified patent and that said Letters Patent is hereby corrected as shown below:

In the Claims

Claim 1
Column 61, Line 32:
"immunoglobin-like"
Should read:
 --immunoglobulin-like--

Claim 19
Column 63, Line 9:
"immunoglobin-like"
Should read:
--immunoglobulin-like--

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*

```
SEQUENCE LISTING

<160> NUMBER OF SEQ ID NOS: 2

<210> SEQ ID NO 1
<211> LENGTH: 1377
<212> TYPE: DNA
<213> ORGANISM: Homo sapiens

<400> SEQUENCE: 1
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata agaaacttgt aaaccgagac     540
ctaaaaaccc agtctgggag tgagatgaag aaattttttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgt cagcgtcct caccgtcctg     960 caccaggact ggctgaatgg caaggagtac aagtgcaagg tctccaacaa agccctccca    1020
```

-continued

```
gcccccatcg agaaaaccat ctccaaagcc aaagggcagc cccgagaacc acaggtgtac    1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga      1377
```

<210> SEQ ID NO 2
<211> LENGTH: 458
<212> TYPE: PRT
<213> ORGANISM: Homo sapiens
<220> FEATURE:
<221> NAME/KEY: SIGNAL
<222> LOCATION: (1)..(26)

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300
```

-continued

```
Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
        340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
        450                 455
```